United States Patent
Bramucci et al.

(10) Patent No.: US 8,455,225 B2
(45) Date of Patent: Jun. 4, 2013

(54) YEAST WITH INCREASED BUTANOL TOLERANCE INVOLVING HIGH OSMOLARITY/GLYCEROL RESPONSE PATHWAY

(75) Inventors: Michael G. Bramucci, Boothwyn, PA (US); Robert A. Larossa, Chadds Ford, PA (US); Dana R. Smulski, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 325 days.

(21) Appl. No.: 12/643,040

(22) Filed: Dec. 21, 2009

(65) Prior Publication Data

US 2010/0167365 A1 Jul. 1, 2010

Related U.S. Application Data

(60) Provisional application No. 61/141,012, filed on Dec. 29, 2008.

(51) Int. Cl.
*C12P 7/16* (2006.01)
*C12N 1/00* (2006.01)
*C12N 15/74* (2006.01)

(52) U.S. Cl.
USPC .............. 435/160; 435/254.2; 435/254.21; 435/254.22; 435/254.23; 435/471; 435/483

(58) Field of Classification Search
USPC .............. 435/160, 254.2, 254.21, 254.22, 435/254.23, 471, 480
See application file for complete search history.

(56) References Cited

U.S. PATENT DOCUMENTS

| | | | |
|---|---|---|---|
| 4,683,202 | A | 7/1987 | Mullis et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2008/0261230 | A1 | 10/2008 | Liao et al. |
| 2009/0163376 | A1 | 6/2009 | Li et al. |
| 2009/0269823 | A1 | 10/2009 | Bramucci et al. |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Maeda et al., Activation of yeast PBS2 MAPKK by MAPKKKs or by binding of an SH3-containing osmosensor. Science, 1995, vol. 269: 554-558.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
U.S. Appl. No. 12/569,636, filed Sep. 29, 2009, Flint et al.
Altschul, S. F., et al., J. Mol. Biol., 215:403 410 (1990).
Altschul et al. (1997) Nucleic Acids Research 25: 3389-3402.
Ashe et al. The EMBO Journal (2001) 20:6464-6474.
Botstein et al. (1979) Gene 8(1): 17-240.
Hohmann et al. (2007) Methods in Enzymology, Academic Press. 428:29-45.
Chen and Thorner (2007) Biochimica et Biophysica Acta 1773:1311-1340.
Deshpande, Mukund V., Appl. Biochem. Biotechnol., 36:227, (1992).
Fuijta et al. (2006) FEMS Yeast Res 6:744-750.
Frohman et al., PNAS USA 85:8998 (1988).
Gelperin, White et al. (2005) Genes Dev. 19(23):2816-2826).
Gietz et al. (1995) Yeast 11:355-360.
Guo et al., J. Membr. Sci. 245, 199-210 (2004).
Higgins and Sharp, CABIOS. 5:151 153 (1989).
Yeast Protocols, Second Edition (Wei Xiao, ed; Humana Press, Totowa, NJ (2006).
Johnston and Davis (1984) Mol. Cell. Biol. 4(8):1440-1448.
W. R. Pearson, Comput. Methods Genome Res., [Proc. Int. Symp.] (1994), Meeting Date 1992, 111-20. Editor(s): Suhai, Sandor. Plenum: New York, NY.
Thomas D. Brock in Biotechnology: A Textbook of Industrial Microbiology, Second Edition (1989) Sinauer Associates, Inc., Sunderland, MA.
Thein and Wallace, "The use of oligonucleotides as specific hybridization probes in the Diagnosis of Genetic Disorders", in Human Genetic Diseases: A Practical Approach, K. E. Davis Ed., (1986) pp. 33-50, IRL: Herndon, VA.
Loh et al., Science 243:217 (1989).
Lorenz et al. Molec. Biol. of the Cell (2000) 11:183-199.
Silhavy, T. J., Bennan, M. L. and Enquist, L. W. Experiments with Gene Fusions; Cold Spring Harbor Laboratory: Cold Spring Harbor, New York, 1984.
Ohara et al., PNAS USA 86:5673 (1989).
Reid et al. (2002) Yeast 19(4):319-328.
Reed et al. (1989) J. Cell Sci. Suppl. 12:29-37.

(Continued)

Primary Examiner — Ganapathirama Raghu
(74) Attorney, Agent, or Firm — Christine M. Lhulier

(57) ABSTRACT

Increasing tolerance to butanol in yeast has been accomplished by increasing activity of the high osmolarity/glycerol response pathway. Yeast with increased expression of PBS2p, a mitogen activated protein kinase kinase of the MAPK module of the high osmolarity/glycerol response pathway may be used for improved butanol production.

8 Claims, 3 Drawing Sheets

OTHER PUBLICATIONS

Smirnova et al. Molecular and Cellular Bioloty (2005) 25:9340-9340.
Sulter et al., Arch. Microbiol. 153:485 489 (1990).
Tabor, S. et al., Proc. Acad. Sci. USA 82:1074 (1985).
Van Ness and Chen, Nucl. Acids Res. 19:5143 5151 (1991).
Van Voorst et al. (2006) Yeast 25(5):351-359.
Walker, et al., Proc. Natl. Acad. Sci. U.S.A., 89:392 (1992).
Aden et al. Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, Jun. 2002.
Ausubel, F. M. et al., In Current Protocols in Molecular Biology, published by Greene Publishing and Wiley-Interscience, 1987.
Amberg, Burke and Strathern, 2005, Methods in Yeast Genetics, Cold Spring Harbor Laboratory Press, Cold Spring Harbor, NY.
Bellion et al., Microb. Growth C1 Compd., [Int. Symp.], 7th (1993), 415 32. Editor(s): Murrell, J. Collin; Kelly, Don P. Publisher: Intercept, Andover, UK.
Biocomputing: Informatics and Genome Projects (Smith, D. W., Ed.) Academic: NY (1993).
Computational Molecular Biology (Lesk, A. M., Ed.) Oxford University: NY (1988).
Computer Analysis of Sequence Data, Part I (Griffin, A. M., and Griffin, H. G., Eds.) Humania: NJ (1994).
Doherty and Malone, Conceptual Design of Distillation Systems, McGraw Hill, New York, 2001.
Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC (1994).
Methods in Enzymology, vol. 194, Guide to Yeast Genetics and Molecular and Cell Biology Part A, 2004, Christine Guthrie and Gerald R. Fink (Eds.), Elsevier Academic Press, San Diego, CA.
Methods in Yeast Genetics, 2005, Cold Spring Harbor Laboratory Press, Cold Spring Harbor, NY.
Rychlik, W., In Methods in Molecular Biology, White, B. A. Ed., (1993) vol. 15, pp. 31-39, PCR Protocols: Current Methods and Applications. Humania: Totowa, NJ.
Sambrook, J., Fritsch, E. F. and Maniatis, T. Molecular Cloning: A Laboratory Manual, 3rd ed., Cold Spring Harbor Laboratory: Cold Spring Harbor, NY (2001), particularly Chapter 11 and Table 11.1.
Sequence Analysis in Molecular Biology (von Heinje, G., Ed.) Academic (1987).
Sequence Analysis Primer (Gribskov, M. and Devereux, J., Eds.) Stockton: NY(1991).

* cited by examiner

SEQUENCE LISTING

<160> NUMBER OF SEQ ID NOS: 97

<210> SEQ ID NO 1
<211> LENGTH: 1179
<212> TYPE: DNA
<213> ORGANISM: Clostridium acetobutylicum

<400> SEQUENCE: 1

```
atgaaagaag ttgtaatagc tagtgcagta agaacagcga ttggatctta tggaaagtct      60
cttaaggatg taccagcagt agatttagga gctacagcta taaaggaagc agttaaaaaa     120
gcaggaataa aaccagagga tgttaatgaa gtcattttag gaaatgttct tcaagcaggt     180
ttaggacaga atccagcaag acaggcatct tttaaagcag gattaccagt tgaaattcca     240
gctatgacta ttaataaggt ttgtggttca ggacttagaa cagttagctt agcagcacaa     300
attataaaag caggagatgc tgacgtaata atagcaggtg gtatggaaaa tatgtctaga     360
gctccttact tagcgaataa cgctagatgg ggatatagaa tgggaaacgc taaatttgtt     420
gatgaaatga tcactgacgg attgtgggat gcatttaatg attaccacat gggaataaca     480
gcagaaaaca tagctgagag atggaacatt tcaagagaag aacaagatga gtttgctctt     540
gcatcacaaa aaaagctga agaagctata aaatcaggtc aatttaaaga tgaaatagtt     600
cctgtagtaa ttaaaggcag aaagggagaa actgtagttg atacagatga gcaccctaga     660
```

```
tttggatcaa ctatagaagg acttgcaaaa ttaaaacctg ccttcaaaaa agatggaaca    720
gttacagctg gtaatgcatc aggattaaat gactgtgcag cagtacttgt aatcatgagt    780
gcagaaaaag ctaaagagct tggagtaaaa ccacttgcta agatagtttc ttatggttca    840
gcaggagttg acccagcaat aatgggatat ggacctttct atgcaacaaa agcagctatt    900
gaaaaagcag gttggacagt tgatgaatta gatttaatag aatcaaatga agcttttgca    960
gctcaaagtt tagcagtagc aaaagattta aaatttgata tgaataaagt aaatgtaaat   1020
ggaggagcta ttgcccttgg tcatccaatt ggagcatcag gtgcaagaat actcgttact   1080
cttgtacacg caatgcaaaa aagagatgca aaaaaaggct tagcaacttt atgtataggt   1140
ggcggacaag gaacagcaat attgctagaa aagtgctag                          1179
```

<210> SEQ ID NO 2
<211> LENGTH: 392
<212> TYPE: PRT
<213> ORGANISM: Clostridium acetobutylicum

<400> SEQUENCE: 2

```
Met Lys Glu Val Val Ile Ala Ser Ala Val Arg Thr Ala Ile Gly Ser
1               5                  10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285
```

-continued

Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Ala Ile Ala Leu Gly His Pro Ile Gly Ala
                340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
        370                 375                 380

Thr Ala Ile Leu Leu Glu Lys Cys
385                 390

<210> SEQ ID NO 3
<211> LENGTH: 1179
<212> TYPE: DNA
<213> ORGANISM: Clostridium acetobutylicum

<400> SEQUENCE: 3
atgagagatg tagtaatagt aagtgctgta agaactgcaa taggagcata tggaaaaaca      60
ttaaaggatg tacctgcaac agagttagga gctatagtaa taaggaagc tgtaagaaga     120
gctaatataa atccaaatga gattaatgaa gttatttttg gaaatgtact tcaagctgga     180
ttaggccaaa acccagcaag acaagcagca gtaaaagcag gattaccttt agaaacacct     240
gcgtttacaa tcaataaggt ttgtggttca ggtttaagat ctataagttt agcagctcaa     300
attataaaag ctggagatgc tgataccatt gtagtaggtg gtatggaaaa tatgtctaga     360
tcaccatatt tgattaacaa tcagagatgg ggtcaaagaa tgggagatag tgaattagtt     420
gatgaaatga taaaggatgg tttgtgggat gcatttaatg gatatcatat gggagtaact     480
gcagaaaata ttgcagaaca atggaatata acaagagaag agcaagatga attttcactt     540
atgtcacaac aaaaagctga aaaagccatt aaaaatggag aatttaagga tgaaatagtt     600
cctgtattaa taaagactaa aaaaggtgaa atagtctttg atcaagatga atttcctaga     660
ttcggaaaca ctattgaagc attaagaaaa cttaaaccta ttttcaagga aaatggtact     720
gttacagcag gtaatgcatc cggattaaat gatggagctg cagcactagt aataatgagc     780
gctgataaag ctaacgctct cggaataaaa ccacttgcta gattacttc ttacggatca     840
tatgggtag atccatcaat aatgggatat ggagcttttt atgcaactaa agctgcctta     900
gataaaatta atttaaaacc tgaagactta gatttaattg aagctaacga ggcatatgct     960
tctcaaagta tagcagtaac tagagattta aatttagata tgagtaaagt taatgttaat    1020
ggtggagcta tagcacttgg acatccaata ggtgcatctg gtgcacgtat tttagtaaca    1080
ttactatacg ctatgcaaaa aagagattca aaaaaaggtc ttgctactct atgtattggt    1140
ggaggtcagg gaacagctct cgtagttgaa agagactaa                           1179

<210> SEQ ID NO 4
<211> LENGTH: 392
<212> TYPE: PRT
<213> ORGANISM: Clostridium acetobutylicum

<400> SEQUENCE: 4

Met Arg Asp Val Val Ile Val Ser Ala Val Arg Thr Ala Ile Gly Ala
1               5                   10                  15

```
Tyr Gly Lys Thr Leu Lys Asp Val Pro Ala Thr Glu Leu Gly Ala Ile
             20                  25                  30
Val Ile Lys Glu Ala Val Arg Ala Asn Ile Asn Pro Asn Glu Ile
         35                  40                  45
Asn Glu Val Ile Phe Gly Asn Val Leu Gln Ala Gly Leu Gly Gln Asn
 50                  55                  60
Pro Ala Arg Gln Ala Ala Val Lys Ala Gly Leu Pro Leu Glu Thr Pro
 65                  70                  75                  80
Ala Phe Thr Ile Asn Lys Val Cys Gly Ser Gly Leu Arg Ser Ile Ser
                 85                  90                  95
Leu Ala Ala Gln Ile Ile Lys Ala Gly Asp Ala Asp Thr Ile Val Val
             100                 105                 110
Gly Gly Met Glu Asn Met Ser Arg Ser Pro Tyr Leu Ile Asn Asn Gln
         115                 120                 125
Arg Trp Gly Gln Arg Met Gly Asp Ser Glu Leu Val Asp Glu Met Ile
130                 135                 140
Lys Asp Gly Leu Trp Asp Ala Phe Asn Gly Tyr His Met Gly Val Thr
145                 150                 155                 160
Ala Glu Asn Ile Ala Glu Gln Trp Asn Ile Thr Arg Glu Glu Gln Asp
                 165                 170                 175
Glu Phe Ser Leu Met Ser Gln Gln Lys Ala Glu Lys Ala Ile Lys Asn
             180                 185                 190
Gly Glu Phe Lys Asp Glu Ile Val Pro Val Leu Ile Lys Thr Lys Lys
         195                 200                 205
Gly Glu Ile Val Phe Asp Gln Asp Glu Phe Pro Arg Phe Gly Asn Thr
210                 215                 220
Ile Glu Ala Leu Arg Lys Leu Lys Pro Ile Phe Lys Glu Asn Gly Thr
225                 230                 235                 240
Val Thr Ala Gly Asn Ala Ser Gly Leu Asn Asp Gly Ala Ala Ala Leu
                 245                 250                 255
Val Ile Met Ser Ala Asp Lys Ala Asn Ala Leu Gly Ile Lys Pro Leu
             260                 265                 270
Ala Lys Ile Thr Ser Tyr Gly Ser Tyr Gly Val Asp Pro Ser Ile Met
         275                 280                 285
Gly Tyr Gly Ala Phe Tyr Ala Thr Lys Ala Ala Leu Asp Lys Ile Asn
290                 295                 300
Leu Lys Pro Glu Asp Leu Asp Leu Ile Glu Ala Asn Glu Ala Tyr Ala
305                 310                 315                 320
Ser Gln Ser Ile Ala Val Thr Arg Asp Leu Asn Leu Asp Met Ser Lys
                 325                 330                 335
Val Asn Val Asn Gly Gly Ala Ile Ala Leu Gly His Pro Ile Gly Ala
             340                 345                 350
Ser Gly Ala Arg Ile Leu Val Thr Leu Leu Tyr Ala Met Gln Lys Arg
         355                 360                 365
Asp Ser Lys Lys Gly Leu Ala Thr Leu Cys Ile Gly Gly Gly Gln Gly
370                 375                 380
Thr Ala Leu Val Val Glu Arg Asp
385                 390

<210> SEQ ID NO 5
<211> LENGTH: 849
<212> TYPE: DNA
<213> ORGANISM: Clostridium acetobutylicum

<400> SEQUENCE: 5
```

```
atgaaaaagg tatgtgttat aggtgcaggt actatgggtt caggaattgc tcaggcattt    60
gcagctaaag gatttgaagt agtattaaga gatattaaag atgaatttgt tgatagagga   120
ttagatttta tcaataaaaa tctttctaaa ttagttaaaa aaggaaagat agaagaagct   180
actaaagttg aaatcttaac tagaatttcc ggaacagttg accttaatat ggcagctgat   240
tgcgatttag ttatagaagc agctgttgaa agaatggata ttaaaaagca gattttgct    300
gacttagaca atatatgcaa gccagaaaca attcttgcat caaatacatc atcactttca   360
ataacagaag tggcatcagc aactaaaaga cctgataagg ttataggtat gcatttcttt   420
aatccagctc ctgttatgaa gcttgtagag gtaataagag aatagctac atcacaagaa    480
acttttgatg cagttaaaga gacatctata gcaataggaa aagatcctgt agaagtagca   540
gaagcaccag gatttgttgt aaatagaata ttaataccaa tgattaatga agcagttggt   600
atattagcag aaggaatagc ttcagtagaa gacatagata aagctatgaa acttggagct   660
aatcacccaa tggaccatt agaattaggt gattttatag gtcttgatat atgtcttgct    720
ataatggatg ttttatactc agaaactgga gattctaagt atagaccaca tacattactt   780
aagaagtatg taagagcagg atggcttgga agaaaatcag gaaaaggttt ctacgattat   840
tcaaaataa                                                            849

<210> SEQ ID NO 6
<211> LENGTH: 282
<212> TYPE: PRT
<213> ORGANISM: Clostridium acetobutylicum

<400> SEQUENCE: 6

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220
```

```
Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280

<210> SEQ ID NO 7
<211> LENGTH: 786
<212> TYPE: DNA
<213> ORGANISM: Clostridium acetobutylicum

<400> SEQUENCE: 7
atggaactaa acaatgtcat ccttgaaaag gaaggtaaag ttgctgtagt taccattaac      60
agacctaaag cattaaatgc gttaaatagt gatacactaa agaaatggga ttatgtttta    120
ggtgaaattg aaaatgatag cgaagtactt gcagtaattt taactggagc aggagaaaaa    180
tcatttgtag caggagcaga tatttctgag atgaaggaaa tgaataccat tgaaggtaga    240
aaattcggga tacttggaaa taagtgtttt agaagattag aacttcttga aaagcctgta    300
atagcagctg ttaatggttt tgctttagga ggcggatgcg aaatagctat gtcttgtgat    360
ataagaatag cttcaagcaa cgcaagattt ggtcaaccag aagtaggtct cggaataaca    420
cctggttttg gtggtacaca aagactttca agattagttg aatgggcat ggcaaagcag    480 cttatattta ctgcacaaaa tataaaggca gatgaagcat taagaatcgg acttgtaaat    540
aaggtagtag aacctagtga attaatgaat acagcaaaag aaattgcaaa caaaattgtg    600
agcaatgctc cagtagctgt taagttaagc aaacaggcta ttaatagagg aatgcagtgt    660
gatattgata ctgctttagc atttgaatca gaagcatttg gagaatgctt ttcaacagag    720
gatcaaaagg atgcaatgac agcttttcata gagaaaagaa aaattgaagg cttcaaaat    780 agatag                                                              786

<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125
```

```
Arg Phe Gly Gln Pro Glu Val Gly Leu Gly Ile Thr Pro Gly Phe Gly
        130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
                180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 9
<211> LENGTH: 1197
<212> TYPE: DNA
<213> ORGANISM: Clostridium acetobutylicum

<400> SEQUENCE: 9
atgatagtaa aagcaaagtt tgtaaaagga tttatcagag atgtacatcc ttatggttgc      60
agaagggaag tactaaatca aatagattat tgtaagaagg ctattgggtt taggggacca     120
aagaaggttt taattgttgg agcctcatct gggtttggtc ttgctactag aatttcagtt     180
gcatttggag gtccagaagc tcacacaatt ggagtatcct atgaaacagg agctacagat     240
agaagaatag gaacagcggg atggtataat aacatatttt ttaaagaatt tgctaaaaaa     300
aaaggattag ttgcaaaaaa cttcattgag gatgcctttt ctaatgaaac caaagataaa     360
gttattaagt atataaagga tgaatttggt aaaatagatt tatttgttta gtttagct      420 gcgcctagga gaaaggacta taaaactgga atgtttata cttcaagaat aaaaacaatt      480
ttaggagatt ttgagggacc gactattgat gttgaaagag acgagattac tttaaaaaag     540
gttagtagtg ctagcattga agaaattgaa gaaactagaa aggtaatggg tggagaggat     600
tggcaagagt ggtgtgaaga gctgctttat gaagattgtt tttcggataa agcaactacc     660
atagcatact cgtatatagg atccccaaga acctacaaga tatatagaga aggtactata     720
ggaatagcta aaaaggatct tgaagataag gctaagctta taatgaaaaa acttaacaga     780
gttataggtg gtagagccttt tgtgtctgtg aataaagcat tagttacaaa agcaagtgca     840
tatattccaa cttttcctct ttatgcagct attttatata aggtcatgaa agaaaaaaat     900
attcatgaaa attgtattat gcaaattgag agaatgtttt ctgaaaaaat atattcaaat     960 gaaaaatac aatttgatga caagggaaga ttaaggatgg acgatttaga gcttagaaaa    1020
gacgttcaag acgaagttga tagaatatgg agtaatatta ctcctgaaaa ttttaaggaa    1080
ttatctgatt ataagggata caaaaaagaa ttcatgaact taaacggttt tgatctagat    1140
ggggttgatt atagtaaaga cctggatata gaattattaa gaaaattaga accttaa      1197

<210> SEQ ID NO 10
<211> LENGTH: 398
<212> TYPE: PRT
<213> ORGANISM: Clostridium acetobutylicum
```

```
<400> SEQUENCE: 10

Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
            115                 120                 125

Phe Gly Lys Ile Asp Leu Phe Val Tyr Ser Leu Ala Ala Pro Arg Arg
        130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Lys Ile Tyr Ser Asn
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395

<210> SEQ ID NO 11
```

```
<211> LENGTH: 1407
<212> TYPE: DNA
<213> ORGANISM: Clostridium beijerinckii

<400> SEQUENCE: 11
atgaataaag acacactaat acctacaact aaagatttaa aagtaaaaac aaatggtgaa      60
aacattaatt taagaactca caggataat tcttcatgtt tcggagtatt cgaaaatgtt     120
gaaaatgcta taagcagcgc tgtacacgca caaaagatat tatcccttca ttatacaaaa     180
gagcaaagag aaaaaatcat aactgagata agaaggccg cattacaaaa taagaggtc       240 ttggctacaa tgattctaga agaaacacat atgggaagat atgaggataa atattaaaa     300 catgaattgg tagctaaata tactcctggt acagaagatt taactactac tgcttggtca     360
ggtgataatg tcttacagt tgtagaaatg tctccatatg tgttatagg tgcaataact     420 ccttctacga atccaactga aactgtaata tgtaatagca taggcatgat agctgctgga     480
aatgctgtag tatttaacgg acacccatgc gctaaaaaat gtgttgcctt tgctgttgaa     540
atgataaata aggcaattat ttcatgtggc ggtcctgaaa atctagtaac aactataaaa     600
aatccaacta tggagtctct agatgcaatt attaagcatc cttcaataaa acttctttgc     660
ggaactgggg gtccaggaat ggtaaaaacc ctcttaaatt ctggtaagaa agctataggt     720
gctggtgctg gaaatccacc agttattgta gatgatactg ctgatataga aaaggctggt     780
aggagcatca ttgaaggctg ttctttgat aataattac cttgtattgc agaaaaagaa     840
gtatttgttt ttgagaatgt tgcagatgat ttaatatcta acatgctaaa aaataatgct     900
gtaattataa atgaagatca agtatcaaaa ttaatagatt tagtattaca aaaaaataat     960
gaaactcaag aatactttat aaacaaaaaa tgggtaggaa aagatgcaaa attattctta    1020
gatgaaatag atgttgagtc tccttcaaat gttaaatgca taatctgcga agtaaatgca    1080
aatcatccat ttgttatgac agaactcatg atgccaatat tgccaattgt aagagttaaa    1140
gatatagatg aagctattaa atatgcaaag atagcagaac aaaatagaaa acatagtgcc    1200 tatattatt ctaaaaatat agacaaccta aatagatttg aaagagaaat agatactact     1260
atttttgtaa agaatgctaa atcttttgct ggtgttggtt atgaagcaga aggatttaca    1320
actttcacta ttgctggatc tactggtgag ggaataaccct ctgcaaggaa ttttacaaga    1380
caaagaagat gtgtacttgc cggctaa                                        1407

<210> SEQ ID NO 12
<211> LENGTH: 468
<212> TYPE: PRT
<213> ORGANISM: Clostridium beijerinckii

<400> SEQUENCE: 12

Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95
```

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 13
<211> LENGTH: 1215
<212> TYPE: DNA
<213> ORGANISM: Clostridium acetobutylicum

<400> SEQUENCE: 13

```
atggttgatt tcgaatattc aataccaact agaattttt tcggtaaaga taagataaat      60
gtacttggaa gagagcttaa aaaatatggt tctaaagtgc ttatagttta tggtggagga     120
agtataaaga gaaatggaat atatgataaa gctgtaagta tacttgaaaa aaacagtatt     180
aaattttatg aacttgcagg agtagagcca atccaagag taactacagt tgaaaaagga     240
gttaaaatat gtagagaaaa tggagttgaa gtagtactag ctataggtgg aggaagtgca     300
atagattgcg caaaggttat agcagcagca tgtgaatatg atggaaatcc atgggatatt     360
gtgttagatg gctcaaaaat aaaaagggtg cttcctatag ctagtatatt aaccattgct     420
gcaacaggat cagaaatgga tacgtgggca gtaataaaata atatggatac aaacgaaaaa     480
ctaattgcgg cacatccaga tatggctcct aagttttcta tattagatcc aacgtatacg     540
tataccgtac ctaccaatca aacagcagca ggaacagctg atattatgag tcatatattt     600
gaggtgtatt ttagtaatac aaaaacagca tatttgcagg atagaatggc agaagcgtta     660
ttaagaactt gtattaaata tggaggaata gctcttgaga gccggatga ttatgaggca      720
agagccaatc taatgtgggc ttcaagtctt gcgataaatg gacttttaac atatggtaaa     780
gacactaatt ggagtgtaca cttaatggaa catgaattaa gtgcttatta cgacataaca     840
cacggcgtag ggcttgcaat tttaacacct aattggatgg agtatatttt aaataatgat     900
acagtgtaca gtttgttga atatggtgta aatgtttggg aatagacaa agaaaaaaat      960
cactatgaca tagcacatca agcaatacaa aaaacaagag attactttgt aaatgtacta    1020
ggtttaccat ctagactgag agatgttgga attgaagaag aaaaattgga cataatggca    1080
aaggaatcag taaagcttac aggaggaacc ataggaaacc taagaccagt aaacgcctcc    1140
gaagtcctac aaatattcaa aaatctgtg taaaacgcct ccgaagtcct acaaatattc    1200
aaaaaatctg tgtaa                                                    1215
```

<210> SEQ ID NO 14
<211> LENGTH: 390
<212> TYPE: PRT
<213> ORGANISM: Clostridium acetobutylicum

<400> SEQUENCE: 14

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160
```

```
Leu Ile Ala Ala His Pro Asp Met Ala Pro Lys Phe Ser Ile Leu Asp
            165                 170                 175

Pro Thr Tyr Thr Tyr Thr Val Pro Thr Asn Gln Thr Ala Ala Gly Thr
        180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390

<210> SEQ ID NO 15
<211> LENGTH: 1170
<212> TYPE: DNA
<213> ORGANISM: Clostridium acetobutylicum

<400> SEQUENCE: 15
atgctaagtt ttgattattc aataccaact aaagtttttt ttggaaaagg aaaaatagac       60
gtaattggag aagaaattaa gaaatatggc tcaagagtgc ttatagttta tggcggagga      120
agtataaaaa ggaacggtat atatgataga gcaacagcta tattaaaaga aaacaatata      180
gctttctatg aactttcagg agtagagcca atcctagga taacaacagt aaaaaaaggc       240
atagaaatat gtagagaaaa taatgtggat ttagtattag caataggggg aggaagtgca      300
atagactgtt ctaaggtaat tgcagctgga gtttattatg atggcgatac atgggacatg      360
gttaaagatc catctaaaat aactaaagtt cttccaattg caagtatact tactctttca      420
gcaacagggt ctgaaatgga tcaaattgca gtaattttca aatatgagac taatgaaaag      480 cttgagtag acatgatga tatgagacct aaattttcag tgttagatcc tacatatact       540
tttacagtac ctaaaaatca aacagcagcg ggaacagctg acattatgag tcacaccttt      600
gaatcttact ttagtggtgt tgaaggtgct tatgtgcagg acgtatagc agaagcaatc       660 ttaagaacat gtataaagta tggaaaaata gcaatggaga agactgatga ttacgaggct      720
agagctaatt tgatgtgggc ttcaagttta gctataaatg gtctattatc acttggtaag      780
gatagaaaat ggagttgtca tcctatggaa cacgagttaa gtgcatatta tgatataaca      840
```

```
catggtgtag gacttgcaat tttaacacct aattggatgg aatatattct aaatgacgat    900
acacttcata aatttgtttc ttatggaata aatgtttggg aatagacaa gaacaaagat    960 aactatgaaa tagcacgaga ggctattaaa aatacgagag aatactttaa ttcattgggt   1020
attccttcaa agcttagaga agttggaata ggaaaagata aactagaact aatggcaaag   1080
caagctgtta gaaattctgg aggaacaata ggaagtttaa gaccaataaa tgcagaggat   1140
gttcttgaga tatttaaaaa atcttattaa                                    1170
```

<210> SEQ ID NO 16
<211> LENGTH: 389
<212> TYPE: PRT
<213> ORGANISM: Clostridium acetobutylicum

<400> SEQUENCE: 16

```
Met Leu Ser Phe Asp Tyr Ser Ile Pro Thr Lys Val Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320
```

Asn Tyr Glu Ile Ala Arg Glu Ala Ile Lys Asn Thr Arg Glu Tyr Phe
            325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
            355                 360                 365

Thr Ile Gly Ser Leu Arg Pro Ile Asn Ala Glu Asp Val Leu Glu Ile
    370                 375                 380

Phe Lys Lys Ser Tyr
385

<210> SEQ ID NO 17
<211> LENGTH: 780
<212> TYPE: DNA
<213> ORGANISM: Klebsiella pneumoniae

<400> SEQUENCE: 17
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc     180 ggcaccttta tgagctgga cggggagctg atcgccttca gcagtcaggt ctatcagctg     240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca aatcccctct gacaacctgt tctgcgccct gcgcatcgac     420 ggccattcc gccatgccca tacccgcacc gtgccgcgcc agacgccgcc gtaccgggcg     480
atgaccgacg tcctcgacga tcagccggtg ttccgcttta accagcgcga aggggtgctg     540
gtcggcttcc ggaccccgca gcatatgcag gggatcaacg tcgccgggta tcacgagcac     600
tttattaccg atgaccgcaa aggcggcggt cacctgctgg attaccagct cgaccatggg     660
gtgctgacct tcggcgaaat tcacaagctg atgatcgacc tgcccgccga cagcgcgttc     720
ctgcaggcta atctgcatcc cgataatctc gatgccgcca tccgttccgt agaaagttaa     780

<210> SEQ ID NO 18
<211> LENGTH: 259
<212> TYPE: PRT
<213> ORGANISM: Klebsiella pneumoniae

<400> SEQUENCE: 18

Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile

```
            115                 120                 125
Pro Ser Asp Asn Leu Phe Cys Ala Leu Arg Ile Asp Gly His Phe Arg
    130                 135                 140

His Ala His Thr Arg Thr Val Pro Arg Gln Thr Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser

<210> SEQ ID NO 19
<211> LENGTH: 1680
<212> TYPE: DNA
<213> ORGANISM: Klebsiella pneumoniae

<400> SEQUENCE: 19
atggacaaac agtatccggt acgccagtgg gcgcacggcg ccgatctcgt cgtcagtcag      60
ctggaagctc agggagtacg ccaggtgttc ggcatccccg cgccaaaaat tgacaaggtc     120
ttcgactcac tgctggattc ctcgattcgc attattccgg tacgccacga agccaacgcc     180
gcgtttatgg ccgccgccgt cggacgcatt accggcaaag cgggcgtggc gctggtcacc     240
tccggtccgg gctgttccaa cctgatcacc ggcatggcca ccgcgaacag cgaaggcgac     300
ccggtggtgg ccctgggcgg cgcggtaaaa cgcgccgata agcgaagca ggtccaccag     360 agtatggata cggtggcgat gttcagcccg gtcaccaaat acgccgtcga ggtgacggcg     420
ccggatgcgc tggcggaagt ggtctccaac gccttccgcg ccgccgagca gggccggccg     480
ggcagcgcgt tcgttagcct gccgcaggat gtggtcgatg cccgtcag cggcaaagtg       540 ctgccggcca gcggggcccc gcagatgggc gccgcgccgg atgatgccat cgaccaggtg     600
gcgaagctta tcgcccaggc gaagaacccg atcttcctgc tcggcctgat ggccagccag     660
ccggaaaaca gcaaggcgct cgccgtttg ctggagacca gccatattcc agtcaccagc      720
acctatcagg ccgccggagc ggtgaatcag gataacttct ctcgcttcgc cggccgggtt     780
gggctgttta caaccaggc cggggaccgt ctgctgcagc tcgccgacct ggtgatctgc      840
atcggctaca gcccggtgga atacgaaccg gcgatgtgga cagcggcaa cgcgacgctg      900 gtgcacatcg acgtgctgcc cgcctatgaa gagcgcaact acaccccgga tgtcgagctg     960
gtgggcgata tcgccggcac tctcaacaag ctggcgcaaa atatcgatca tcggctggtg    1020
ctctccccgc aggcggcgga gatcctccgc gaccgccagc accagcgcga gctgctggac    1080
cgccgcggcg cgcagctgaa ccagtttgcc ctgcatccgc tgcgcatcgt tcgcgccatg    1140
caggacatcg tcaacagcga cgtcacgttg accgtggaca tgggcagctt ccatatctgg    1200
attgcccgct acctgtacag cttccgcgcc cgtcaggtga tgatctccaa cggccagcag    1260
accatgggcg tcgccctgcc ctgggctatc ggcgcctggc tggtcaatcc tgagcgaaaa    1320
```

-continued

```
gtggtctccg tctccggcga cggcggcttc ctgcagtcga gcatggagct ggagaccgcc    1380
gtccgcctga agccaacgt actgcacctg atctgggtcg ataacggcta caacatggtg     1440
gccattcagg aagagaaaaa ataccagcgc ctgtccggcg tcgagttcgg gccgatggat    1500
tttaaagcct atgccgaatc cttcggcgcg aaagggtttg ccgtggaaag cgccgaggcg    1560
ctggagccga ccctgcacgc ggcgatggac gtcgacggcc cggcggtggt ggccattccg    1620
gtggattatc gcgataaccc gctgctgatg ggccagctgc atctgagtca gattctgtaa    1680
```

<210> SEQ ID NO 20
<211> LENGTH: 559
<212> TYPE: PRT
<213> ORGANISM: Klebsiella pneumoniae

<400> SEQUENCE: 20

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320
```

Val Gly Asp Ile Ala Gly Thr Leu Asn Lys Leu Ala Gln Asn Ile Asp
              325                 330                 335

His Arg Leu Val Leu Ser Pro Gln Ala Ala Glu Ile Leu Arg Asp Arg
          340                 345                 350

Gln His Gln Arg Glu Leu Leu Asp Arg Arg Gly Ala Gln Leu Asn Gln
      355                 360                 365

Phe Ala Leu His Pro Leu Arg Ile Val Arg Ala Met Gln Asp Ile Val
  370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
              405                 410                 415

Asn Gly Gln Gln Thr Met Gly Val Ala Leu Pro Trp Ala Ile Gly Ala
          420                 425                 430

Trp Leu Val Asn Pro Glu Arg Lys Val Val Ser Val Ser Gly Asp Gly
      435                 440                 445

Gly Phe Leu Gln Ser Ser Met Glu Leu Glu Thr Ala Val Arg Leu Lys
  450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
              485                 490                 495

Gly Pro Met Asp Phe Lys Ala Tyr Ala Glu Ser Phe Gly Ala Lys Gly
          500                 505                 510

Phe Ala Val Glu Ser Ala Glu Ala Leu Glu Pro Thr Leu His Ala Ala
      515                 520                 525

Met Asp Val Asp Gly Pro Ala Val Val Ala Ile Pro Val Asp Tyr Arg
  530                 535                 540

Asp Asn Pro Leu Leu Met Gly Gln Leu His Leu Ser Gln Ile Leu
545                 550                 555

<210> SEQ ID NO 21
<211> LENGTH: 771
<212> TYPE: DNA
<213> ORGANISM: Klebsiella pneumoniae

<400> SEQUENCE: 21
atgaaaaaag tcgcacttgt taccggcgcc ggccagggga ttggtaaagc tatcgccctt      60
cgtctggtga aggatggatt tgccgtggcc attgccgatt ataacgacgc caccgccaaa     120
gcggtcgcct cggaaatcaa ccaggccggc ggacacgccg tggcggtgaa agtggatgtc     180
tccgaccgcg atcaggtatt tgccgccgtt gaacaggcgc gcaaaacgct gggcggcttc     240
gacgtcatcg tcaataacgc cggtgtggca ccgtctacgc cgatcgagtc cattaccccg     300
gagattgtcg acaaagtcta caacatcaac gtcaaagggg tgatctgggg tattcaggcg     360
gcggtcgagg cctttaagaa agaggggcac ggcgggaaaa tcatcaacgc ctgttcccag     420
gccggccacg tcggcaaccc ggagctggcg gtgtatagct ccagtaaatt cgcggtacgc     480
ggcttaaccc agaccgccgc tcgcgacctc gcgccgctgg gcatcaccgt caacggctac     540
tgcccgggga ttgtcaaaac gccaatgtgg gccgaaattg accgccaggt gtccgaagcc     600
gccggtaaac gcctgggcta cggtaccgcc gagttcgcca aacgcatcac tctcggtcgt     660
ctgtccgagc cggaagatgt cgccgcctgc gtctcctatc ttgccagccc ggattctgat     720
tacatgaccg tcagtcgtt gctgatcgac ggcgggatgg tatttaacta a              771

<210> SEQ ID NO 22
<211> LENGTH: 256
<212> TYPE: PRT
<213> ORGANISM: Klebsiella pneumoniae

<400> SEQUENCE: 22

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255

<210> SEQ ID NO 23
<211> LENGTH: 1665
<212> TYPE: DNA
<213> ORGANISM: Klebsiella oxytoca

<400> SEQUENCE: 23
atgagatcga aaagatttga agcactggcg aaacgccctg tgaatcagga cggcttcgtt      60
aaggagtgga tcgaagaagg ctttatcgcg atggaaagcc cgaacgaccc aaaaccgtcg     120
attaaaatcg ttaacggcgc ggtgaccgag ctggacggga accggtaagc gattttgac      180 ctgatcgacc actttatcgc ccgctacggt atcaacctga accgccgga agaagtgatg      240 gcgatggatt cggtcaagct ggccaacatg ctgtgcgatc cgaacgttaa acgcagcgaa     300
atcgtcccgc tgaccaccgc gatgacgccg gcgaaaattg tcgaagtggt ttcgcatatg     360
aacgtcgtcg agatgatgat ggcgatgcag aaaatgcgcg cccgccgcac cccgtcccag     420
caggcgcacg tcaccaacgt caagataaac cggtacaga ttgccgccga cgccgccgaa      480
ggggcatggc gcggatttga cgaacaggaa accaccgttg cggtagcgcg ctatgcgccg     540

```
ttcaacgcca tcgcgctgct ggtgggctcg caggtaggcc gtccgggcgt gctgacgcag    600
tgctcgctgg aagaagccac cgagctgaag ctcggcatgc tgggccacac ctgctacgcc    660
gaaaccatct ccgtctacgg caccgagccg gtctttaccg acggcgacga cacgccgtgg    720
tcgaagggct tcctcgcctc gtcctacgcc tctcgcgggc tgaaaatgcg ctttacctcc    780
ggctccggct cggaagtgca gatgggctac gccgaaggca aatccatgct ttatctggaa    840
gcgcgctgca tctacatcac caaagccgcg ggcgtacagg gtctgcaaaa cggttccgta    900
agctgcatcg gcgtgccgtc tgcggtgcct ccggcattc gcgcggtgct ggcggaaaac     960
ctgatctgtt cgtcgctgga tctggagtgc gcctccagca cgaccagac cttcacccac    1020 tccgatatgc gtcgtaccgc gcgcctgctg atgcagttcc tgccgggcac cgactttatc   1080
tcctccggtt attccgcggt gccgaactac gacaacatgt cgccggctc caacgaagat    1140 gccgaagact ttgacgacta caacgtcatc cagcgcgacc tgaaggtgga cggcggtttg   1200
cgtccggttc gcgaagagga cgtcatcgcc atccgtaaca aagccgcccg cgcgctgcag   1260
gccgtgtttg ccggaatggg gctgccgccg attaccgatg aagaagttga agccgcgacc    1320
tacgcccacg gttcgaaaga tatgccggag cgcaacatcg tcgaagacat caagttcgcc    1380
caggaaatca tcaataaaaa ccgcaacggt ctggaagtgg tgaaagcgct ggcgcagggc    1440
ggattcaccg acgtggccca ggacatgctc aacatccaga aagctaagct gaccggggac    1500
tacctgcata cctccgcgat tatcgtcggc gacgggcagg tgctgtcagc cgtcaacgac    1560
gtcaacgact atgccggtcc ggcaacgggc tatcgcctgc agggcgaacg ctgggaagag    1620
attaaaaaca tccctggcgc tcttgatccc aacgagattg attaa                    1665
```

\<210\> SEQ ID NO 24
\<211\> LENGTH: 554
\<212\> TYPE: PRT
\<213\> ORGANISM: Klebsiella oxytoca

\<400\> SEQUENCE: 24

```
Met Arg Ser Lys Arg Phe Glu Ala Leu Ala Lys Arg Pro Val Asn Gln
 1               5                  10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175
```

```
Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550

<210> SEQ ID NO 25
<211> LENGTH: 675
<212> TYPE: DNA
<213> ORGANISM: Klebsiella oxytoca

<400> SEQUENCE: 25
```

```
atggaaatta atgaaaaatt gctgcgccag ataattgaag acgtgctcag cgagatgaag      60
ggcagcgata aaccggtctc gtttaatgcg ccggcggcct ccgcggcgcc ccaggccacg     120
ccgcccgccg gcgacggctt cctgacggaa gtgggcgaag cgcgtcaggg aacccagcag     180
gacgaagtga ttatcgccgt cggcccggct ttcggcctgg cgcagaccgt caatatcgtc     240
ggcatcccgc ataagagcat tttgcgcgaa gtcattgccg gtattgaaga agaaggcatt     300
aaggcgcgcg tgattcgctg cttaaatcc tccgacgtgg ccttcgtcgc cgttgaaggt     360
aatcgcctga gcggctccgg catctctatc ggcatccagt cgaaaggcac cacggtgatc     420
caccagcagg ggctgccgcc gctctctaac ctggagctgt tcccgcaggc gccgctgctg     480
accctggaaa cctatcgcca gatcggcaaa aacgccgccc gctatgcgaa cgcgaatcg      540 ccgcagccgg tcccgacgct gaatgaccag atggcgcggc cgaagtacca ggcgaaatcg     600
gccattttgc acattaaaga gaccaagtac gtggtgacgg gcaaaaaccc gcaggaactg     660
cgcgtggcgc tttga                                                     675
```

<210> SEQ ID NO 26
<211> LENGTH: 224
<212> TYPE: PRT
<213> ORGANISM: Klebsiella oxytoca

<400> SEQUENCE: 26

```
Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 27
<211> LENGTH: 522
<212> TYPE: DNA
<213> ORGANISM: Klebsiella oxytoca -continued

<400> SEQUENCE: 27

```
atgaataccg acgcaattga atcgatggta cgcgacgtat tgagccgcat gaacagcctg      60
cagggcgagg cgcctgcggc ggctccggcg gctggcggcg cgtcccgtag cgccagggtc     120
agcgactacc cgctggcgaa caagcacccg gaatgggtga aaaccgccac caataaaacg     180
ctggacgact ttacgctgga aaacgtgctg agcaataaag tcaccgccca ggatatgcgt     240
attccccgg aaaccctgcg cttacaggct tctattgcca agacgcggg ccgcgaccgg      300
ctggcgatga acttcgagcg cgccgccgag ctgaccgcgg taccggacga tcgcattctt     360
gaaatctaca cgccctccg ccctatcgc tcgacgaaag aggagctgct ggcgatcgcc      420
gacgatctcg aaagccgcta tcaggcgaag atttgcgccg ctttcgttcg cgaagcggcc     480
acgctgtacg tcgagcgtaa aaaactcaaa ggcgacgatt aa                        522
```

<210> SEQ ID NO 28
<211> LENGTH: 173
<212> TYPE: PRT
<213> ORGANISM: Klebsiella oxytoca

<400> SEQUENCE: 28

Met Asn Thr Asp Ala Ile Glu Ser Met Val Arg Asp Val Leu Ser Arg
1               5                   10                  15
Met Asn Ser Leu Gln Gly Glu Ala Pro Ala Ala Pro Ala Ala Gly
        20                  25                  30
Gly Ala Ser Arg Ser Ala Arg Val Ser Asp Tyr Pro Leu Ala Asn Lys
    35                  40                  45
His Pro Glu Trp Val Lys Thr Ala Thr Asn Lys Thr Leu Asp Asp Phe
50                  55                  60
Thr Leu Glu Asn Val Leu Ser Asn Lys Val Thr Ala Gln Asp Met Arg
65                  70                  75                  80
Ile Thr Pro Glu Thr Leu Arg Leu Gln Ala Ser Ile Ala Lys Asp Ala
                85                  90                  95
Gly Arg Asp Arg Leu Ala Met Asn Phe Glu Arg Ala Ala Glu Leu Thr
            100                 105                 110
Ala Val Pro Asp Asp Arg Ile Leu Glu Ile Tyr Asn Ala Leu Arg Pro
        115                 120                 125
Tyr Arg Ser Thr Lys Glu Glu Leu Leu Ala Ile Ala Asp Asp Leu Glu
    130                 135                 140
Ser Arg Tyr Gln Ala Lys Ile Cys Ala Ala Phe Val Arg Glu Ala Ala
145                 150                 155                 160
Thr Leu Tyr Val Glu Arg Lys Lys Leu Lys Gly Asp Asp
                165                 170

<210> SEQ ID NO 29
<211> LENGTH: 1041
<212> TYPE: DNA
<213> ORGANISM: Rhodococcus ruber

<400> SEQUENCE: 29

```
atgaaagccc tccagtacac cgagatcggc tccgagccgg tcgtcgtcga cgtccccacc      60
ccggcgcccg gccgggtga gatcctgctg aaggtcaccg cggccggctt gtgccactcg     120
gacatcttcg tgatggacat gccggcagag cagtacatct acggtctcc cctcaccctc      180
ggccacgagg gcgtcggcac cgtcgccgaa ctcggcgccg cgtcaccgg attcgagacg     240
ggggacgccg tcgccgtgta cggccgtgg gggtgcggtg cgtgccacgc gtgcgcgcgc     300
ggccgggaga actactgcac ccgcgccgcc gagctgggca tcaccccgcc cggtctcggc     360
```

```
tcgcccgggt cgatggccga gtacatgatc gtcgactcgg cgcgccacct cgtcccgatc    420
ggggacctcg accccgtcgc ggcggttccg ctcaccgacg cgggcctgac gccgtaccac    480
gcgatctcgc gggtcctgcc cctgctggga cccggctcga ccgcggtcgt catcggggtc    540
ggcggactcg ggcacgtcgg catccagatc ctgcgcgccg tcagcgcggc ccgcgtgatc    600
gccgtcgatc tcgacgacga ccgactcgcg ctcgcccgcg aggtcggcgc cgacgcggcg    660
gtgaagtcgg gcgccggggc ggcggacgcg atccgggagc tgaccggcgg tgagggcgcg    720
acggcggtgt cgacttcgt cggcgcccag tcgacgatcg acacggcgca gcaggtggtc    780
gcgatcgacg ggcacatctc ggtggtcggc atccatgccg gcgcccacgc caaggtcggc    840
ttcttcatga tcccgttcgg cgcgtccgtc gtgacgccgt actggggcac gcggtccgag    900
ctgatggacg tcgtggacct ggcccgtgcc ggccggctcg acatccacac cgagacgttc    960 acccctcgacg agggacccac ggcctaccgg cggctacgcg agggcagcat ccgcggccgc   1020
ggggtggtcg tcccgggctg a                                              1041
```

<210> SEQ ID NO 30
<211> LENGTH: 346
<212> TYPE: PRT
<213> ORGANISM: Rhodococcus ruber

<400> SEQUENCE: 30

```
Met Lys Ala Leu Gln Tyr Thr Glu Ile Gly Ser Glu Pro Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255
```

```
Gln Gln Val Val Ala Ile Asp Gly His Ile Ser Val Val Gly Ile His
                260                 265                 270
Ala Gly Ala His Ala Lys Val Gly Phe Phe Met Ile Pro Phe Gly Ala
            275                 280                 285
Ser Val Val Thr Pro Tyr Trp Gly Thr Arg Ser Glu Leu Met Asp Val
        290                 295                 300
Val Asp Leu Ala Arg Ala Gly Arg Leu Asp Ile His Thr Glu Thr Phe
305                 310                 315                 320
Thr Leu Asp Glu Gly Pro Thr Ala Tyr Arg Arg Leu Arg Glu Gly Ser
                325                 330                 335
Ile Arg Gly Arg Gly Val Val Val Pro Gly
                340                 345

<210> SEQ ID NO 31
<211> LENGTH: 1476
<212> TYPE: DNA
<213> ORGANISM: Escherichia coli

<400> SEQUENCE: 31
```

| | | | | | |
|---|---|---|---|---|---|
| atggctaact | acttcaatac | actgaatctg | cgccagcagc | tggcacagct | gggcaaatgt | 60 |
| cgctttatgg | ccgcgatga | attcgccgat | ggcgcgagct | accttcaggg | taaaaaagta | 120 |
| gtcatcgtcg | gctgtggcgc | acagggtctg | aaccagggcc | tgaacatgcg | tgattctggt | 180 |
| ctcgatatct | cctacgctct | gcgtaaagaa | gcgattgccg | agaagcgcgc | gtcctggcgt | 240 |
| aaagcgaccg | aaaatggttt | taaagtgggt | acttacgaag | aactgatccc | acaggcggat | 300 |
| ctggtgatta | acctgacgcc | ggacaagcag | cactctgatg | tagtgcgcac | cgtacagcca | 360 |
| ctgatgaaag | acggcgcggc | gctgggctac | tcgcacggtt | tcaacatcgt | cgaagtgggc | 420 |
| gagcagatcc | gtaaagatat | caccgtagtg | atggttgcgc | gaaatgccc | aggcaccgaa | 480 |
| gtgcgtgaag | agtacaaacg | tgggttcggc | gtaccgacgc | tgattgccgt | tcacccggaa | 540 |
| aacgatccga | aggcgaagg | catggcgatt | gccaaagcct | gggcggctgc | aaccggtggt | 600 |
| caccgtgcgg | gtgtgctgga | atcgtccttc | gttgcggaag | tgaaatctga | cctgatgggc | 660 |
| gagcaaacca | tcctgtgcgg | tatgttgcag | gctggctctc | tgctgtgctt | cgacaagctg | 720 |
| gtggaagaag | gtaccgatcc | agcatacgca | gaaaaactga | ttcagttcgg | ttgggaaacc | 780 |
| atcaccgaag | cactgaaaca | gggcggcatc | accctgatga | tggaccgtct | ctctaacccg | 840 |
| gcgaaactgc | gtgcttatgc | gctttctgaa | cagctgaaag | agatcatggc | acccctgttc | 900 |
| cagaaacata | tggacgacat | catctccggc | gaattctctt | ccggtatgat | ggcggactgg | 960 |
| gccaacgatg | ataagaaact | gctgacctgg | cgtgaagaga | ccggcaaaac | cgcgtttgaa | 1020 |
| accgcgccgc | agtatgaagg | caaaatcggc | gagcaggagt | acttcgataa | aggcgtactg | 1080 |
| atgattgcga | tggtgaaagc | gggcgttgaa | ctggcgttcg | aaaccatggt | cgattccggc | 1140 |
| atcattgaag | agtctgcata | ttatgaatca | ctgcacgagc | tgccgctgat | tgccaacacc | 1200 |
| atcgcccgta | agcgtctgta | cgaaatgaac | gtggttatct | ctgataccgc | tgagtacggt | 1260 |
| aactatctgt | tctcttacgc | ttgtgtgccg | ttgctgaaac | cgtttatggc | agagctgcaa | 1320 |
| ccgggcgacc | tggtaaagc | tattccggaa | ggcgcggtag | ataacgggca | actgcgtgat | 1380 |
| gtgaacgaag | cgattcgcag | ccatgcgatt | gagcaggtag | gtaagaaact | gcgcggctat | 1440 |
| atgacagata | tgaaacgtat | tgctgttgcg | ggttaa | | | 1476 |

```
<210> SEQ ID NO 32
<211> LENGTH: 491
```

```
<212> TYPE: PRT
<213> ORGANISM: Escherichia coli

<400> SEQUENCE: 32

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400
```

```
Ile Ala Arg Lys Arg Leu Tyr Glu Met Asn Val Val Ile Ser Asp Thr
            405                 410                 415
Ala Glu Tyr Gly Asn Tyr Leu Phe Ser Tyr Ala Cys Val Pro Leu Leu
        420                 425                 430
Lys Pro Phe Met Ala Glu Leu Gln Pro Gly Asp Leu Gly Lys Ala Ile
            435                 440                 445
Pro Glu Gly Ala Val Asp Asn Gly Gln Leu Arg Asp Val Asn Glu Ala
        450                 455                 460
Ile Arg Ser His Ala Ile Glu Gln Val Gly Lys Lys Leu Arg Gly Tyr
465                 470                 475                 480
Met Thr Asp Met Lys Arg Ile Ala Val Ala Gly
            485                 490

<210> SEQ ID NO 33
<211> LENGTH: 1851
<212> TYPE: DNA
<213> ORGANISM: Escherichia coli

<400> SEQUENCE: 33
atgcctaagt accgttccgc caccaccact catggtcgta atatggcggg tgctcgtgcg      60
ctgtggcgcg ccaccggaat gaccgacgcc gatttcggta agccgattat cgcggttgtg     120
aactcgttca cccaatttgt accgggtcac gtccatctgc gcgatctcgg taaactggtc     180
gccgaacaaa ttgaagcggc tggcggcgtt gccaaagagt caacaccat tgcggtggat      240 gatgggattg ccatgggcca cggggggatg ctttattcac tgccatctcg cgaactgatc     300
gctgattccg ttgagtatat ggtcaacgcc cactgcgccg acgccatggt ctgcatctct     360
aactgcgaca aaatcacccc gggggatgctg atggcttccc tgcgcctgaa tattccggtg     420
atctttgttt ccggcggccc gatggaggcc gggaaaacca actttccga tcagatcatc      480 aagctcgatc tggttgatgc gatgatccag ggcgcagacc cgaaagtatc tgactcccag     540
agcgatcagg ttgaacgttc gcgcgtgtccg acctgcggtt cctgctccgg gatgtttacc      600
gctaactcaa tgaactgcct gaccgaaagcg ctgggcctgt cgcagccggg caacggctcg     660
ctgctggcaa cccacgccga ccgtaagcag ctgttcctta tgctggtaa acgcattgtt       720 gaattgacca acgttatta cgagcaaaac gacgaaagtg cactgccgcg taatatcgcc      780
agtaaggcgg cgtttgaaaa cgccatgacg ctggatatcg cgatgggtgg atcgactaac     840
accgtacttc acctgctggc ggcggcgcag gaagcggaaa tcgacttcac catgagtgat      900
atcgataagc tttcccgcaa ggttccacag ctgtgtaaag ttgcgccgag cacccagaaa     960
taccatatgg aagatgttca ccgtgctggt ggtgttatcg gtattctcgg cgaactggat    1020
cgcgcggggt tactgaaccg tgatgtgaaa aacgtacttg gcctgacgtt gccgcaaacg    1080
ctggaacaat acgacgttat gctgacccag gatgacgcgg taaaaaatat gttccgcgca    1140
ggtcctgcag gcattcgtac cacacaggca ttctcgcaag attgccgttg ggatacgctg    1200
gacgacgatc gcgccaatgg ctgtatccgc tcgctggaac acgcctacag caaagacggc    1260
ggcctggcgt tgctctacgg taactttgcg gaaaacggct gcatcgtgaa aacggcaggc    1320
gtcgatgaca gcatcctcaa attcaccggc ccggcgaaag tgtacgaaag ccaggacgat    1380
gcggtagaag cgattctcgg cggtaaagtt gtcgccggag atgtggtagt aattcgctat    1440
gaaggcccga aaggcggtcc ggggatgcag gaaatgctct acccaaccag cttcctgaaa    1500
tcaatgggtc tcggcaaagc ctgtgcgctg atcaccgacg tcgtttctc tggtggcacc    1560 tctggtcttt ccatcggcca cgtctcaccg gaagcggcaa gcggcggcag cattggcctg    1620
```

-continued

```
attgaagatg gtgacctgat cgctatcgac atcccgaacc gtggcattca gttacaggta    1680
agcgatgccg aactggcggc gcgtcgtgaa gcgcaggacg ctcgaggtga caaagcctgg    1740
acgccgaaaa atcgtgaacg tcaggtctcc tttgccctgc gtgcttatgc cagcctggca    1800
accagcgccg acaaaggcgc ggtgcgcgat aaatcgaaac tggggggtta a             1851
```

```
<210> SEQ ID NO 34
<211> LENGTH: 616
<212> TYPE: PRT
<213> ORGANISM: Escherichia coli

<400> SEQUENCE: 34

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
```

```
                    340             345                 350
Leu Gly Leu Thr Leu Pro Gln Thr Leu Glu Gln Tyr Asp Val Met Leu
            355                 360                 365
Thr Gln Asp Asp Ala Val Lys Asn Met Phe Arg Ala Gly Pro Ala Gly
        370                 375                 380
Ile Arg Thr Thr Gln Ala Phe Ser Gln Asp Cys Arg Trp Asp Thr Leu
385                 390                 395                 400
Asp Asp Asp Arg Ala Asn Gly Cys Ile Arg Ser Leu Glu His Ala Tyr
                405                 410                 415
Ser Lys Asp Gly Gly Leu Ala Val Leu Tyr Gly Asn Phe Ala Glu Asn
            420                 425                 430
Gly Cys Ile Val Lys Thr Ala Gly Val Asp Asp Ser Ile Leu Lys Phe
        435                 440                 445
Thr Gly Pro Ala Lys Val Tyr Glu Ser Gln Asp Asp Ala Val Glu Ala
        450                 455                 460
Ile Leu Gly Gly Lys Val Ala Gly Asp Val Val Ile Arg Tyr
465                 470                 475                 480
Glu Gly Pro Lys Gly Gly Pro Gly Met Gln Glu Met Leu Tyr Pro Thr
                485                 490                 495
Ser Phe Leu Lys Ser Met Gly Leu Gly Lys Ala Cys Ala Leu Ile Thr
            500                 505                 510
Asp Gly Arg Phe Ser Gly Gly Thr Ser Gly Leu Ser Ile Gly His Val
        515                 520                 525
Ser Pro Glu Ala Ala Ser Gly Gly Ser Ile Gly Leu Ile Glu Asp Gly
        530                 535                 540
Asp Leu Ile Ala Ile Asp Ile Pro Asn Arg Gly Ile Gln Leu Gln Val
545                 550                 555                 560
Ser Asp Ala Glu Leu Ala Ala Arg Arg Glu Ala Gln Asp Ala Arg Gly
                565                 570                 575
Asp Lys Ala Trp Thr Pro Lys Asn Arg Glu Arg Gln Val Ser Phe Ala
            580                 585                 590
Leu Arg Ala Tyr Ala Ser Leu Ala Thr Ser Ala Asp Lys Gly Ala Val
        595                 600                 605
Arg Asp Lys Ser Lys Leu Gly Gly
        610                 615

<210> SEQ ID NO 35
<211> LENGTH: 1647
<212> TYPE: DNA
<213> ORGANISM: Lactococcus lactis

<400> SEQUENCE: 35
atgtatactg tggggattac cctgctggat cgcctgcacg aactgggat tgaagaaatt      60 ttcggtgtgc aggcgatta taacctgcag ttcctggacc agattatctc gcacaaagat     120
atgaagtggg tcggtaacgc caacgaactg aacgcgagct atatggcaga tggttatgcc     180
cgtaccaaaa aagctgctgc gtttctgacg acctttggcg ttggcgaact gagcgccgtc     240
aacggactgg caggaagcta cgccgagaac ctgccagttg tcgaaattgt tgggtcgcct     300
acttctaagg ttcagaatga aggcaaattt gtgcaccata ctctggctga tggggatttt     360
aaacatttta tgaaaatgca tgaaccggtt actgcgccc gcacgctgct gacagcagag     420
aatgctacgg ttgagatcga ccgcgtcctg tctgcgctgc tgaaagagcg caagccggta     480
tatatcaatc tgcctgtcga tgttgccgca gcgaaagccg aaaagccgtc gctgccactg     540 aaaaagagaaa acagcaccctc caatacatcg gaccaggaaa ttctgaataa aatccaggaa     600
```

```
tcactgaaga atgcgaagaa accgatcgtc atcaccggac atgagatcat ctcttttggc    660
ctggaaaaaa cggtcacgca gttcatttct aagaccaaac tgcctatcac caccctgaac    720
ttcggcaaat ctagcgtcga tgaagcgctg ccgagttttc tgggtatcta atatggtacc    780
ctgtccgaac cgaacctgaa agaattcgtc gaaagcgcgg actttatcct gatgctgggc    840
gtgaaactga cggatagctc cacaggcgca tttacccacc atctgaacga gaataaaatg    900
atttccctga atatcgacga aggcaaaatc tttaacgagc gcatccagaa cttcgatttt    960
gaatctctga ttagttcgct gctggatctg tccgaaattg agtataaagg taaatatatt   1020
gataaaaaac aggaggattt tgtgccgtct aatgcgctgc tgagtcagga tcgtctgtgg   1080
caagccgtag aaaacctgac acagtctaat gaaacgattg ttgcggaaca gggaacttca   1140
tttttcggcg cctcatccat ttttctgaaa tccaaaagcc atttcattgg ccaaccgctg   1200 tggggggagta ttggttatac ctttccggcg gcgctgggtt cacagattgc agataaggaa   1260
tcacgccatc tgctgtttat tggtgacggc agcctgcagc tgactgtcca ggaactgggg   1320
ctggcgatcc gtgaaaaaat caatccgatt tgctttatca tcaataacga cggctacacc   1380
gtcgaacgcg aaattcatgg accgaatcaa agttacaatg catcccgat gtggaactat   1440 agcaaactgc cggaatcctt tggcgcgaca gaggatcgcg tggtgagtaa aattgtgcgt   1500
acggaaaacg aatttgtgtc ggttatgaaa gaagcgcagg ctgacccgaa tcgcatgtat   1560
tggattgaac tgatcctggc aaaagaaggc gcaccgaaag ttctgaaaaa gatggggaaa   1620
ctgtttgcgg agcaaaataa aagctaa                                        1647

<210> SEQ ID NO 36
<211> LENGTH: 548
<212> TYPE: PRT
<213> ORGANISM: Lactococcus lactis

<400> SEQUENCE: 36

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190
```

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
            530                 535                 540

Gln Asn Lys Ser
545

<210> SEQ ID NO 37
<211> LENGTH: 1164
<212> TYPE: DNA
<213> ORGANISM: Escherichia coli

<400> SEQUENCE: 37
atgaacaact taatctgca caccccaacc cgcattctgt ttggtaaagg cgcaatcgct     60

-continued

| | |
|---|---|
| ggtttacgcg aacaaattcc tcacgatgct cgcgtattga ttacctacgg cggcggcagc | 120 |
| gtgaaaaaaa ccggcgttct cgatcaagtt ctggatgccc tgaaaggcat ggacgtgctg | 180 |
| gaatttggcg gtattgagcc aaacccggct tatgaaacgc tgatgaacgc cgtgaaactg | 240 |
| gttcgcgaac agaaagtgac tttcctgctg gcggttggcg gcggttctgt actggacggc | 300 |
| accaaattta tcgccgcagc ggctaactat ccggaaaata tcgatccgtg gcacattctg | 360 |
| caaacgggcg gtaaagagat taaaagcgcc atcccgatgg gctgtgtgct gacgctgcca | 420 |
| gcaaccggtt cagaatccaa cgcaggcgcg gtgatctccc gtaaaaccac aggcgacaag | 480 |
| caggcgttcc attctgccca tgttcagccg gtatttgccg tgctcgatcc ggtttatacc | 540 |
| tacaccctgc cgccgcgtca ggtggctaac ggcgtagtgg acgcctttgt acacaccgtg | 600 |
| gaacagtatg ttaccaaacc ggttgatgcc aaaattcagg accgtttcgc agaaggcatt | 660 |
| ttgctgacgc taatcgaaga tggtccgaaa gccctgaaag agccagaaaa ctacgatgtg | 720 |
| cgcgccaacg tcatgtgggc ggcgactcag gcgctgaacg gtttgattgg cgctggcgta | 780 |
| ccgcaggact gggcaacgca tatgctgggc cacgaactga ctgcgatgca cggtctggat | 840 |
| cacgcgcaaa cactggctat cgtcctgcct gcactgtgga atgaaaaacg cgataccaag | 900 |
| cgcgctaagc tgctgcaata tgctgaacgc gtctggaaca tcactgaagg ttccgatgat | 960 |
| gagcgtattg acgccgcgat tgccgcaacc cgcaatttct ttgagcaatt aggcgtgccg | 1020 |
| acccacctct ccgactacgg tctggacggc agctccatcc cggctttgct gaaaaaactg | 1080 |
| gaagagcacg gcatgaccca actgggcgaa aatcatgaca ttacgttgga tgtcagccgc | 1140 |
| cgtatatacg aagccgcccg ctaa | 1164 |

<210> SEQ ID NO 38
<211> LENGTH: 387
<212> TYPE: PRT
<213> ORGANISM: Escherichia coli

<400> SEQUENCE: 38

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Gly Gly Gly Ser Val Lys Lys Thr Gly Val Leu Asp
            35                  40                  45

Gln Val Leu Asp Ala Leu Lys Gly Met Asp Val Leu Glu Phe Gly Gly
        50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val

```
                180              185             190
Val Asp Ala Phe Val His Thr Val Glu Gln Tyr Val Thr Lys Pro Val
            195                 200             205
Asp Ala Lys Ile Gln Asp Arg Phe Ala Glu Gly Ile Leu Leu Thr Leu
    210                 215             220
Ile Glu Asp Gly Pro Lys Ala Leu Lys Glu Pro Glu Asn Tyr Asp Val
225             230                 235                     240
Arg Ala Asn Val Met Trp Ala Ala Thr Gln Ala Leu Asn Gly Leu Ile
                245                 250                 255
Gly Ala Gly Val Pro Gln Asp Trp Ala Thr His Met Leu Gly His Glu
            260                 265                 270
Leu Thr Ala Met His Gly Leu Asp His Ala Gln Thr Leu Ala Ile Val
            275                 280              285
Leu Pro Ala Leu Trp Asn Glu Lys Arg Asp Thr Lys Arg Ala Lys Leu
        290                 295             300
Leu Gln Tyr Ala Glu Arg Val Trp Asn Ile Thr Glu Gly Ser Asp Asp
305             310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
            340                 345                 350
Ile Pro Ala Leu Leu Lys Lys Leu Glu Glu His Gly Met Thr Gln Leu
            355                 360                 365
Gly Glu Asn His Asp Ile Thr Leu Asp Val Ser Arg Arg Ile Tyr Glu
        370                 375             380
Ala Ala Arg
385

<210> SEQ ID NO 39
<211> LENGTH: 1197
<212> TYPE: DNA
<213> ORGANISM: Saccharomyces cerevisiae

<400> SEQUENCE: 39
atgtctcaga acgtttacat tgtatcgact gccagaaccc caattggttc attccagggt      60
tctctatcct ccaagacagc agtggaattg ggtgctgttg cttttaaaagg cgccttggct    120 aaggttccag aattggatgc atccaaggat tttgacgaaa ttattttttgg taacgttctt    180 tctgccaatt tgggccaagc tccggccaga caagttgctt tggctgccgg tttgagtaat    240
catatcgttg caagcacagt taacaaggtc tgtgcatccg ctatgaaggc aatcattttg    300
ggtgctcaat ccatcaaatg tggtaatgct gatgttgtcg tagctggtgg ttgtgaatct    360
atgactaacg caccatacta catgccagca gcccgtgcgg gtgccaaatt tggccaaact    420
gttcttgttg atggtgtcga agagatgggt tgaacgatgc gtacgatggg tctagccatg    480
ggtgtacacg cagaaaagtg tgcccgtgat tgggatatta ctagagaaca acaagacaat    540
tttgccatcg aatcctacca aaatctcaa aatctcaaa aggaaggtaa attcgacaat    600
gaaattgtac ctgttaccat taagggattt agaggtaagc ctgatactca agtcacgaag    660
gacgaggaac ctgctagatt acacgttgaa aaattgagat ctgcaaggac tgttttccaa    720
aaagaaaacg gtactgttac tgccgctaac gcttctccaa tcaacgatgg tgctgcagcc    780
gtcatcttgg tttccgaaaa agttttgaag gaaagaatt tgaagccttt ggctattatc    840
aaaggttggg gtgaggccgc tcatcaacca gctgattta catgggctcc atctcttgca    900
gttccaaagg ctttgaaaca tgctggcatc gaagacatca attctgttga ttactttgaa    960
```

```
ttcaatgaag cctttcggt tgtcggtttg gtgaacacta agattttgaa gctagaccca   1020
tctaaggtta atgtatatgg tggtgctgtt gctctaggtc acccattggg ttgttctggt   1080
gctagagtgg ttgttacact gctatccatc ttacagcaag aaggaggtaa gatcggtgtt   1140
gccgccattt gtaatggtgg tggtggtgct tcctctattg tcattgaaaa gatatga     1197
```

<210> SEQ ID NO 40
<211> LENGTH: 398
<212> TYPE: PRT
<213> ORGANISM: Saccharomyces cerevisiae

<400> SEQUENCE: 40

```
Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
                20                  25                  30

Val Ala Leu Lys Gly Ala Leu Ala Lys Val Pro Glu Leu Asp Ala Ser
            35                  40                  45

Lys Asp Phe Asp Glu Ile Ile Phe Gly Asn Val Leu Ser Ala Asn Leu
        50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335
```

```
Lys Leu Asp Pro Ser Lys Val Asn Val Tyr Gly Gly Ala Val Ala Leu
            340                 345                 350

Gly His Pro Leu Gly Cys Ser Gly Ala Arg Val Val Thr Leu Leu
        355                 360                 365

Ser Ile Leu Gln Gln Glu Gly Gly Lys Ile Gly Val Ala Ala Ile Cys
370                 375                 380

Asn Gly Gly Gly Gly Ala Ser Ser Ile Val Ile Glu Lys Ile
385                 390                 395

<210> SEQ ID NO 41
<211> LENGTH: 1713
<212> TYPE: DNA
<213> ORGANISM: Bacillus subtilis

<400> SEQUENCE: 41
```

| | | |
|---|---|---|
| ttgacaaaag caacaaaaga acaaaaatcc cttgtgaaaa acagaggggc ggagcttgtt | 60 |
| gttgattgct tagtggagca aggtgtcaca catgtatttg cattccagg tgcaaaaatt | 120 |
| gatgcggtat ttgacgcttt acaagataaa ggacctgaaa ttatcgttgc ccggcacgaa | 180 |
| caaaacgcag cattcatggc ccaagcagtc ggccgtttaa ctggaaaacc gggagtcgtg | 240 |
| ttagtcacat caggaccggg tgcctctaac ttggcaacag gcctgctgac agcgaacact | 300 |
| gaaggagacc ctgtcgttgc gcttgctgga aacgtgatcc gtgcagatcg tttaaaacgg | 360 |
| acacatcaat ctttggataa tgcggcgcta ttccagccga ttacaaaata cagtgtagaa | 420 |
| gttcaagatg taaaaatat accggaagct gttacaaatg catttaggat agcgtcagca | 480 |
| gggcaggctg gggccgcttt tgtgagcttt ccgcaagatg ttgtgaatga agtcacaaat | 540 |
| acgaaaaacg tgcgtgctgt tgcagcgcca aaactcggtc ctgcagcaga tgatgcaatc | 600 |
| agtgcggcca tagcaaaaat ccaaacagca aaacttcctg tcgttttggt cggcatgaaa | 660 |
| ggcggaagac cggaagcaat taagcgggtt cgcaagcttt tgaaaaaggt tcagcttcca | 720 |
| tttgttgaaa catatcaagc tgccggtacc ctttctagag atttagagga tcaatatttt | 780 |
| ggccgtatcg gtttgttccg caaccagcct ggcgatttac tgctagagca ggcagatgtt | 840 |
| gttctgacga tcggctatga cccgattgaa tatgatccga attctggaa tatcaatgga | 900 |
| gaccggacaa ttatccattt agacgagatt atcgctgaca ttgatcatgc ttaccagcct | 960 |
| gatcttgaat tgatcggtga cattccgtcc acgatcaatc atatcgaaca cgatgctgtg | 1020 |
| aaagtggaat ttgcagagcg tgagcagaaa atcctttctg atttaaaaca atatatgcat | 1080 |
| gaaggtgagc aggtgcctgc agattggaaa tcagacagag cgcaccctct tgaaatcgtt | 1140 |
| aaagagttgc gtaatgcagt cgatgatcat gttacagtaa cttgcgatat cggttcgcac | 1200 |
| gccatttgga tgtcacgtta tttccgcagc tacgagccgt taacattaat gatcagtaac | 1260 |
| ggtatgcaaa cactcggcgt tgcgcttcct tgggcaatcg gcgcttcatt ggtgaaaccg | 1320 |
| ggagaaaaag tggtttctgt ctctggtgac ggcggtttct tattctcagc aatgaatta | 1380 |
| gagacagcag ttcgactaaa agcaccaatt gtacacattg tatggaacga cagcacatat | 1440 |
| gacatggttg cattccagca attgaaaaaa tataaccgta catctgcggt cgatttcgga | 1500 |
| aatatcgata tcgtgaaata tgcggaaagc ttcggagcaa ctggcttgcg cgtagaatca | 1560 |
| ccagaccagc tggcagatgt tctgcgtcaa ggcatgaacg ctgaaggtcc tgtcatcatc | 1620 |
| gatgtcccgg ttgactacag tgataacatt aatttagcaa gtgacaagct tccgaaagaa | 1680 |
| ttcggggaac tcatgaaaac gaaagctctc tag | 1713 |

```
<210> SEQ ID NO 42
```

<211> LENGTH: 570
<212> TYPE: PRT
<213> ORGANISM: Bacillus subtilis

<400> SEQUENCE: 42

```
Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Val Thr His Val
            20                  25                  30

Phe Gly Ile Pro Gly Ala Lys Ile Asp Ala Val Phe Asp Ala Leu Gln
        35                  40                  45

Asp Lys Gly Pro Glu Ile Ile Val Ala Arg His Glu Gln Asn Ala Ala
50                  55                  60

Phe Met Ala Gln Ala Val Gly Arg Leu Thr Gly Lys Pro Gly Val Val
65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
            100                 105                 110

Ile Arg Ala Asp Arg Leu Lys Arg Thr His Gln Ser Leu Asp Asn Ala
        115                 120                 125

Ala Leu Phe Gln Pro Ile Thr Lys Tyr Ser Val Glu Val Gln Asp Val
    130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                165                 170                 175

Glu Val Thr Asn Thr Lys Asn Val Arg Ala Val Ala Ala Pro Lys Leu
            180                 185                 190

Gly Pro Ala Ala Asp Asp Ala Ile Ser Ala Ala Ile Ala Lys Ile Gln
        195                 200                 205

Thr Ala Lys Leu Pro Val Val Leu Val Gly Met Lys Gly Gly Arg Pro
    210                 215                 220

Glu Ala Ile Lys Ala Val Arg Lys Leu Leu Lys Lys Val Gln Leu Pro
225                 230                 235                 240

Phe Val Glu Thr Tyr Gln Ala Ala Gly Thr Leu Ser Arg Asp Leu Glu
                245                 250                 255

Asp Gln Tyr Phe Gly Arg Ile Gly Leu Phe Arg Asn Gln Pro Gly Asp
            260                 265                 270

Leu Leu Leu Glu Gln Ala Asp Val Val Leu Thr Ile Gly Tyr Asp Pro
        275                 280                 285

Ile Glu Tyr Asp Pro Lys Phe Trp Asn Ile Asn Gly Asp Arg Thr Ile
290                 295                 300

Ile His Leu Asp Glu Ile Ile Ala Asp Ile Asp His Ala Tyr Gln Pro
305                 310                 315                 320

Asp Leu Glu Leu Ile Gly Asp Ile Pro Ser Thr Ile Asn His Ile Glu
                325                 330                 335

His Asp Ala Val Lys Val Glu Phe Ala Glu Arg Glu Gln Lys Ile Leu
            340                 345                 350

Ser Asp Leu Lys Gln Tyr Met His Glu Gly Glu Gln Val Pro Ala Asp
        355                 360                 365

Trp Lys Ser Asp Arg Ala His Pro Leu Glu Ile Val Lys Glu Leu Arg
    370                 375                 380

Asn Ala Val Asp Asp His Val Thr Val Thr Cys Asp Ile Gly Ser His
385                 390                 395                 400
```

```
Ala Ile Trp Met Ser Arg Tyr Phe Arg Ser Tyr Glu Pro Leu Thr Leu
            405                 410                 415

Met Ile Ser Asn Gly Met Gln Thr Leu Gly Val Ala Leu Pro Trp Ala
        420                 425                 430

Ile Gly Ala Ser Leu Val Lys Pro Gly Glu Lys Val Val Ser Val Ser
            435                 440                 445

Gly Asp Gly Gly Phe Leu Phe Ser Ala Met Glu Leu Glu Thr Ala Val
        450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
            485                 490                 495

Val Asp Phe Gly Asn Ile Asp Ile Val Lys Tyr Ala Glu Ser Phe Gly
        500                 505                 510

Ala Thr Gly Leu Arg Val Glu Ser Pro Asp Gln Leu Ala Asp Val Leu
            515                 520                 525

Arg Gln Gly Met Asn Ala Glu Gly Pro Val Ile Ile Asp Val Pro Val
        530                 535                 540

Asp Tyr Ser Asp Asn Ile Asn Leu Ala Ser Asp Lys Leu Pro Lys Glu
545                 550                 555                 560

Phe Gly Glu Leu Met Lys Thr Lys Ala Leu
            565                 570

<210> SEQ ID NO 43
<211> LENGTH: 1188
<212> TYPE: DNA
<213> ORGANISM: Saccharomyces cerevisiae

<400> SEQUENCE: 43
atgttgagaa ctcaagccgc cagattgatc tgcaactccc gtgtcatcac tgctaagaga      60
acctttgctt tggccacccg tgctgctgct tacagcagac cagctgcccg tttcgttaag     120
ccaatgatca ctacccgtgg tttgaagcaa atcaacttcg gtggtactgt tgaaaccgtc     180
tacgaaagag ctgactggcc aagagaaaag ttgttggact acttcaagaa cgacactttt     240
gctttgatcg gttacggttc ccaaggttac ggtcaaggtt tgaacttgag agacaacggt     300
ttgaacgtta tcattggtgt ccgtaaagat ggtgcttctt ggaaggctgc catcgaagac     360
ggttgggttc aggcaagaa cttgttcact gttgaagatg ctatcaagag aggtagttac     420
gttatgaact tgttgtccga tgccgctcaa tcagaaacct ggcctgctat caagccattg     480
ttgaccaagg gtaagacttt gtacttctcc cacggtttct ccccagtctt caaggacttg     540
actcacgttg aaccaccaaa ggacttagat gttatcttgg ttgctccaaa gggttccggt     600
agaactgtca gatctttgtt caaggaaggt cgtggtatta actcttctta cgccgtctgg     660
aacgatgtca ccgtaaggc tcacgaaaag gcccaagctt tggccgttgc cattggttcc     720
ggttacgttt accaaaccac tttcgaaaga gaagtcaact ctgacttgta cggtgaaaga     780
ggttgtttaa tgggtggtat ccacggtatg ttcttggctc aatacgacgt cttgagagaa     840
aacggtcact cccccatctga agctttcaac gaaaccgtcg aagaagctac ccaatctcta     900
tacccattga tcggtaagta cggtatggat tacatgtacg atgcttgttc caccaccgcc     960
agaagaggtg ctttggactg gtacccaatc ttcaagaatg ctttgaagcc tgttttccaa    1020
gacttgtacg aatctaccaa gaacggtacc gaaaccaaga gatctttgga attcaactct    1080
caacctgact acagagaaaa gctagaaaag gaattagaca ccatcagaaa catggaaatc    1140
```
tggaaggttg gtaaggaagt cagaaagttg agaccagaaa accaataa            1188

<210> SEQ ID NO 44
<211> LENGTH: 395
<212> TYPE: PRT
<213> ORGANISM: Saccharomyces cerevisiae

<400> SEQUENCE: 44

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly

```
                370                 375                 380
Lys Glu Val Arg Lys Leu Arg Pro Glu Asn Gln
385                 390                 395
```

<210> SEQ ID NO 45
<211> LENGTH: 1029
<212> TYPE: DNA
<213> ORGANISM: Bacillus subtilis

<400> SEQUENCE: 45

| | | | | |
|---|---|---|---|---|
| atggtaaaag tatattataa cggtgatatc aaagagaacg tattggctgg aaaaacagta | 60 |
| gcggttatcg ggtacggttc gcaaggccac gcacatgccc tgaaccttaa agaaagcgga | 120 |
| gtagacgtga tcgtcggtgt tagacaagga aaatctttca ctcaagccca agaagacgga | 180 |
| cataaagtat tttcagtaaa agaagcggca gcccaagccg aaatcatcat ggttctgctt | 240 |
| ccggatgagc agcagcaaaa agtatacgaa gctgaaatca agatgaatt gacagcagga | 300 |
| aaatcattag tattcgctca tggatttaac gtgcatttcc atcaaattgt tcctccggcg | 360 |
| gatgtagatg tattcttagt ggcccctaaa ggcccgggac acttggtaag aagaacatat | 420 |
| gagcaaggag ctggcgtacc tgcattgttc gcaatctatc aagatgtgac tggagaagca | 480 |
| agagacaaag ccctcgctta tgctaaagga atcggcggcg caagagcggg cgtattagaa | 540 |
| acgcatttta agaagaaac agaaacagat ttgttcggtg agcaagcagt tctttgcggc | 600 |
| ggattaagcg cgcttgtcaa agccggattt gaaaccttaa ctgaagcagg ttatcagcct | 660 |
| gaacttgcat acttcgagtg tcttcatgag ctgaaattaa tcgtagacct tatgtacgaa | 720 |
| gaaggacttg caggaatgag atattcaatc tctgacacag cacagtgggg agatttcgta | 780 |
| tcaggcccctc gcgttgtgga cgccaaagta aaagaatcta tgaaagaagt attaaaagat | 840 |
| atccaaaacg gtacattcgc aaaagagtgg atcgtcgaaa accaagtaaa ccgtcctcgt | 900 |
| ttcaacgcta tcaatgcaag cgagaacgaa catcaaatcg aagtagtggg aagaaagctt | 960 |
| cgtgaaatga tgccgtttgt gaaacaaggc aagaagaagg aagcggtggt ctccgttgcg | 1020 |
| caaaattaa | 1029 |

<210> SEQ ID NO 46
<211> LENGTH: 342
<212> TYPE: PRT
<213> ORGANISM: Bacillus subtilis

<400> SEQUENCE: 46

```
Met Val Lys Val Tyr Tyr Asn Gly Asp Ile Lys Glu Asn Val Leu Ala
1               5                   10                  15
Gly Lys Thr Val Ala Val Ile Gly Tyr Gly Ser Gln Gly His Ala His
            20                  25                  30
Ala Leu Asn Leu Lys Glu Ser Gly Val Asp Val Ile Gly Val Arg
        35                  40                  45
Gln Gly Lys Ser Phe Thr Gln Ala Gln Glu Asp Gly His Lys Val Phe
    50                  55                  60
Ser Val Lys Glu Ala Ala Ala Gln Ala Glu Ile Ile Met Val Leu Leu
65                  70                  75                  80
Pro Asp Glu Gln Gln Gln Lys Val Tyr Glu Ala Glu Ile Lys Asp Glu
                85                  90                  95
Leu Thr Ala Gly Lys Ser Leu Val Phe Ala His Gly Phe Asn Val His
            100                 105                 110
Phe His Gln Ile Val Pro Pro Ala Asp Val Asp Val Phe Leu Val Ala
        115                 120                 125
```

```
Pro Lys Gly Pro Gly His Leu Val Arg Arg Thr Tyr Glu Gln Gly Ala
    130                 135                 140
Gly Val Pro Ala Leu Phe Ala Ile Tyr Gln Asp Val Thr Gly Glu Ala
145                 150                 155                 160
Arg Asp Lys Ala Leu Ala Tyr Ala Lys Gly Ile Gly Gly Ala Arg Ala
                165                 170                 175
Gly Val Leu Glu Thr Thr Phe Lys Glu Thr Glu Thr Asp Leu Phe
                180                 185                 190
Gly Glu Gln Ala Val Leu Cys Gly Gly Leu Ser Ala Leu Val Lys Ala
                195                 200                 205
Gly Phe Glu Thr Leu Thr Glu Ala Gly Tyr Gln Pro Glu Leu Ala Tyr
    210                 215                 220
Phe Glu Cys Leu His Glu Leu Lys Leu Ile Val Asp Leu Met Tyr Glu
225                 230                 235                 240
Glu Gly Leu Ala Gly Met Arg Tyr Ser Ile Ser Asp Thr Ala Gln Trp
                245                 250                 255
Gly Asp Phe Val Ser Gly Pro Arg Val Val Asp Ala Lys Val Lys Glu
                260                 265                 270
Ser Met Lys Glu Val Leu Lys Asp Ile Gln Asn Gly Thr Phe Ala Lys
            275                 280                 285
Glu Trp Ile Val Glu Asn Gln Val Asn Arg Pro Arg Phe Asn Ala Ile
    290                 295                 300
Asn Ala Ser Glu Asn Glu His Gln Ile Glu Val Val Gly Arg Lys Leu
305                 310                 315                 320
Arg Glu Met Met Pro Phe Val Lys Gln Gly Lys Lys Glu Ala Val
                325                 330                 335
Val Ser Val Ala Gln Asn
            340

<210> SEQ ID NO 47
<211> LENGTH: 1758
<212> TYPE: DNA
<213> ORGANISM: Saccharomyces cerevisiae

<400> SEQUENCE: 47
atgggcttgt taacgaaagt tgctacatct agacaattct ctacaacgag atgcgttgca      60
aagaagctca acaagtactc gtatatcatc actgaaccta agggccaagg tgcgtcccag     120
gccatgcttt atgccaccgg tttcaagaag gaagatttca agaagcctca agtcgggtt      180 ggttcctgtt ggtggtccgg taacccatgt aacatgcatc tattggactt gaataacaga     240
tgttctcaat ccattgaaaa agcgggtttg aaagctatgc agttcaacac catcggtgtt     300
tcagacggta tctctatggg tactaaaggt atgagatact cgttacaaag tagagaaatc     360
attgcagact cctttgaaac catcatgatg gcacaacact acgatgctaa catcgccatc     420
ccatcatgtg acaaaaacat gcccggtgtc atgatggcca tgggtagaca taacagacct     480
tccatcatgg tatatggtgg tactatcttg cccggtcatc caacatgtgg ttcttcgaag     540
atctctaaaa acatcgatat cgtctctgcg ttccaatcct acggtgaata tatttccaag     600
caattcactg aagaagaaag agaagatgtt gtgaacatg catgcccagg tcctggttct     660
tgtggtggta tgtatactgc caacacaatg gcttctgccg ctgaagtgct aggttttgacc    720 attccaaaact cctcttcctt cccagccgtt tccaaggaga agttagctga gtgtgacaac    780
attggtgaat acatcaagaa gacaatggaa ttgggtattt tacctcgtga tatcctcaca     840
aaagaggctt tgaaaacgc cattacttat gtcgttgcaa ccggtgggtc cactaatgct     900
```

```
gttttgcatt tggtggctgt tgctcactct gcgggtgtca agttgtcacc agatgatttc     960
caaagaatca gtgatactac accattgatc ggtgacttca aaccttctgg taaatacgtc    1020
atggccgatt tgattaacgt tggtggtacc caatctgtga ttaagtatct atatgaaaac    1080
aacatgttgc acggtaacac aatgactgtt accggtgaca ctttggcaga acgtgcaaag    1140
aaagcaccaa gcctacctga aggacaagag attattaagc cactctccca cccaatcaag    1200
gccaacggtc acttgcaaat tctgtacggt tcattggcac aggtggagc tgtgggtaaa    1260 attaccggta aggaaggtac ttacttcaag ggtagagcac gtgtgttcga agaggaaggt    1320
gcctttattg aagccttgga agaggtgaa atcaagaagg gtgaaaaaac cgttgttgtt    1380
atcagatatg aaggtccaag aggtgcacca ggtatgcctg aaatgctaaa gccttcctct    1440
gctctgatgg gttacggttt gggtaaagat gttgcattgt tgactgatgg tagattctct    1500
ggtggttctc acgggttctt aatcggccac attgttcccg aagccgctga aggtggtcct    1560
atcgggttgg tcagagacgg cgatgagatt atcattgatg ctgataataa caagattgac    1620
ctattagtct ctgataagga aatggctcaa cgtaaacaaa gttgggttgc acctccacct    1680
cgttacacaa gaggtactct atccaagtat gctaagttgg tttccaacgc ttccaacggt    1740
tgtgttttag atgcttga                                                  1758

<210> SEQ ID NO 48
<211> LENGTH: 585
<212> TYPE: PRT
<213> ORGANISM: Saccharomyces cerevisiae

<400> SEQUENCE: 48

Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
                20                  25                  30

Pro Lys Gly Gln Gly Ala Ser Gln Ala Met Leu Tyr Ala Thr Gly Phe
            35                  40                  45

Lys Lys Glu Asp Phe Lys Lys Pro Gln Val Gly Val Gly Ser Cys Trp
        50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
    130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
        195                 200                 205

Asp Val Val Glu His Ala Cys Pro Gly Pro Gly Ser Cys Gly Gly Met
    210                 215                 220
```

Tyr Thr Ala Asn Thr Met Ala Ser Ala Ala Glu Val Leu Gly Leu Thr
225                 230                 235                 240

Ile Pro Asn Ser Ser Ser Phe Pro Ala Val Ser Lys Glu Lys Leu Ala
            245                 250                 255

Glu Cys Asp Asn Ile Gly Glu Tyr Ile Lys Lys Thr Met Glu Leu Gly
                260                 265                 270

Ile Leu Pro Arg Asp Ile Leu Thr Lys Glu Ala Phe Glu Asn Ala Ile
            275                 280                 285

Thr Tyr Val Val Ala Thr Gly Gly Ser Thr Asn Ala Val Leu His Leu
        290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
                340                 345                 350

Val Ile Lys Tyr Leu Tyr Glu Asn Asn Met Leu His Gly Asn Thr Met
        355                 360                 365

Thr Val Thr Gly Asp Thr Leu Ala Glu Arg Ala Lys Lys Ala Pro Ser
370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
                420                 425                 430

Ala Arg Val Phe Glu Glu Glu Gly Ala Phe Ile Glu Ala Leu Glu Arg
            435                 440                 445

Gly Glu Ile Lys Lys Gly Glu Lys Thr Val Val Ile Arg Tyr Glu
450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
            500                 505                 510

Pro Glu Ala Ala Glu Gly Gly Pro Ile Gly Leu Val Arg Asp Gly Asp
                515                 520                 525

Glu Ile Ile Ile Asp Ala Asp Asn Asn Lys Ile Asp Leu Leu Val Ser
530                 535                 540

Asp Lys Glu Met Ala Gln Arg Lys Gln Ser Trp Val Ala Pro Pro Pro
545                 550                 555                 560

Arg Tyr Thr Arg Gly Thr Leu Ser Lys Tyr Ala Lys Leu Val Ser Asn
                565                 570                 575

Ala Ser Asn Gly Cys Val Leu Asp Ala
            580                 585

<210> SEQ ID NO 49
<211> LENGTH: 2007
<212> TYPE: DNA
<213> ORGANISM: Saccharomyces cerevisiae

<400> SEQUENCE: 49
atggaagaca agtttgctaa cctcagtctc catgagaaaa ctggtaagtc atctatccaa      60

```
ttaaacgagc aaacaggctc agataatggc tctgctgtca agagaacatc ttcgacgtcc    120
tcgcactaca ataacatcaa cgctgacctt catgctcgtg taaaagcttt tcaagaacaa    180
cgtgcattga aaaggtctgc cagcgtgggc agtaatcaaa gcgagcaaga caaaggcagt    240
tcacaatcac ctaaacatat tcagcagatt gttaataagc cattgccgcc tcttcccgta    300
gcaggaagtt ctaaggtttc acaaagaatg agtagccaag tcgtgcaagc gtcctccaag    360
agcactctta agaacgttct ggacaatcaa gaaacacaaa acattaccga cgtaaatatt    420
aacatcgata caaccaaaat taccgccaca acaattggtg taaatactgg cctacctgct    480
actgacatta cgccgtcagt ttctaatact gcatcagcaa cacataaggc gcaattgctg    540
aatcctaaca aagggcacc aagaaggccg ctttctaccc agcaccctac aagaccaaat    600
gttgccccgc ataaggcccc tgctataatc aacacaccaa aacaaagttt aagtgcccgt    660
cgagggctca aattaccacc aggaggaatg tcattaaaaa tgcccactaa acagctcaa    720 cagccgcagc agtttgcccc aagcccttca aacaaaaaac atatagaaac cttatcaaac    780
agcaaagttg ttgaagggaa aagatcgaat ccgggttctt tgataaatgg tgtgcaaagc    840
acatccacct catcaagtat cgaaggccca catgacactg taggcactac acccagaact    900
ggaaacagca acaactcttc aaattctggt agtagtggtg gtggtggtct tttcgcaaat    960
ttctcgaaat acgtggatat caaatccggc tctttgaatt ttgcaggcaa actatcgcta    1020
tcctctaaag gaatagattt cagcaatggt tctagttcga gaattacatt ggacgaacta    1080 gaattttttgg atgaactggg tcatggtaac tatggtaacg tctcaaaggt actgcataag    1140
cccacaaatg ttattatggc gacgaaggaa gtccgtttgg agctagatga ggctaaattt    1200
agacaaattt taatgaact agaagttttg cataaatgca attctcccta tattgtggat    1260
ttttatggtg cattctttat tgagggcgcc gtctacatgt gtatgaaata catggatggt    1320
ggttccttgg ataaaatata cgacgaatca tctgaaatcg gcggcattga tgaacctcag    1380
ctagcgttta ttgccaatgc tgtcattcat ggactaaaag aactcaaaga gcagcataat    1440
atcatacaca gagatgtcaa accaacaaat atttttatgtt cagccaacca aggcaccgta    1500
aagctgtgcg atttcggtgt ttctggtaat ttggtggcat ctttagcgaa gactaatatt    1560
ggttgtcagt catacatggc acctgaacga atcaaatcgt tgaatccaga tagagccacc    1620
tataccgtac agtcagacat ctggtcttta ggtttaagca ttctggaaat ggcactaggt    1680
agatatccgt atccaccaga aacatacgac aacatttttct ctcaattgag cgctattgtt    1740
gatgggccgc caccgagatt accttcagat aaattcagtt ctgacgcaca agattttgtt    1800
tctttatgtc tacaaaagat tccggaaaga agacctacat acgcagcttt aacagagcat    1860
ccttggttag taaaatacag aaaccaggat gtccacatga gtgagtatat cactgaacga    1920
ttagaaaggc gcaacaaaat cttacgggaa cgtggtgaga atggtttatc taaaaatgta    1980
ccggcattac atatgggtgg tttatag                                       2007
```

<210> SEQ ID NO 50
<211> LENGTH: 668
<212> TYPE: PRT
<213> ORGANISM: Saccharomyces cerevisiae

<400> SEQUENCE: 50

```
Met Glu Asp Lys Phe Ala Asn Leu Ser Leu His Glu Lys Thr Gly Lys
1               5                   10                  15

Ser Ser Ile Gln Leu Asn Glu Gln Thr Gly Ser Asp Asn Gly Ser Ala
            20                  25                  30
```

-continued

```
Val Lys Arg Thr Ser Ser Thr Ser Ser His Tyr Asn Asn Ile Asn Ala
         35                  40                  45

Asp Leu His Ala Arg Val Lys Ala Phe Gln Glu Gln Arg Ala Leu Lys
 50                  55                  60

Arg Ser Ala Ser Val Gly Ser Asn Gln Ser Glu Gln Asp Lys Gly Ser
 65                  70                  75                  80

Ser Gln Ser Pro Lys His Ile Gln Gln Ile Val Asn Lys Pro Leu Pro
                 85                  90                  95

Pro Leu Pro Val Ala Gly Ser Ser Lys Val Ser Gln Arg Met Ser Ser
                100                 105                 110

Gln Val Val Gln Ala Ser Ser Lys Ser Thr Leu Lys Asn Val Leu Asp
            115                 120                 125

Asn Gln Glu Thr Gln Asn Ile Thr Asp Val Asn Ile Asn Ile Asp Thr
130                 135                 140

Thr Lys Ile Thr Ala Thr Thr Ile Gly Val Asn Thr Gly Leu Pro Ala
145                 150                 155                 160

Thr Asp Ile Thr Pro Ser Val Ser Asn Thr Ala Ser Ala Thr His Lys
                165                 170                 175

Ala Gln Leu Leu Asn Pro Asn Arg Arg Ala Pro Arg Arg Pro Leu Ser
            180                 185                 190

Thr Gln His Pro Thr Arg Pro Asn Val Ala Pro His Lys Ala Pro Ala
            195                 200                 205

Ile Ile Asn Thr Pro Lys Gln Ser Leu Ser Ala Arg Arg Gly Leu Lys
        210                 215                 220

Leu Pro Pro Gly Gly Met Ser Leu Lys Met Pro Thr Lys Thr Ala Gln
225                 230                 235                 240

Gln Pro Gln Gln Phe Ala Pro Ser Pro Ser Asn Lys Lys His Ile Glu
                245                 250                 255

Thr Leu Ser Asn Ser Lys Val Val Glu Gly Lys Arg Ser Asn Pro Gly
            260                 265                 270

Ser Leu Ile Asn Gly Val Gln Ser Thr Ser Thr Ser Ser Ile Glu
        275                 280                 285

Gly Pro His Asp Thr Val Gly Thr Thr Pro Arg Thr Gly Asn Ser Asn
    290                 295                 300

Asn Ser Ser Asn Ser Gly Ser Ser Gly Gly Gly Leu Phe Ala Asn
305                 310                 315                 320

Phe Ser Lys Tyr Val Asp Ile Lys Ser Gly Ser Leu Asn Phe Ala Gly
                325                 330                 335

Lys Leu Ser Leu Ser Ser Lys Gly Ile Asp Phe Ser Asn Gly Ser Ser
            340                 345                 350

Ser Arg Ile Thr Leu Asp Glu Leu Glu Phe Leu Asp Glu Leu Gly His
            355                 360                 365

Gly Asn Tyr Gly Asn Val Ser Lys Val Leu His Lys Pro Thr Asn Val
    370                 375                 380

Ile Met Ala Thr Lys Glu Val Arg Leu Glu Leu Asp Glu Ala Lys Phe
385                 390                 395                 400

Arg Gln Ile Leu Met Glu Leu Glu Val Leu His Lys Cys Asn Ser Pro
                405                 410                 415

Tyr Ile Val Asp Phe Tyr Gly Ala Phe Phe Ile Glu Gly Ala Val Tyr
            420                 425                 430

Met Cys Met Glu Tyr Met Asp Gly Gly Ser Leu Asp Lys Ile Tyr Asp
            435                 440                 445

Glu Ser Ser Glu Ile Gly Gly Ile Asp Glu Pro Gln Leu Ala Phe Ile
450                 455                 460
```

```
Ala Asn Ala Val Ile His Gly Leu Lys Glu Leu Lys Glu Gln His Asn
465                 470                 475                 480

Ile Ile His Arg Asp Val Lys Pro Thr Asn Ile Leu Cys Ser Ala Asn
            485                 490                 495

Gln Gly Thr Val Lys Leu Cys Asp Phe Gly Val Ser Gly Asn Leu Val
                500                 505                 510

Ala Ser Leu Ala Lys Thr Asn Ile Gly Cys Gln Ser Tyr Met Ala Pro
        515                 520                 525

Glu Arg Ile Lys Ser Leu Asn Pro Asp Arg Ala Thr Tyr Thr Val Gln
            530                 535                 540

Ser Asp Ile Trp Ser Leu Gly Leu Ser Ile Leu Glu Met Ala Leu Gly
545                 550                 555                 560

Arg Tyr Pro Tyr Pro Pro Glu Thr Tyr Asp Asn Ile Phe Ser Gln Leu
                565                 570                 575

Ser Ala Ile Val Asp Gly Pro Pro Arg Leu Pro Ser Asp Lys Phe
        580                 585                 590

Ser Ser Asp Ala Gln Asp Phe Val Ser Leu Cys Leu Gln Lys Ile Pro
        595                 600                 605

Glu Arg Arg Pro Thr Tyr Ala Ala Leu Thr Glu His Pro Trp Leu Val
            610                 615                 620

Lys Tyr Arg Asn Gln Asp Val His Met Ser Glu Tyr Ile Thr Glu Arg
625                 630                 635                 640

Leu Glu Arg Arg Asn Lys Ile Leu Arg Glu Arg Gly Glu Asn Gly Leu
                645                 650                 655

Ser Lys Asn Val Pro Ala Leu His Met Gly Gly Leu
            660                 665

<210> SEQ ID NO 51
<211> LENGTH: 2034
<212> TYPE: DNA
<213> ORGANISM: Candida glabrata

<400> SEQUENCE: 51
atggagaggg tgcgattgga cagaaagagc agtaatgaca gcaatcatag tctgggagga      60
gaatctacta gcagaagtgg aggatcaggt attggtgttg cccccactag tggcaataat     120
ggtactgtga aaagagctag ttcaatgtca tcaaactaca gtaacataaa tgcctcttta     180
catgcgcgtg tgaaagcatt ccaagaacaa agaggtctac ataggtctag cagtttgggg     240
aaaggagatt cggaagagaa cattggaaac gtaggtacaa gtataaatcc ttctcctagc     300
ctcggatcta tgaaagacga gccagtacca gcgattcaaa aaattgtaaa taaaccacta     360
ccgccattgc cgggtcagaa tagttcctcg cttacaccct cccaggaaac aatcaatatg     420
attagcaatg cttctcaaca ggcaccagat ggtccactca ataatatttc acctgttcca     480
ggatttaagg aagctatggg gggcaatgta agaagaaatg acgggcaaaa tctttatggt     540
tctacaagtc ccgcagtaac agcctcggct cctaatatgc ctgcttttaa tccaaataga     600
aaggcaccaa gacctcccca aattcctcat aatactgtga taccagcaaa acctatgcaa     660
agtctgagtt caagaagagg tctgaaatta ccgcccggtg aatgaaact gaaactacct     720 tcaaaaggtg acgcgccagc atctatgcca agtacagttc ctgcagcttc atcagtgaaa     780
ccggttgttc atcaagaatt tgccgccact ccatcaaata gaatcacat aaagaataat     840 aacggaagca ctgagggtaa aggtcaaat ccaggttcct tagtgaacgc agttcaaact     900
acatctattt catcagctaa tgatcagcag gatacggaag gaactgaacc aaaaagcaac     960
```

```
tctaatggta ctggtctgtt tgcaaacttt cgcgatatg tggatattaa gtcgggctct   1020
ttaaattttg ctggtaagct ttcacttttcc tcaagaggta ttgattttag caatggttct   1080
agttcaagga taacacttga tgagcttcaa tttatagagg aactgggaca tggtaattat   1140
ggtactgtgt caaaagtttt acataagcca aataatgttt tgatggcaat gaaagaagtt   1200
agacttgaat tagatgagtc taaatttagg caaattttaa tggaattaga agtgcttcat   1260
aaatgtaact caccatttat cgtggacttc tatggtgcat ttttttataga gggtgctgtt   1320 tatatgtgca tggaatatat ggatggtgga tcattagata aaatatacga tgaaaacccc   1380
gaaatgggtg gtattgatga gccacaactt gcatttatca ctaacgctgt cattcaaggt   1440
ttgagggagc taaaagaggt tcataacgtg atacatcgag acgtaaagcc aaccaacatt   1500
ctgtgttctg ccaagcaagg aactgtgaaa ttgtgtgatt ttggtgtttc tggtaatctg   1560
gtagcttcct tagcgaagac aaatataggt tgtcaatcat atatggctcc tgagagaata   1620
aaatctctga accctgatag aggaacatat acagtgcagt cagacatatg gtcattgggt   1680
ctaagtatac tagagatggc attaggtaga tatccttatc ctccagaaac attcgataat   1740
atattctcgc aactaagtgc aatcgtagat ggaccacccc ctaaactgcc agcagataag   1800
ttcagtgatg aggcccaaga cttcgtgtcg ttgtgtctgc aaaagatccc tgatagaaga   1860
cccaattatt ctaatctgta tgagcatcca tggctagcaa aatatcgtag catcgacgtc   1920
caaatggggc catacattac taaaagatta gaaatccgga aaagaatact agctgaaaag   1980
ggtgaggacg tcttcacag gacagtacct gcattgcata aaggtggttt gtaa       2034
```

<210> SEQ ID NO 52
<211> LENGTH: 677
<212> TYPE: PRT
<213> ORGANISM: Candida glabrata

<400> SEQUENCE: 52

```
Met Glu Arg Val Arg Leu Asp Arg Lys Ser Ser Asn Asp Ser Asn His
1               5                   10                  15

Ser Leu Gly Gly Glu Ser Thr Ser Arg Ser Gly Gly Ser Gly Ile Gly
            20                  25                  30

Val Ala Pro Thr Ser Gly Asn Asn Gly Thr Val Lys Arg Ala Ser Ser
        35                  40                  45

Met Ser Ser Asn Tyr Ser Asn Ile Asn Ala Ser Leu His Ala Arg Val
    50                  55                  60

Lys Ala Phe Gln Glu Gln Arg Gly Leu His Arg Ser Ser Ser Leu Gly
65                  70                  75                  80

Lys Gly Asp Ser Glu Glu Asn Ile Gly Asn Val Gly Thr Ser Ile Asn
                85                  90                  95

Pro Ser Pro Ser Leu Gly Ser Met Lys Asp Glu Pro Val Pro Ala Ile
            100                 105                 110

Gln Lys Ile Val Asn Lys Pro Leu Pro Leu Pro Gly Gln Asn Ser
        115                 120                 125

Ser Ser Leu Thr Pro Ser Gln Glu Thr Ile Asn Met Ile Ser Asn Ala
    130                 135                 140

Ser Gln Gln Ala Pro Asp Gly Pro Leu Asn Asn Ile Ser Pro Val Pro
145                 150                 155                 160

Gly Phe Lys Glu Ala Met Gly Gly Asn Val Arg Arg Asn Asp Gly Gln
                165                 170                 175

Asn Leu Tyr Gly Ser Thr Ser Pro Ala Val Thr Ala Ser Ala Pro Asn
            180                 185                 190
```

```
Met Pro Ala Phe Asn Pro Asn Arg Lys Ala Pro Arg Pro Pro Gln Ile
        195                 200                 205
Pro His Asn Thr Val Ile Pro Ala Lys Pro Met Gln Ser Leu Ser Ser
    210                 215                 220
Arg Arg Gly Leu Lys Leu Pro Gly Gly Met Lys Leu Lys Leu Pro
225                 230                 235                 240
Ser Lys Gly Asp Ala Pro Ala Ser Met Pro Ser Thr Val Pro Ala Ala
            245                 250                 255
Ser Ser Val Lys Pro Val Val His Gln Glu Phe Ala Ala Thr Pro Ser
        260                 265                 270
Asn Lys Asn His Ile Lys Asn Asn Gly Ser Thr Glu Gly Lys Arg
    275                 280                 285
Ser Asn Pro Gly Ser Leu Val Asn Ala Val Gln Thr Ser Ile Ser
290                 295                 300
Ser Ala Asn Asp Gln Gln Asp Thr Glu Gly Thr Glu Pro Lys Ser Asn
305                 310                 315                 320
Ser Asn Gly Thr Gly Leu Phe Ala Asn Phe Ser Arg Tyr Val Asp Ile
                325                 330                 335
Lys Ser Gly Ser Leu Asn Phe Ala Gly Lys Leu Ser Leu Ser Ser Arg
            340                 345                 350
Gly Ile Asp Phe Ser Asn Gly Ser Ser Arg Ile Thr Leu Asp Glu
        355                 360                 365
Leu Gln Phe Ile Glu Glu Leu Gly His Gly Asn Tyr Gly Thr Val Ser
    370                 375                 380
Lys Val Leu His Lys Pro Asn Asn Val Leu Met Ala Met Lys Glu Val
385                 390                 395                 400
Arg Leu Glu Leu Asp Glu Ser Lys Phe Arg Gln Ile Leu Met Glu Leu
                405                 410                 415
Glu Val Leu His Lys Cys Asn Ser Pro Phe Ile Val Asp Phe Tyr Gly
            420                 425                 430
Ala Phe Phe Ile Glu Gly Ala Val Tyr Met Cys Met Glu Tyr Met Asp
        435                 440                 445
Gly Gly Ser Leu Asp Lys Ile Tyr Asp Glu Asn Pro Glu Met Gly Gly
    450                 455                 460
Ile Asp Glu Pro Gln Leu Ala Phe Ile Thr Asn Ala Val Ile Gln Gly
465                 470                 475                 480
Leu Arg Glu Leu Lys Glu Val His Asn Val Ile His Arg Asp Val Lys
                485                 490                 495
Pro Thr Asn Ile Leu Cys Ser Ala Lys Gln Gly Thr Val Lys Leu Cys
            500                 505                 510
Asp Phe Gly Val Ser Gly Asn Leu Val Ala Ser Leu Ala Lys Thr Asn
        515                 520                 525
Ile Gly Cys Gln Ser Tyr Met Ala Pro Glu Arg Ile Lys Ser Leu Asn
    530                 535                 540
Pro Asp Arg Gly Thr Tyr Thr Val Gln Ser Asp Ile Trp Ser Leu Gly
545                 550                 555                 560
Leu Ser Ile Leu Glu Met Ala Leu Gly Arg Tyr Pro Tyr Pro Pro Glu
                565                 570                 575
Thr Phe Asp Asn Ile Phe Ser Gln Leu Ser Ala Ile Val Asp Gly Pro
            580                 585                 590
Pro Pro Lys Leu Pro Ala Asp Lys Phe Ser Asp Glu Ala Gln Asp Phe
        595                 600                 605
Val Ser Leu Cys Leu Gln Lys Ile Pro Asp Arg Arg Pro Asn Tyr Ser
    610                 615                 620
```

Asn Leu Tyr Glu His Pro Trp Leu Ala Lys Tyr Arg Ser Ile Asp Val
625                 630                 635                 640

Gln Met Gly Pro Tyr Ile Thr Lys Arg Leu Glu Ile Arg Lys Arg Ile
            645                 650                 655

Leu Ala Glu Lys Gly Glu Asp Gly Leu His Arg Thr Val Pro Ala Leu
            660                 665                 670

His Lys Gly Gly Leu
        675

<210> SEQ ID NO 53
<211> LENGTH: 2175
<212> TYPE: DNA
<213> ORGANISM: Kluyveromyces lactis

<400> SEQUENCE: 53

| | | | | | |
|---|---|---|---|---|---|
| atgagtaata | gtttgagacg | gtccagtgcg | tcatcttctt | cgtcgcaggg | gaaaccagga | 60 |
| cgaaatggca | gtgggaatgg | atcgtattct | caaatcaatt | ccagtttgca | tgccagagtg | 120 |
| aaagctttcc | aagaacagag | acagttgaaa | cggtccggta | gtattcattc | taaccagtca | 180 |
| cagaattcgg | ttcagataga | gcagattgtg | aataaaccgt | tgccgcctct | gccaccgaag | 240 |
| acaatggttg | aagaggctga | gaatagccag | caattagaac | aacaacaaca | acaacaacat | 300 |
| aatatacaaa | tacagcaaac | acaacagcaa | caacaacgac | aaccgatcct | aaaacaacag | 360 |
| gaccagcatc | tacagcatct | acagcatacg | gaattgttag | cacaatcagt | tacggaaaat | 420 |
| gaccagcatg | atcagcagca | acagcagcag | gggggcctgc | tgctgtctcc | taagacagaa | 480 |
| cttcccgata | tagaggaaaa | gaagggacag | tttgagaagc | agacacaaga | ggctctggcg | 540 |
| aatttgagta | tacagtctga | cggtatgtca | tctgcttcgg | aatcttctgg | tagtgccagt | 600 |
| aataagcaac | aacaggatca | tgaactcaat | ccgattagaa | aggctccaaa | acgtccgcaa | 660 |
| ggtgttccca | gttgtactgg | cagcggcaat | gctggtgcgc | caagtccaat | tggtggcgtg | 720 |
| ggaggttctc | aggcagcagc | aggtactttc | agaccgcctg | ctgctgctgg | ggcgttgta | 780 |
| atgccaaatc | aaccaaggct | ttcacaaggt | cagccacatc | tacaaaaggc | taaacagtct | 840 |
| ttgtctgcaa | gaagaggctt | gaagcttcct | acgggcggca | tgtccttgaa | gatgaaacca | 900 |
| acacatcaac | aacagcagct | tgctcctcaa | catacacatc | aagaatttgc | gggcgctccc | 960 |
| tccaattctg | ctttgccctt | gcaaggaaaa | cgttcgaatc | ccggatcttt | gattaatggt | 1020 |
| attcaatcca | cttctacttc | tttggctaat | agttcacatg | atacacttgg | cactgatcct | 1080 |
| aaatctaatc | ctacttctaa | ttctaactct | ggtatcggtg | gattgtttgc | taattttttcc | 1140 |
| aagtatgtca | atattaaatc | aggatctcta | aatttcgcag | gtaagctgtc | tttatcctct | 1200 |
| aaaggtgtag | actttagcaa | cggttccagt | ttccggataa | agttagatga | actagagttt | 1260 |
| ctggaagaat | tgggtcatgg | taactatggt | aacgtatcca | agttttaca | caagccgact | 1320 |
| catatcataa | tggccatgaa | ggaagtcaga | ttggaattgg | acgaatcaaa | gtttagacag | 1380 |
| atcttaatgg | aacttgaagt | tttgcataat | tgccagtcac | cgtacattgt | ggatttctac | 1440 |
| ggtgcattt | tcattgaagg | tgccgtttat | atgtgtatgg | aatatatgga | tggtggatct | 1500 |
| ctagataaaa | cttatgatga | tgaacaaata | ggggggattg | acgaaccaca | actagcaagg | 1560 |
| ataacaagct | cagtaataca | aggattgaag | gaattgaaag | acgtgcataa | tatcatccat | 1620 |
| cgtgatgtta | aaccaactaa | tatcttgtgt | tctgcaagcc | agggtacaat | taaactatgc | 1680 |
| gattttggtg | tgtcaggtaa | cctcgttgcc | tctttagcca | agacaaatat | cggttgtcaa | 1740 |
| tcttacatgg | ccccagaaag | aatcaaatca | ctgaatccgg | acaaatcaac | gtattctgtc | 1800 |

-continued

```
caatcagata tctggtctttt gggtctatcg atattggaaa tggcattggg agcttatccg    1860
tatccgccag aaacgtttga caacatattc tcacagttga gtgccatcgt cgacggccca    1920
cctcctaaac ttccagaggg aaagttctca gccgatgctc aaaactttgt ttccatgtgt    1980
ttgcaaaaaa tccctgaacg tagacccact tatgccgctc tattagaaca tccatggttg    2040
aaaaaatacg aaaacgttga cgtaagaatg agtgaataca taacgaatag attgaacaaa    2100
aaaagggaat tgctagaaca aacaggcgaa ggtccaccta agcacgttcc tgctttgcat    2160
atgggcggat tgtaa                                                    2175
```

<210> SEQ ID NO 54
<211> LENGTH: 724
<212> TYPE: PRT
<213> ORGANISM: Kluyveromyces lactis

<400> SEQUENCE: 54

```
Met Ser Asn Ser Leu Arg Arg Ser Ser Ala Ser Ser Ser Ser Ser Gln
1               5                   10                  15

Gly Lys Pro Gly Arg Asn Gly Ser Gly Asn Gly Ser Tyr Ser Gln Ile
            20                  25                  30

Asn Ser Ser Leu His Ala Arg Val Lys Ala Phe Gln Glu Gln Arg Gln
        35                  40                  45

Leu Lys Arg Ser Gly Ser Ile His Ser Asn Gln Ser Gln Asn Ser Val
    50                  55                  60

Gln Ile Glu Gln Ile Val Asn Lys Pro Leu Pro Pro Leu Pro Pro Lys
65                  70                  75                  80

Thr Met Val Glu Glu Ala Glu Asn Ser Gln Gln Leu Glu Gln Gln Gln
                85                  90                  95

Gln Gln Gln His Asn Ile Gln Ile Gln Gln Thr Gln Gln Gln Gln Gln
            100                 105                 110

Arg Gln Pro Ile Leu Lys Gln Gln Asp Gln His Leu Gln His Leu Gln
        115                 120                 125

His Thr Glu Leu Leu Ala Gln Ser Val Thr Glu Asn Asp Gln His Asp
    130                 135                 140

Gln Gln Gln Gln Gln Gln Gly Gly Leu Leu Leu Ser Pro Lys Thr Glu
145                 150                 155                 160

Leu Pro Asp Ile Glu Glu Lys Lys Gly Gln Phe Glu Lys Gln Thr Gln
                165                 170                 175

Glu Ala Leu Ala Asn Leu Ser Ile Gln Ser Asp Gly Met Ser Ser Ala
            180                 185                 190

Ser Glu Ser Ser Gly Ser Ala Ser Asn Lys Gln Gln Gln Asp His Glu
        195                 200                 205

Leu Asn Pro Ile Arg Lys Ala Pro Lys Arg Pro Gln Gly Val Pro Ser
    210                 215                 220

Cys Thr Gly Ser Gly Asn Ala Gly Ala Pro Ser Pro Ile Gly Gly Val
225                 230                 235                 240

Gly Gly Ser Gln Ala Ala Ala Gly Thr Phe Arg Pro Pro Ala Ala Ala
                245                 250                 255

Gly Gly Val Val Met Pro Asn Gln Pro Arg Leu Ser Gln Gly Gln Pro
            260                 265                 270

His Leu Gln Lys Ala Lys Gln Ser Leu Ser Ala Arg Arg Gly Leu Lys
        275                 280                 285

Leu Pro Thr Gly Gly Met Ser Leu Lys Met Lys Pro Thr His Gln Gln
    290                 295                 300
```

-continued

```
Gln Gln Leu Ala Pro Gln His Thr His Gln Glu Phe Ala Gly Ala Pro
305                 310                 315                 320

Ser Asn Ser Ala Leu Pro Leu Gln Gly Lys Arg Ser Asn Pro Gly Ser
            325                 330                 335

Leu Ile Asn Gly Ile Gln Ser Thr Ser Thr Ser Leu Ala Asn Ser Ser
        340                 345                 350

His Asp Thr Leu Gly Thr Asp Pro Lys Ser Asn Pro Thr Ser Asn Ser
    355                 360                 365

Asn Ser Gly Ile Gly Gly Leu Phe Ala Asn Phe Ser Lys Tyr Val Asn
370                 375                 380

Ile Lys Ser Gly Ser Leu Asn Phe Ala Gly Lys Leu Ser Leu Ser Ser
385                 390                 395                 400

Lys Gly Val Asp Phe Ser Asn Gly Ser Ser Phe Arg Ile Lys Leu Asp
                405                 410                 415

Glu Leu Glu Phe Leu Glu Glu Leu Gly His Gly Asn Tyr Gly Asn Val
            420                 425                 430

Ser Lys Val Leu His Lys Pro Thr His Ile Ile Met Ala Met Lys Glu
        435                 440                 445

Val Arg Leu Glu Leu Asp Glu Ser Lys Phe Arg Gln Ile Leu Met Glu
450                 455                 460

Leu Glu Val Leu His Asn Cys Gln Ser Pro Tyr Ile Val Asp Phe Tyr
465                 470                 475                 480

Gly Ala Phe Phe Ile Glu Gly Ala Val Tyr Met Cys Met Glu Tyr Met
                485                 490                 495

Asp Gly Gly Ser Leu Asp Lys Thr Tyr Asp Asp Glu Gln Ile Gly Gly
            500                 505                 510

Ile Asp Glu Pro Gln Leu Ala Arg Ile Thr Ser Ser Val Ile Gln Gly
        515                 520                 525

Leu Lys Glu Leu Lys Asp Val His Asn Ile Ile His Arg Asp Val Lys
530                 535                 540

Pro Thr Asn Ile Leu Cys Ser Ala Ser Gln Gly Thr Ile Lys Leu Cys
545                 550                 555                 560

Asp Phe Gly Val Ser Gly Asn Leu Val Ala Ser Leu Ala Lys Thr Asn
                565                 570                 575

Ile Gly Cys Gln Ser Tyr Met Ala Pro Glu Arg Ile Lys Ser Leu Asn
            580                 585                 590

Pro Asp Lys Ser Thr Tyr Ser Val Gln Ser Asp Ile Trp Ser Leu Gly
        595                 600                 605

Leu Ser Ile Leu Glu Met Ala Leu Gly Ala Tyr Pro Tyr Pro Pro Glu
610                 615                 620

Thr Phe Asp Asn Ile Phe Ser Gln Leu Ser Ala Ile Val Asp Gly Pro
625                 630                 635                 640

Pro Pro Lys Leu Pro Glu Gly Lys Phe Ser Ala Asp Ala Gln Asn Phe
                645                 650                 655

Val Ser Met Cys Leu Gln Lys Ile Pro Glu Arg Arg Pro Thr Tyr Ala
            660                 665                 670

Ala Leu Leu Glu His Pro Trp Leu Lys Lys Tyr Glu Asn Val Asp Val
        675                 680                 685

Arg Met Ser Glu Tyr Ile Thr Asn Arg Leu Asn Lys Lys Arg Glu Leu
690                 695                 700

Leu Glu Gln Thr Gly Glu Gly Pro Pro Lys His Val Pro Ala Leu His
705                 710                 715                 720

Met Gly Gly Leu
```

<210> SEQ ID NO 55
<211> LENGTH: 2076
<212> TYPE: DNA
<213> ORGANISM: Ahbya gossypii

<400> SEQUENCE: 55

| | | | | | |
|---|---|---|---|---|---|
| atggagcgca | acacggtgca | gagatccggc | actatgcaga | ccgggggcag | cagcagcgca | 60 |
| agcaagaact | acagtaacat | caacgcgaac | ctgcacgcgc | gtgtgaaggc | gttccaggag | 120 |
| cagcggaagc | tgcagcggtc | ggggagcgtg | ggatcaaagt | cgtcgggaca | gtcgcaagac | 180 |
| tcggcagcga | tacagcatat | cgtgaacaag | ccgctgccgc | cgctgccgcc | gggcaagggc | 240 |
| aaggaggcgg | cgccgcccct | gcggcgacag | gggagcatgc | taaaggcgga | ctcacggccg | 300 |
| cggtcgatgt | cttcgtttac | cgggtcaccg | cccgcgtgg | gggcgtccat | cgcggacgct | 360 |
| gagccggtag | cgagcgcaga | gcggccggcg | ccggtgctac | aggcgaatgt | gggccaggag | 420 |
| gcggactcca | tgcctgtgca | gcagagcatt | ccgctgaagg | cggcggccgt | gcccgggcgc | 480 |
| cagccacatc | aaaaaactca | ttctgcatcc | gatatatttc | aacgcacgtc | gtcgcacgtt | 540 |
| ctcccgcaga | tacccatacc | tctgaatccg | atcaggaagg | cccgcggcc | gcggatgcg | 600 |
| ggaatggggc | atcaacgggg | gcgccagggc | tcacattcag | gcatagtgct | gggcccgcag | 660 |
| agcggtgcag | gggcacagg | gagcgcttcc | gacgccccaa | agcatattat | gacaaagtcc | 720 |
| aagccatccc | tttccgcgcg | gaggggactg | aaattaccgt | ctggcggtat | ttctctgaaa | 780 |
| atgaagcagc | cactccaaga | gtttgcatct | cagccatcga | caaagatac | cgctctggca | 840 |
| acgtcaggag | tggtgcctgg | tcaccgcgtc | agcaaaagca | atccggggtc | gcttacgaac | 900 |
| gggattcaga | ccacctcgac | gtcctctgac | aaacaggtcg | atacgaaggg | gactgaacct | 960 |
| agtaagtctg | gcaactctgg | aaccaattct | aacggggcc | tatttgcagt | attctccaag | 1020 |
| tatgtcgata | ttaaatccgg | atcactaaat | tttgctggca | agttatcact | ttcgtctcag | 1080 |
| ggcgtggact | ttagtaatgg | atctagcttt | cgaattacat | tggacgagtt | ggagttttta | 1140 |
| gaagaactag | gccatgggaa | ctacggtacg | gtatccaagg | tactgcacaa | gcccactaat | 1200 |
| atcatgatgg | ctatgaagga | agttaggctg | gagctcgacg | agtccaagtt | tagacaaatt | 1260 |
| ctcatggaac | tagaagtcct | gcataagtgt | cagtccccat | acattgtcga | cttctacggt | 1320 |
| gcattcttta | ttgaagggc | agtctacatg | tgcatggaat | tcatggatgg | cggttcgttg | 1380 |
| gacaagtctt | acgacccca | tgaaataggc | ggaatcgagg | aaccgcagct | tgcccttata | 1440 |
| acagagtcag | taatccgcgg | gttaaaggaa | ttaaagatg | tacacaacat | tatacaccgt | 1500 |
| gatgttaaac | caacaaatat | cttgtgctcc | gcgacacaag | gtaccgttaa | gctctgtgac | 1560 |
| ttcggtgttt | ccgggaacct | agtagcatcc | ttggcacgca | ctaacatcgg | ctgtcaatcc | 1620 |
| tacatggcgc | ccgagcgtat | caagtcttta | aatccagata | aagccacata | ctctgtccag | 1680 |
| tccgatattt | ggtccctggg | cttatccatt | gtggaaatgg | cgttgggtgc | gtacccatac | 1740 |
| cctcctgaaa | catacgacaa | tatattcagt | cagctgagcg | ccatcgttga | cggtccacca | 1800 |
| ccccgtttgc | cgaaggacac | cttctcttcg | gacgcacagg | actttgtgcg | tctgtgcttg | 1860 |
| caaaagatac | ctgaaaggcg | gcctacatac | gcctcactcc | ttgagcaccc | atggctgaag | 1920 |
| aagtatagag | gcctggatgt | ccacatgagc | gaatatatca | caaaaagatt | ggtacaaaga | 1980 |
| caacattatc | ttgaacaaag | cggtgtgggac | gaactcccca | aagtgttacc | tgcattgcat | 2040 |
| ggaaggctgg | taaaaccaca | gccccatatt | ccttaa | | | 2076 |

<210> SEQ ID NO 56

```
<211> LENGTH: 691
<212> TYPE: PRT
<213> ORGANISM: Ashbya gossypii

<400> SEQUENCE: 56

Met Glu Arg Asn Thr Val Gln Arg Ser Gly Thr Met Gln Thr Gly Gly
1               5                   10                  15

Ser Ser Ser Ala Ser Lys Asn Tyr Ser Asn Ile Asn Ala Asn Leu His
            20                  25                  30

Ala Arg Val Lys Ala Phe Gln Glu Gln Arg Lys Leu Gln Arg Ser Gly
        35                  40                  45

Ser Val Gly Ser Lys Ser Gly Gln Ser Gln Asp Ser Ala Ala Ile
    50                  55                  60

Gln His Ile Val Asn Lys Pro Leu Pro Pro Leu Pro Gly Lys Gly
65                  70                  75                  80

Lys Glu Ala Ala Pro Pro Leu Arg Arg Gln Gly Ser Met Leu Lys Ala
                85                  90                  95

Asp Ser Arg Pro Arg Ser Met Ser Ser Phe Thr Gly Ser Pro Pro Ala
            100                 105                 110

Val Gly Ala Ser Ile Ala Asp Ala Glu Pro Val Ala Ser Ala Glu Arg
        115                 120                 125

Pro Ala Pro Val Leu Gln Ala Asn Val Gly Gln Glu Ala Asp Ser Met
    130                 135                 140

Pro Val Gln Gln Ser Ile Pro Leu Lys Ala Ala Ala Val Pro Gly Arg
145                 150                 155                 160

Gln Pro His Gln Lys Thr His Ser Ala Ser Asp Ile Phe Gln Arg Thr
                165                 170                 175

Ser Ser His Val Leu Pro Gln Ile Pro Ile Pro Leu Asn Pro Ile Arg
            180                 185                 190

Lys Ala Pro Arg Pro Pro Asp Ala Gly Met Gly His Gln Arg Gly Arg
        195                 200                 205

Gln Gly Ser His Ser Gly Ile Val Leu Gly Pro Gln Ser Gly Ala Gly
    210                 215                 220

Gly Thr Gly Ser Ala Ser Asp Ala Pro Lys His Ile Met Thr Lys Ser
225                 230                 235                 240

Lys Pro Ser Leu Ser Ala Arg Arg Gly Leu Lys Leu Pro Ser Gly Gly
                245                 250                 255

Ile Ser Leu Lys Met Lys Gln Pro Leu Gln Glu Phe Ala Ser Gln Pro
            260                 265                 270

Ser Asn Lys Asp Thr Ala Leu Ala Thr Ser Gly Val Val Pro Gly His
        275                 280                 285

Arg Val Ser Lys Ser Asn Pro Gly Ser Leu Thr Asn Gly Ile Gln Thr
    290                 295                 300

Thr Ser Thr Ser Ser Asp Lys Gln Val Asp Thr Lys Gly Thr Glu Pro
305                 310                 315                 320

Ser Lys Ser Gly Asn Ser Gly Thr Asn Ser Asn Gly Gly Leu Phe Ala
                325                 330                 335

Val Phe Ser Lys Tyr Val Asp Ile Lys Ser Gly Ser Leu Asn Phe Ala
            340                 345                 350

Gly Lys Leu Ser Leu Ser Ser Gln Gly Val Asp Phe Ser Asn Gly Ser
        355                 360                 365

Ser Phe Arg Ile Thr Leu Asp Glu Leu Glu Phe Leu Glu Glu Leu Gly
    370                 375                 380

His Gly Asn Tyr Gly Thr Val Ser Lys Val Leu His Lys Pro Thr Asn
385                 390                 395                 400
```

```
Ile Met Met Ala Met Lys Glu Val Arg Leu Glu Leu Asp Ser Lys
            405                 410                 415
Phe Arg Gln Ile Leu Met Glu Leu Glu Val Leu His Lys Cys Gln Ser
            420                 425                 430
Pro Tyr Ile Val Asp Phe Tyr Gly Ala Phe Ile Glu Gly Ala Val
            435                 440                 445
Tyr Met Cys Met Glu Phe Met Asp Gly Gly Ser Leu Asp Lys Ser Tyr
            450                 455                 460
Asp Pro His Glu Ile Gly Gly Ile Glu Pro Gln Leu Ala Leu Ile
465                 470                 475                 480
Thr Glu Ser Val Ile Arg Gly Leu Lys Glu Leu Lys Asp Val His Asn
                    485                 490                 495
Ile Ile His Arg Asp Val Lys Pro Thr Asn Ile Leu Cys Ser Ala Thr
                500                 505                 510
Gln Gly Thr Val Lys Leu Cys Asp Phe Gly Val Ser Gly Asn Leu Val
            515                 520                 525
Ala Ser Leu Ala Arg Thr Asn Ile Gly Cys Gln Ser Tyr Met Ala Pro
            530                 535                 540
Glu Arg Ile Lys Ser Leu Asn Pro Asp Lys Ala Thr Tyr Ser Val Gln
545                 550                 555                 560
Ser Asp Ile Trp Ser Leu Gly Leu Ser Ile Val Glu Met Ala Leu Gly
                565                 570                 575
Ala Tyr Pro Tyr Pro Pro Glu Thr Tyr Asp Asn Ile Phe Ser Gln Leu
            580                 585                 590
Ser Ala Ile Val Asp Gly Pro Pro Arg Leu Pro Lys Asp Thr Phe
            595                 600                 605
Ser Ser Asp Ala Gln Asp Phe Val Arg Leu Cys Leu Gln Lys Ile Pro
610                 615                 620
Glu Arg Arg Pro Thr Tyr Ala Ser Leu Leu Glu His Pro Trp Leu Lys
625                 630                 635                 640
Lys Tyr Arg Gly Leu Asp Val His Met Ser Glu Tyr Ile Thr Lys Arg
                645                 650                 655
Leu Val Gln Arg Gln His Tyr Leu Glu Gln Ser Gly Gly Asp Glu Leu
            660                 665                 670
Pro Lys Val Leu Pro Ala Leu His Gly Arg Leu Val Lys Pro Gln Pro
            675                 680                 685
His Ile Pro
    690

<210> SEQ ID NO 57
<211> LENGTH: 1593
<212> TYPE: DNA
<213> ORGANISM: Pichia stipitis

<400> SEQUENCE: 57
ccttccctgt ctcccctgt ttctgcttca cattcgcaaa taaacagcga tattcaagcg    60
cgactattgg cattccagca gaagagaagc aagcccgtag accattccgg ctctccatca   120
ctctctggaa gccacagcat gacaaattct cccaacaata catctctcaa tcttgccagt   180
atcaatactt atcacgaatc tgactctgat agacatcttc ctatgactcc tgatgtgggc   240
agaaatttat ctggacgagg aaaacataac ttcaggttga atctagatag taccaacagt   300
gatcttccgg ttaataacgg aagcaacgga acggccatgt ctcaaaatag cagtttgaac   360
cgaaacgatt cgttgcgtag tatatccagt gatggtagta taggctctga ttccgaggct   420
```

```
gataagaaac cacaattgca aggactattc gctaactact ccaaatactt ggatatcaag    480
tctggactgt taaatttcgc tggaaaggca tcgttacatt ctaagggtgt ggattttctg    540
tcgggatctt cattcagaat atctctagat gaattggagt acatcgatga gttgggccgt    600
ggaaattatg gctcagttct gaaagtttta cataagccta ccggagttct catggcaatg    660
aaagaggtcc gtcttgagtt ggacgaaacg aagttcacac agatcttgat ggagcttgac    720
attttacaca aatgcgattc tccgtacatt gtcgactttt acggcgcctt ctttgtagaa    780
ggagctgtct atatgtgtat tgagtacatg gatggaggct ccttagataa gatctatggc    840
aaggagcatg gggtcaagga tgaagcttcg ttggcctata ttactgaaag tgtcattcgt    900
ggtcttaaag acttgaaaga tgaacataat atcatacatc gtgatgtgaa accaacgaat    960
atcttaatca atactgctgg aaaggtcaag ctttgtgact tggtgtatc tggaaatttg   1020 gttgcatctt tggctaagac taatatcggg tgtcaatcat acatggctcc agaaagaatc   1080
aagagtatga cccagacga tgctacttac tcggtacaat ctgatatctg gtctcttggt   1140
ttgaccatcc tagaggttgc cgcaggccat tacccatacc cagcggaaac gtatgataac   1200
attttctctc agctcagtgc tattgtagat ggcgagccac ctcaattaga tcctaagatt   1260
tattcaaagg aagcacagat atttgtaaaa tcctgtttga agaagaaccc agatttgaga   1320
ccatcatatg ccgcgctctt gaaaaatcct tggttgttga agtatcgtga cgtagatcca   1380
cacatggatg tgctggtttc caagagagtt catgaacttg aagaagacaa ggagaagcgc   1440
aatgtgagca gatccaatag tttgaagaaa aacccactcc caactccagc taatatcgag   1500
agtgtgcatt ccttacttcg aaacaaggtc aaagctcctg ctttgcatag aggtggatta   1560
ccgaacaaca accgatcatt tttacataag tag                                1593
```

<210> SEQ ID NO 58
<211> LENGTH: 530
<212> TYPE: PRT
<213> ORGANISM: Pichia stipitis

<400> SEQUENCE: 58

```
Pro Ser Ser Ser Pro Val Ser Ala Ser His Ser Gln Ile Asn Ser
1               5                  10                  15

Asp Ile Gln Ala Arg Leu Leu Ala Phe Gln Gln Lys Arg Ser Lys Pro
            20                  25                  30

Val Asp His Ser Gly Ser Pro Ser Leu Ser Gly Ser His Ser Met Thr
        35                  40                  45

Asn Ser Pro Asn Asn Thr Ser Leu Asn Leu Ala Ser Ile Asn Thr Tyr
    50                  55                  60

His Glu Ser Asp Ser Asp Arg His Leu Pro Met Thr Pro Asp Val Gly
65                  70                  75                  80

Arg Asn Leu Ser Gly Arg Gly Lys His Asn Phe Arg Leu Asn Leu Asp
                85                  90                  95

Ser Thr Asn Ser Asp Leu Pro Val Asn Asn Gly Ser Asn Gly Thr Ala
            100                 105                 110

Met Ser Gln Asn Ser Ser Leu Asn Arg Asn Asp Ser Leu Arg Ser Ile
        115                 120                 125

Ser Ser Asp Gly Ser Ile Gly Ser Asp Ser Glu Ala Asp Lys Lys Pro
    130                 135                 140

Gln Leu Gln Gly Leu Phe Ala Asn Tyr Ser Lys Tyr Leu Asp Ile Lys
145                 150                 155                 160

Ser Gly Ser Leu Asn Phe Ala Gly Lys Ala Ser Leu His Ser Lys Gly
                165                 170                 175
```

Val Asp Phe Ser Ser Gly Ser Ser Phe Arg Ile Ser Leu Asp Glu Leu
            180                 185                 190

Glu Tyr Ile Asp Glu Leu Gly Arg Gly Asn Tyr Gly Ser Val Ser Lys
            195                 200                 205

Val Leu His Lys Pro Thr Gly Val Leu Met Ala Met Lys Glu Val Arg
            210                 215                 220

Leu Glu Leu Asp Glu Thr Lys Phe Thr Gln Ile Leu Met Glu Leu Asp
225                 230                 235                 240

Ile Leu His Lys Cys Asp Ser Pro Tyr Ile Val Asp Phe Tyr Gly Ala
            245                 250                 255

Phe Phe Val Glu Gly Ala Val Tyr Met Cys Ile Glu Tyr Met Asp Gly
            260                 265                 270

Gly Ser Leu Asp Lys Ile Tyr Gly Lys Glu His Gly Val Lys Asp Glu
            275                 280                 285

Ala Ser Leu Ala Tyr Ile Thr Glu Ser Val Ile Arg Gly Leu Lys Asp
            290                 295                 300

Leu Lys Asp Glu His Asn Ile Ile His Arg Asp Val Lys Pro Thr Asn
305                 310                 315                 320

Ile Leu Ile Asn Thr Ala Gly Lys Val Lys Leu Cys Asp Phe Gly Val
            325                 330                 335

Ser Gly Asn Leu Val Ala Ser Leu Ala Lys Thr Asn Ile Gly Cys Gln
            340                 345                 350

Ser Tyr Met Ala Pro Glu Arg Ile Lys Ser Met Asn Pro Asp Asp Ala
            355                 360                 365

Thr Tyr Ser Val Gln Ser Asp Ile Trp Ser Leu Gly Leu Thr Ile Leu
            370                 375                 380

Glu Val Ala Ala Gly His Tyr Pro Tyr Pro Ala Glu Thr Tyr Asp Asn
385                 390                 395                 400

Ile Phe Ser Gln Leu Ser Ala Ile Val Asp Gly Glu Pro Pro Gln Leu
            405                 410                 415

Asp Pro Lys Ile Tyr Ser Lys Glu Ala Gln Ile Phe Val Lys Ser Cys
            420                 425                 430

Leu Lys Lys Asn Pro Asp Leu Arg Pro Ser Tyr Ala Ala Leu Leu Lys
            435                 440                 445

Asn Pro Trp Leu Leu Lys Tyr Arg Asp Val Asp Pro His Met Asp Val
            450                 455                 460

Ser Val Ser Lys Arg Val His Glu Leu Glu Glu Asp Lys Glu Lys Arg
465                 470                 475                 480

Asn Val Ser Arg Ser Asn Ser Leu Lys Lys Asn Pro Leu Pro Thr Pro
            485                 490                 495

Ala Asn Ile Glu Ser Val His Ser Leu Leu Arg Asn Lys Val Lys Ala
            500                 505                 510

Pro Ala Leu His Arg Gly Gly Leu Pro Asn Asn Asn Arg Ser Phe Leu
            515                 520                 525

His Lys
    530

<210> SEQ ID NO 59
<211> LENGTH: 1638
<212> TYPE: DNA
<213> ORGANISM: Candida albicans

<400> SEQUENCE: 59
atggttgaag ataagatat agacttgaat attaataatt tgaaaattca cgatgcgcca    60

```
acacgaacac caccggtaag cctgccacca gctttaccaa caccaccaac tccctcaggg    120
attctgctca acactacaat gcaagctaaa ttgatggcct ttcaacaaca aagatcgaaa    180
gcagcagcag cagcagcagc agcagcttca gtttcatcat catcatcagg tacgcaggcg    240
tcatcgtcat ctatatcagc ttcaacatcg gaatcgagtg tatcaacaat accagcaaat    300
attaaccgaa ctgtatcggg taaaagaaa cccaaaccaa acttgaaatt aagtgattta     360
ccattgtcac gtaataatag tttacaccgt tctaacacta gtgctagtga ttcaagtgtg    420
actacgccag aagcagatac ccctaccggt aagatttcaa atgaaccaca acctcaaggt    480
ttgtttgcta attattctga ttatgttgat ataaaatcag gtcaattaaa ttttgctggc    540
aaagcatcat tacattctaa agggattgat tttctgtctg ggtcttcatt tagagtttca    600
ttagatgaat ttgagtattt agaagaattg ggccgtggaa attatgggtc tgtactgaaa    660
gtcttacata aacccaccgg tgtattgatg gcaatgaagg aagttcgatt ggagttagat    720
gagaataagt tcacgcaaat actaatggag ttagatattt tacataaatg tgactcgcca    780
tatattgttg attttttatgg ggctttttttt gttgaaggtg cagtttacat gtgtattgag    840
tacatggatg gaggttcgtt ggatagaata tttggtaacg atgttggtgt taaagatgaa    900
tatgaattag cctatatcac tgagtcggtt atacttggac ttaaagaatt gaaagataaa    960
cataacatta ttcatcgtga tgtcaaaccc actaatattt tagtgaacac ccagggaaaa   1020
gtaaagttgt gtgattttgg tgtgtctggt aatttagttg cctcattagc caaaacaaat   1080
attggttgtc aatcatatat ggcaccggaa aggatcaaca ctatgagacc tgatgatgcc   1140
acttattcag ttcaatcaga tgtttggtca ttggggttga cgatattaga attagctgtt   1200
ggccattatc cttaccctgc tgaaacatat gataatattt tctcgcaatt aagtgctatt   1260
gttgatggtg aaccaccaaa actttaccca aaggtatact ccaaggaggc acaaatattt   1320
gtcaaatctt gtcttgccaa aaacccagat ttaagaccat cttacgcggc attattgaat   1380
aatccatggt tgatcaaaaa cagaggtaaa gagaccaatc ttgctcagac agtaaaagat   1440
agagtagaag aaattgcgaa attggagaag aacaagagtg tcagtcgaag caacagcatg   1500
aacaaatcag cagccgcagt gcctcctccg agaaatgttg aaagtgttca atcattattg   1560
agaaacaaag tgaaggctcc ggcattacat agaggtggtt tacaaaaagt gaatagaagc   1620
tttcttaata atcattga                                                 1638
```

<210> SEQ ID NO 60
<211> LENGTH: 545
<212> TYPE: PRT
<213> ORGANISM: Candida albicans

<400> SEQUENCE: 60

```
Met Val Glu Asp Lys Asp Ile Asp Leu Asn Ile Asn Asn Leu Lys Ile
1               5                   10                  15

His Asp Ala Pro Thr Arg Thr Pro Pro Val Ser Ser Pro Pro Ala Leu
            20                  25                  30

Pro Thr Pro Pro Thr Pro Ser Gly Ile Ser Leu Asn Thr Thr Met Gln
        35                  40                  45

Ala Lys Leu Met Ala Phe Gln Gln Gln Arg Ser Lys Ala Ala Ala Ala
    50                  55                  60

Ala Ala Ala Ala Ala Ser Val Ser Ser Ser Ser Gly Thr Gln Ala
65                  70                  75                  80

Ser Ser Ser Ser Ile Ser Ala Ser Thr Ser Glu Ser Ser Val Ser Thr
                85                  90                  95
```

-continued

```
Ile Pro Ala Asn Ile Asn Arg Thr Val Ser Gly Lys Lys Pro Lys
            100                 105                 110

Pro Asn Leu Lys Leu Ser Asp Leu Pro Leu Ser Arg Asn Asn Ser Leu
            115                 120                 125

His Arg Ser Asn Thr Ser Ala Ser Asp Ser Ser Val Thr Thr Pro Glu
130                 135                 140

Ala Asp Thr Pro Thr Gly Lys Ile Ser Asn Glu Pro Gln Pro Gln Gly
145                 150                 155                 160

Leu Phe Ala Asn Tyr Ser Asp Tyr Val Asp Ile Lys Ser Gly Gln Leu
                165                 170                 175

Asn Phe Ala Gly Lys Ala Ser Leu His Ser Lys Gly Ile Asp Phe Ser
            180                 185                 190

Ser Gly Ser Ser Phe Arg Val Ser Leu Asp Glu Phe Glu Tyr Leu Glu
        195                 200                 205

Glu Leu Gly Arg Gly Asn Tyr Gly Ser Val Ser Lys Val Leu His Lys
    210                 215                 220

Pro Thr Gly Val Leu Met Ala Met Lys Glu Val Arg Leu Glu Leu Asp
225                 230                 235                 240

Glu Asn Lys Phe Thr Gln Ile Leu Met Glu Leu Asp Ile Leu His Lys
                245                 250                 255

Cys Asp Ser Pro Tyr Ile Val Asp Phe Tyr Gly Ala Phe Phe Val Glu
            260                 265                 270

Gly Ala Val Tyr Met Cys Ile Glu Tyr Met Asp Gly Gly Ser Leu Asp
        275                 280                 285

Arg Ile Phe Gly Asn Asp Val Gly Val Lys Asp Glu Tyr Glu Leu Ala
    290                 295                 300

Tyr Ile Thr Glu Ser Val Ile Leu Gly Leu Lys Glu Leu Lys Asp Lys
305                 310                 315                 320

His Asn Ile Ile His Arg Asp Val Lys Pro Thr Asn Ile Leu Val Asn
                325                 330                 335

Thr Gln Gly Lys Val Lys Leu Cys Asp Phe Gly Val Ser Gly Asn Leu
            340                 345                 350

Val Ala Ser Leu Ala Lys Thr Asn Ile Gly Cys Gln Ser Tyr Met Ala
        355                 360                 365

Pro Glu Arg Ile Asn Thr Met Arg Pro Asp Asp Ala Thr Tyr Ser Val
    370                 375                 380

Gln Ser Asp Val Trp Ser Leu Gly Leu Thr Ile Leu Glu Leu Ala Val
385                 390                 395                 400

Gly His Tyr Pro Tyr Pro Ala Glu Thr Tyr Asp Asn Ile Phe Ser Gln
                405                 410                 415

Leu Ser Ala Ile Val Asp Gly Glu Pro Pro Lys Leu Tyr Pro Lys Val
            420                 425                 430

Tyr Ser Lys Glu Ala Gln Ile Phe Val Lys Ser Cys Leu Ala Lys Asn
        435                 440                 445

Pro Asp Leu Arg Pro Ser Tyr Ala Ala Leu Leu Asn Asn Pro Trp Leu
    450                 455                 460

Ile Lys Asn Arg Gly Lys Glu Thr Asn Leu Ala Gln Thr Val Lys Asp
465                 470                 475                 480

Arg Val Glu Glu Ile Ala Lys Leu Glu Lys Asn Lys Ser Val Ser Arg
                485                 490                 495

Ser Asn Ser Met Asn Lys Ser Ala Ala Ala Val Pro Pro Arg Asn
            500                 505                 510

Val Glu Ser Val Gln Ser Leu Leu Arg Asn Lys Val Lys Ala Pro Ala
        515                 520                 525
```

-continued

```
Leu His Arg Gly Gly Leu Gln Lys Val Asn Arg Ser Phe Leu Asn Asn
    530                 535                 540

His
545
```

<210> SEQ ID NO 61
<211> LENGTH: 2046
<212> TYPE: DNA
<213> ORGANISM: Debaryomyces hansenii

<400> SEQUENCE: 61

| | |
|---|---|
| atgagtgatg caaatgatac gtcgggcaac ttgagtccag gttttgaaaa cctaaatatc | 60 |
| cgaacgccta aggcggtcaa tactgagagc actcagtcgc cacagagggt atcacattca | 120 |
| cagataaatg gtgatattca ggccaggata ttggcgttcc aacaaaagag aacaaagcca | 180 |
| gtgaatggcg gtcatggtgc gttgaatcca atttcaaaat ctacgagcca tttgagtgaa | 240 |
| gcgccagaca aaccattacc accattacca cctttaccca cattgccaac tatgctgtta | 300 |
| caacaaagat cttactctct gggagatact agcgatccag gcttgattcc ttctccgatg | 360 |
| gaaacagaaa atattcagaa tacgaaccat agtgtaaacc gaagtatggg ccaatctatg | 420 |
| agtcaagtta tgggtcaagg catttctaga cgtcgagtt taaagaaaca agaaccacaa | 480 |
| cagctaccat ttgagttact gaagaagccg tctttatccc aaagaagagg aatgaagctt | 540 |
| aatttaagtg aaatgagtag tcccactagt gctagctctc cggatgacac gagccctata | 600 |
| ggtgatggta agagagcct ggtgtttctg aacgcaccaa agggaagtgt ccttgataac | 660 |
| aatgccatga acactactgg cgacttaaca agaagagtat cagaaagaaa aaataaaccct | 720 |
| aacttcaaat tgaatttggc taatacagga ggtcctggag ttagtggcat gaatccacaa | 780 |
| tccacttcaa attcaaattc aaattcgact atctcatcat tgaattcttc tggatcatcg | 840 |
| tctaccatgg ccactaacaa tgaaacaaat caatccaaga agcctcagtt gcaaggatta | 900 |
| tttgcaaatt attcgaaata cgttgatata aaatctggct cgttaaattt tgctggtaag | 960 |
| gcctcgttac attcaaaggg gattgatttc ctgtcaggat tgctgttccg gatctcgtta | 1020 |
| gaggaattgg aattcttaga agaactagga catggtaatt atggtgttgt tctgaaggtt | 1080 |
| ttgcataagc caacgggtgt actaatggcc atgaaagaag ttagattaga attggatgaa | 1140 |
| acaaaattca ctcaaatctt aatggaattg gaaatcttac ataaatgtga ctcgccatat | 1200 |
| attgttgatt tctatggagc tttctttgtt gaaggagctg tttatatgtg tatggagtat | 1260 |
| atggatggag gttcgttgga taagatatat ggaaaggatg atggtgtcaa tgatgaagca | 1320 |
| tgtcttgcat atataaccga atgcgttatc agaggattga aggaattgaa ggatgagcat | 1380 |
| aatattattc acagagacgt gaaacctacg aacattttgg tcaattctct aggaaaagta | 1440 |
| aagttatgtg attttggagt tagtggtaat ttagttgcgt cgttagcgaa aactaatatt | 1500 |
| ggttgtcagt cctatatggc cccggaaaga attaagtcgt taagtccaac cgacaatacc | 1560 |
| tattctgttc agtccgatat ttggtcttta ggattaagta ttttggaaat cgcagcaggt | 1620 |
| cattatcctt atccatctga aacttatggt aacatatttt cccaattaag tgccatcgtt | 1680 |
| gacggtgacc ctccaagatt ggatcctaaa gcattctcta agacgctca attgttatc | 1740 |
| aagagttgtt taaataaaaa ccccgatttg agaccttcat atgctacgtt gttaaagcat | 1800 |
| ccgtggttgg tgaatcatag agatattgat cctcatatgg ataaatttgt aacaagaaag | 1860 |
| ttggaagaac tcgaagagca aaagaacaaa agaacttaa gcagatccaa tagtgttaat | 1920 |
| tcctcaacta ccactgccaa acctccaaaa gagagtgtcc gctctctatt gaaaggaaag | 1980 | gttcaagctc ctgcgttgca tagaggcggg ctaatgaatt ccaatagaaa cagcgttaat    2040 cgataa                                                               2046

<210> SEQ ID NO 62
<211> LENGTH: 681
<212> TYPE: PRT
<213> ORGANISM: Debaryomyces hansenii

<400> SEQUENCE: 62

Met Ser Asp Ala Asn Asp Thr Ser Gly Asn Leu Ser Pro Gly Phe Glu
1               5                   10                  15

Asn Leu Asn Ile Arg Thr Pro Lys Ala Val Asn Thr Glu Ser Thr Gln
            20                  25                  30

Ser Pro Gln Arg Val Ser His Ser Gln Ile Asn Gly Asp Ile Gln Ala
        35                  40                  45

Arg Ile Leu Ala Phe Gln Gln Lys Arg Thr Lys Pro Val Asn Gly Gly
    50                  55                  60

His Gly Ala Leu Asn Pro Ile Ser Lys Ser Thr Ser His Leu Ser Glu
65                  70                  75                  80

Ala Pro Asp Lys Pro Leu Pro Pro Leu Pro Pro Leu Pro Thr Leu Pro
                85                  90                  95

Thr Met Leu Leu Gln Gln Arg Ser Tyr Ser Leu Gly Asp Thr Ser Asp
            100                 105                 110

Pro Gly Leu Ile Pro Ser Pro Met Glu Thr Glu Asn Ile Gln Asn Thr
        115                 120                 125

Asn His Ser Val Asn Arg Ser Met Gly Gln Ser Met Ser Gln Val Met
    130                 135                 140

Gly Gln Gly Ile Ser Arg Thr Ser Ser Leu Lys Lys Gln Glu Pro Gln
145                 150                 155                 160

Gln Leu Pro Phe Glu Leu Leu Lys Lys Pro Ser Leu Ser Gln Arg Arg
                165                 170                 175

Gly Met Lys Leu Asn Leu Ser Glu Met Ser Ser Pro Thr Ser Ala Ser
            180                 185                 190

Ser Pro Asp Asp Thr Ser Pro Ile Gly Asp Gly Lys Glu Ser Leu Val
        195                 200                 205

Phe Leu Asn Ala Pro Lys Gly Ser Val Leu Asp Asn Asn Ala Met Asn
    210                 215                 220

Thr Thr Gly Asp Leu Thr Arg Arg Val Ser Glu Arg Lys Asn Lys Pro
225                 230                 235                 240

Asn Phe Lys Leu Asn Leu Ala Asn Thr Gly Gly Pro Gly Val Ser Gly
                245                 250                 255

Met Asn Pro Gln Ser Thr Ser Asn Ser Asn Ser Asn Ser Thr Ile Ser
            260                 265                 270

Ser Leu Asn Ser Ser Gly Ser Ser Ser Thr Met Ala Thr Asn Asn Glu
        275                 280                 285

Thr Asn Gln Ser Lys Lys Pro Gln Leu Gln Gly Leu Phe Ala Asn Tyr
    290                 295                 300

Ser Lys Tyr Val Asp Ile Lys Ser Gly Ser Leu Asn Phe Ala Gly Lys
305                 310                 315                 320

Ala Ser Leu His Ser Lys Gly Ile Asp Phe Leu Ser Gly Leu Leu Phe
                325                 330                 335

Arg Ile Ser Leu Glu Glu Leu Glu Phe Leu Glu Glu Leu Gly His Gly
            340                 345                 350

Asn Tyr Gly Val Val Leu Lys Val Leu His Lys Pro Thr Gly Val Leu

|     |     |     |     |     | 355 |     |     |     | 360 |     |     |     |     | 365 |     |
| --- | --- | --- | --- | --- | --- | --- | --- | --- | --- | --- | --- | --- | --- | --- | --- |

Met Ala Met Lys Glu Val Arg Leu Glu Leu Asp Glu Thr Lys Phe Thr
        370                     375                 380

Gln Ile Leu Met Glu Leu Glu Ile Leu His Lys Cys Asp Ser Pro Tyr
385                     390                     395                 400

Ile Val Asp Phe Tyr Gly Ala Phe Val Glu Gly Ala Val Tyr Met
                405                     410                     415

Cys Met Glu Tyr Met Asp Gly Gly Ser Leu Asp Lys Ile Tyr Gly Lys
                420                     425                 430

Asp Asp Gly Val Asn Asp Glu Ala Cys Leu Ala Tyr Ile Thr Glu Cys
                435                     440                     445

Val Ile Arg Gly Leu Lys Glu Leu Lys Asp Glu His Asn Ile Ile His
450                     455                     460

Arg Asp Val Lys Pro Thr Asn Ile Leu Val Asn Ser Leu Gly Lys Val
465                     470                     475                     480

Lys Leu Cys Asp Phe Gly Val Ser Gly Asn Leu Val Ala Ser Leu Ala
                    485                     490                     495

Lys Thr Asn Ile Gly Cys Gln Ser Tyr Met Ala Pro Glu Arg Ile Lys
                500                     505                     510

Ser Leu Ser Pro Thr Asp Asn Thr Tyr Ser Val Gln Ser Asp Ile Trp
            515                     520                     525

Ser Leu Gly Leu Ser Ile Leu Glu Ile Ala Ala Gly His Tyr Pro Tyr
            530                     535                     540

Pro Ser Glu Thr Tyr Gly Asn Ile Phe Ser Gln Leu Ser Ala Ile Val
545                     550                     555                     560

Asp Gly Asp Pro Pro Arg Leu Asp Pro Lys Ala Phe Ser Lys Asp Ala
                565                     570                     575

Gln Leu Phe Ile Lys Ser Cys Leu Asn Lys Asn Pro Asp Leu Arg Pro
                580                     585                     590

Ser Tyr Ala Thr Leu Leu Lys His Pro Trp Leu Val Asn His Arg Asp
            595                     600                     605

Ile Asp Pro His Met Asp Lys Phe Val Thr Lys Lys Leu Glu Glu Leu
610                     615                     620

Glu Glu Gln Lys Asn Lys Lys Asn Leu Ser Arg Ser Asn Ser Val Asn
625                     630                     635                     640

Ser Ser Thr Thr Thr Ala Lys Pro Pro Lys Glu Ser Val Arg Ser Leu
                    645                     650                     655

Leu Lys Gly Lys Val Gln Ala Pro Ala Leu His Arg Gly Gly Leu Met
                660                     665                     670

Asn Ser Asn Arg Asn Ser Val Asn Arg
                675                     680

<210> SEQ ID NO 63
<211> LENGTH: 2181
<212> TYPE: DNA
<213> ORGANISM: Yarrowia lipolytica

<400> SEQUENCE: 63
atgagctctc cgccgtcgct gtcagacttg tcgctgaacg atcgcaatcc cgatcgccac    60
ccccttaagg ggctgcatga ggcccggggt atccgtaagg tgtcattaca ctcgcgctca   120
ggctctgtgg ccgaagaaga agagccttcc tccacagact ccaatgctgc tacagcttct   180
catccaccag ctgaccagtt gtcagaagtg tcagcagaaa cgctggcccg tatccaggcc   240
atccatatgt cgcgaatgag cagagatcga tcccactcgt cgcctccaga gcccgaacag   300

```
gaacagctcc agcaactcca ggaccgcacc ccgccgtcgt ggcagactca acgacccac      360
ccccacgtga ccaccgactt tggcccacag ctgacctcac cagaaatttc gcccttcacc     420
acagcgtcgt ctgtgcctcg aaattcagac catagcttct ctcagttcca gaccggctcc    480
ttgcctaaat cctacacagg tggtgtcatc ccccctggcg ttactgccag tcctctcaac    540
ggccctctca ccggaccgct gactggaccg ctcaccggac tctgactgg aggaaccaag     600
ccagtctcaa gacaatcgtc gctgtcgtcg cgacgaggca tgagactgcc aggatcccct    660
ctcgtctctg acgacgagtg cagccaaaac ccggctgcct ccaccccta acccatgaat     720
ttgcatttac ccgactactc caagctcagc tacaatggtg acaacaatgg tagttcttcg    780
gcagatagcc gatctcgcga gagctcctcg tcctccaacg catcatccac ctccaccaca    840
ccctcctgtg ccctcacagg tggactcaca ggtcctaccg ttcagacagg agcccgtctt    900
cccggccgac tatcgtcgca aaactccatc aagcgaaagg gccccggaaa gctgtcgctc    960
agcgggtcgc ccagcagtag tcctgtgact ccatccgatg aagtgctgt ccccctgccc     1020
attgccaaag accaggctcc agcccaggga gccctgctc agggaggcgg tctgtttgca    1080
cagtttcaa agatcgtcga catcaacacg gaaaactca actttgctgg aaaggccagc    1140
ttgcattcgg aaggtatcga cttctcggga ggtacgtcgt tccgaatcaa cattgacgag    1200
ctggagcctc tgggagagct gggacgaggc aactacggaa ctgttacaaa ggtgctgcat    1260
aagcccacag gtatcaccat ggcaatgaag gaggtaaagc tggagctgga caccgccaaa    1320
tttgcccaga taattatgga gctggatatt ctacacaagt gcgagtctcc atacattgtc    1380
gacttttcg gcgccttctt tgtagaggga gctgtttacg aatgcattga gtacatggac     1440
ggaggatcac tggacaaggt gtatgcagga ggtgtggatg agccctgctt ggctgccatc    1500
accgacagtg tggttcgggg tcttatgttc ctgaaggagg agcacaatat tatccacaga    1560
gatgtcaagc ccacgaatat tctcatcaac accgaaggaa aggtcaagtt gtgtgatttc    1620
ggagtgtccg gcaacctcgt tgcatccaag gcatccactg tgatcggatg ccagtcatac    1680
atggcacccg agcgtatcca caaccccgat tctggcaacg tgacatacac tgccaattct    1740
gacatttgga gtttgggcgt aagtatcctg gaaatcgccc aaggctcata ccctacccct    1800
cctgaagcat acaacaatgt tttcgcccag ttgcgagcca ttgtgtctgg tgatcccct     1860
cagcttgccg agcggttctc tcctgaggca cgggactttg ttgcccagtg tctgcagaag    1920
aagccctacc agcggcccac ttaccagcag ttactggagc atccctggct caagaagtac    1980
cggggcgtgg acgttggcat ggccgatttc gtgaagaagg ccctggaacg tggtaagaac    2040
gccacttcca cttccaacga gaccaccccca acgggcacca ctatccctgt gtcccgcaac    2100
aaccctggtt tggtttcccg tgacggacga aacaacatgg ttcctgcttt gcatcatagc    2160
ttcctcaaca atagacaata a                                              2181
```

<210> SEQ ID NO 64
<211> LENGTH: 726
<212> TYPE: PRT
<213> ORGANISM: Yarrowia lipolytica

<400> SEQUENCE: 64

Met Ser Ser Pro Pro Ser Leu Ser Asp Leu Ser Leu Asn Asp Arg Asn
1               5                   10                  15

Pro Asp Arg His Pro Leu Lys Gly Leu His Glu Ala Arg Gly Ile Arg
            20                  25                  30

Lys Val Ser Leu His Ser Arg Ser Gly Ser Val Ala Glu Glu Glu Glu
        35                  40                  45

```
Pro Ser Ser Thr Asp Ser Asn Ala Ala Thr Ala Ser His Pro Pro Ala
    50                  55                  60
Asp Gln Leu Ser Glu Val Ser Ala Glu Thr Leu Ala Arg Ile Gln Ala
65                      70                  75                  80
Ile His Met Ser Arg Met Ser Arg Asp Arg Ser His Ser Ser Pro Pro
                85                  90                  95
Glu Pro Glu Gln Glu Gln Leu Gln Gln Leu Gln Asp Arg Thr Pro Pro
                100                 105                 110
Ser Trp Gln Thr Gln Arg Pro His Pro His Val Thr Thr Asp Phe Gly
            115                 120                 125
Pro Gln Leu Thr Ser Pro Glu Ile Ser Pro Phe Thr Thr Ala Ser Ser
            130                 135                 140
Val Pro Arg Asn Ser Asp His Ser Phe Ser Gln Phe Gln Thr Gly Ser
145                 150                 155                 160
Leu Pro Lys Ser Tyr Thr Gly Gly Val Ile Pro Pro Gly Val Thr Ala
                165                 170                 175
Ser Pro Leu Asn Gly Pro Leu Thr Gly Pro Leu Thr Gly Pro Leu Thr
                180                 185                 190
Gly Pro Leu Thr Gly Gly Thr Lys Pro Val Ser Arg Gln Ser Ser Leu
            195                 200                 205
Ser Ser Arg Arg Gly Met Arg Leu Pro Gly Ser Pro Leu Val Ser Asp
210                 215                 220
Asp Glu Cys Ser Gln Asn Pro Ala Ala Ser Thr Pro Lys Pro Met Asn
225             230                 235                 240
Leu His Leu Pro Asp Tyr Ser Lys Leu Ser Tyr Asn Gly Asp Asn Asn
                245                 250                 255
Gly Ser Ser Ala Asp Ser Arg Ser Arg Glu Ser Ser Ser Ser
                260                 265                 270
Asn Ala Ser Ser Thr Ser Thr Thr Pro Ser Cys Ala Leu Thr Gly Gly
            275                 280                 285
Leu Thr Gly Pro Thr Val Gln Thr Gly Ala Arg Leu Pro Gly Arg Leu
    290                 295                 300
Ser Ser Gln Asn Ser Ile Lys Arg Lys Gly Pro Gly Lys Leu Ser Leu
305                 310                 315                 320
Ser Gly Ser Pro Ser Ser Pro Val Thr Pro Ser Asp Gly Ser Ala
                325                 330                 335
Val Pro Leu Pro Ile Ala Lys Asp Gln Ala Pro Ala Gln Gly Ala Pro
                340                 345                 350
Ala Gln Gly Gly Gly Leu Phe Ala Gln Phe Ser Lys Ile Val Asp Ile
            355                 360                 365
Asn Thr Gly Lys Leu Asn Phe Ala Gly Lys Ala Ser Leu His Ser Glu
    370                 375                 380
Gly Ile Asp Phe Ser Gly Gly Thr Ser Phe Arg Ile Asn Ile Asp Glu
385                 390                 395                 400
Leu Glu Pro Leu Gly Glu Leu Gly Arg Gly Asn Tyr Gly Thr Val Thr
                405                 410                 415
Lys Val Leu His Lys Pro Thr Gly Ile Thr Met Ala Met Lys Glu Val
                420                 425                 430
Lys Leu Glu Leu Asp Thr Ala Lys Phe Ala Gln Ile Ile Met Glu Leu
            435                 440                 445
Asp Ile Leu His Lys Cys Glu Ser Pro Tyr Ile Val Asp Phe Phe Gly
    450                 455                 460
Ala Phe Phe Val Glu Gly Ala Val Tyr Glu Cys Ile Glu Tyr Met Asp
```

```
                    465                 470                 475                 480
Gly Gly Ser Leu Asp Lys Val Tyr Ala Gly Gly Val Asp Glu Pro Cys
                485                 490                 495

Leu Ala Ala Ile Thr Asp Ser Val Val Arg Gly Leu Met Phe Leu Lys
            500                 505                 510

Glu Glu His Asn Ile Ile His Arg Asp Val Lys Pro Thr Asn Ile Leu
        515                 520                 525

Ile Asn Thr Glu Gly Lys Val Lys Leu Cys Asp Phe Gly Val Ser Gly
    530                 535                 540

Asn Leu Val Ala Ser Lys Ala Ser Thr Val Ile Gly Cys Gln Ser Tyr
545                 550                 555                 560

Met Ala Pro Glu Arg Ile His Asn Pro Asp Ser Gly Asn Val Thr Tyr
                565                 570                 575

Thr Ala Asn Ser Asp Ile Trp Ser Leu Gly Val Ser Ile Leu Glu Ile
            580                 585                 590

Ala Gln Gly Ser Tyr Pro Tyr Pro Glu Ala Tyr Asn Asn Val Phe
        595                 600                 605

Ala Gln Leu Arg Ala Ile Val Ser Gly Asp Pro Pro Gln Leu Ala Glu
    610                 615                 620

Arg Phe Ser Pro Glu Ala Arg Asp Phe Val Ala Gln Cys Leu Gln Lys
625                 630                 635                 640

Lys Pro Tyr Gln Arg Pro Thr Tyr Gln Gln Leu Leu Glu His Pro Trp
                645                 650                 655

Leu Lys Lys Tyr Arg Gly Val Asp Val Gly Met Ala Asp Phe Val Lys
            660                 665                 670

Lys Ala Leu Glu Arg Gly Lys Asn Ala Thr Ser Thr Ser Asn Glu Thr
        675                 680                 685

Thr Pro Thr Gly Thr Thr Ile Pro Val Ser Arg Asn Asn Pro Gly Leu
    690                 695                 700

Val Ser Arg Asp Gly Arg Asn Asn Met Val Pro Ala Leu His His Ser
705                 710                 715                 720

Phe Leu Asn Asn Arg Gln
                725

<210> SEQ ID NO 65
<211> LENGTH: 1818
<212> TYPE: DNA
<213> ORGANISM: Schizosaccharomyces pombe

<400> SEQUENCE: 65
atgtcttctc caaataatca acccttgtct tgctcattga dacagctgtc tatttctcct      60
accgcacctc ccggtgatgt tggtactccc ggctcgctcc tttctctttc gtcttcaagt     120
tcttcaaaca ccgattcttc tggttcttcc ttgggttcct tgtctttaaa ttctaacagt     180
agtggcagtg acaatgactc aaaggttcct tctcctagtc gtgaaatacc ttccgatccc     240
cctcttcccc gtgccgtgcc tacggtcaga cttggcagat ctacgtccag tcggagtcgt     300
aactctctta accttgacat gaaggatcct tcggaaaaac ctagacgttc acttcctaca     360
gcagctggtc agaacaatat tggatctcct cctactccac cgggcccatt tcctggagga     420
ctttcaactg atatacagga gaaattgaag gccttccatg catctagatc aaaatcaatg     480
ccggaagtag tcaacaagat cagtagtcca actacccta ttgtcggtat gggtcaacga     540
ggaagttatc ctttgcctaa ctctcaactt gctggtcgat taagtaattc gcccgtaaag     600
tctccgaata tgccagagtc cgggcttgca aaatcacttg ctgctgctag gaatccttta     660
```

```
ctcaaccgtc caacgtcctt caatcgacaa acgagaatcc gtcgtgcacc acctggaaaa    720
ctcgatttat ccaattccaa tcccaccagc cctgtcagtc cgtctagcat ggcttctcgc    780
cgtggcctaa acattcctcc caccctttaaa caggctgttt cggaaacccc ttttccaca    840 ttttcggata ttttggatgc aaaatcaggc accttaaatt ttaaaaacaa agccgtgtta    900
aattcagaag gtgttaactt ttcatctggc tcttcgtttc gtattaatat gtcagagatt    960
attaagcttg aagaacttgg aaaaggtaac tatggtgttg tgtataaagc attgcatcaa   1020
ccgactggtg tcactatggc cttgaaggaa attaggttgt ccttagaaga agcaacattt   1080
aatcaaatta taatgaatt ggatatttta cataaagcag ttagtcctta tatcgttgac   1140
ttttatggtg cctttttttgt ggaaggttct gttttattt gtatggaata tatggatgct   1200
ggtagcatgg acaaactgta tgctggtggt atcaaagacg aaggagtttt agctagaact   1260
gcttatgctg tagtgcaagg cctcaaaact ttgaagagg agcataatat cattcatcgt   1320
gacgttaaac ctactaatgt tttggtaaat tctaatggcc aggttaagtt atgtgacttt   1380
ggcgtgagtg ggaatcttgt ggcttctata tccaaaacga acattggatg tcaatcttac   1440
atggctcctg aaagaattcg tgttggtgga cctaccaatg gcgtcttgac ttacaccgta   1500
caggctgatg tgtggtctct aggccttacc attttagaaa tggctttagg agcttatccg   1560
tatccacctg aatcatatac ttcaatattt gcacaactat cggcgatttg cgatggcgat   1620
ccaccttctc tccccgattc attttctccc gaagctcgtg attttgtaaa caagtgtttg   1680
aataaaaacc cgtctttgcg tcccgattat catgagttgg ctaaccatcc atggttgtta   1740
aaatatcaaa atgcagatgt ggacatggct tcatgggcaa aaggcgctct taagagaaa   1800 ggtgaaaaaa gaagctaa                                                 1818
```

<210> SEQ ID NO 66
<211> LENGTH: 605
<212> TYPE: PRT
<213> ORGANISM: Schizosaccharomyces pombe

<400> SEQUENCE: 66

```
Met Ser Ser Pro Asn Asn Gln Pro Leu Ser Cys Ser Leu Arg Gln Leu
1               5                   10                  15

Ser Ile Ser Pro Thr Ala Pro Pro Gly Asp Val Gly Thr Pro Gly Ser
            20                  25                  30

Leu Leu Ser Leu Ser Ser Ser Ser Ser Asn Thr Asp Ser Ser Gly
        35                  40                  45

Ser Ser Leu Gly Ser Leu Ser Leu Asn Ser Asn Ser Gly Ser Asp
    50                  55                  60

Asn Asp Ser Lys Val Ser Ser Pro Ser Arg Glu Ile Pro Ser Asp Pro
65                  70                  75                  80

Pro Leu Pro Arg Ala Val Pro Thr Val Arg Leu Gly Arg Ser Thr Ser
                85                  90                  95

Ser Arg Ser Arg Asn Ser Leu Asn Leu Asp Met Lys Asp Pro Ser Glu
            100                 105                 110

Lys Pro Arg Arg Ser Leu Pro Thr Ala Ala Gly Gln Asn Asn Ile Gly
        115                 120                 125

Ser Pro Pro Thr Pro Pro Gly Pro Phe Pro Gly Gly Leu Ser Thr Asp
    130                 135                 140

Ile Gln Glu Lys Leu Lys Ala Phe His Ala Ser Arg Ser Lys Ser Met
145                 150                 155                 160

Pro Glu Val Val Asn Lys Ile Ser Ser Pro Thr Thr Pro Ile Val Gly
                165                 170                 175
```

```
Met Gly Gln Arg Gly Ser Tyr Pro Leu Pro Asn Ser Gln Leu Ala Gly
            180                 185                 190

Arg Leu Ser Asn Ser Pro Val Lys Ser Pro Asn Met Pro Glu Ser Gly
            195                 200             205

Leu Ala Lys Ser Leu Ala Ala Arg Asn Pro Leu Leu Asn Arg Pro
        210                 215                 220

Thr Ser Phe Asn Arg Gln Thr Arg Ile Arg Arg Ala Pro Pro Gly Lys
225                 230                 235                 240

Leu Asp Leu Ser Asn Ser Asn Pro Thr Ser Pro Val Ser Pro Ser Ser
                245                 250                 255

Met Ala Ser Arg Arg Gly Leu Asn Ile Pro Pro Thr Leu Lys Gln Ala
            260                 265                 270

Val Ser Glu Thr Pro Phe Ser Thr Phe Ser Asp Ile Leu Asp Ala Lys
            275                 280                 285

Ser Gly Thr Leu Asn Phe Lys Asn Lys Ala Val Leu Asn Ser Glu Gly
            290                 295                 300

Val Asn Phe Ser Ser Gly Ser Ser Phe Arg Ile Asn Met Ser Glu Ile
305                 310                 315                 320

Ile Lys Leu Glu Glu Leu Gly Lys Gly Asn Tyr Gly Val Val Tyr Lys
                325                 330                 335

Ala Leu His Gln Pro Thr Gly Val Thr Met Ala Leu Lys Glu Ile Arg
            340                 345                 350

Leu Ser Leu Glu Glu Ala Thr Phe Asn Gln Ile Ile Met Glu Leu Asp
            355                 360                 365

Ile Leu His Lys Ala Val Ser Pro Tyr Ile Val Asp Phe Tyr Gly Ala
            370                 375                 380

Phe Phe Val Glu Gly Ser Val Phe Ile Cys Met Glu Tyr Met Asp Ala
385                 390                 395                 400

Gly Ser Met Asp Lys Leu Tyr Ala Gly Gly Ile Lys Asp Glu Gly Val
                405                 410                 415

Leu Ala Arg Thr Ala Tyr Ala Val Val Gln Gly Leu Lys Thr Leu Lys
            420                 425                 430

Glu Glu His Asn Ile Ile His Arg Asp Val Lys Pro Thr Asn Val Leu
            435                 440                 445

Val Asn Ser Asn Gly Gln Val Lys Leu Cys Asp Phe Gly Val Ser Gly
            450                 455                 460

Asn Leu Val Ala Ser Ile Ser Lys Thr Asn Ile Gly Cys Gln Ser Tyr
465                 470                 475                 480

Met Ala Pro Glu Arg Ile Arg Val Gly Gly Pro Thr Asn Gly Val Leu
                485                 490                 495

Thr Tyr Thr Val Gln Ala Asp Val Trp Ser Leu Gly Leu Thr Ile Leu
            500                 505                 510

Glu Met Ala Leu Gly Ala Tyr Pro Tyr Pro Pro Glu Ser Tyr Thr Ser
            515                 520                 525

Ile Phe Ala Gln Leu Ser Ala Ile Cys Asp Gly Asp Pro Pro Ser Leu
            530                 535                 540

Pro Asp Ser Phe Ser Pro Glu Ala Arg Asp Phe Val Asn Lys Cys Leu
545                 550                 555                 560

Asn Lys Asn Pro Ser Leu Arg Pro Asp Tyr His Glu Leu Ala Asn His
                565                 570                 575

Pro Trp Leu Leu Lys Tyr Gln Asn Ala Asp Val Asp Met Ala Ser Trp
            580                 585                 590

Ala Lys Gly Ala Leu Lys Glu Lys Gly Glu Lys Arg Ser
```

<210> SEQ ID NO 67
<211> LENGTH: 1878
<212> TYPE: DNA
<213> ORGANISM: Aspergillus terreus

<400> SEQUENCE: 67

```
atgtccgccg acagggaccc tcttaccgat ctcgatcggg actccaagtc cgatcacacc      60
gacgatgacc tctcaccctc ggtcacgacc cctcccactg ccataccgtc tctccggccg     120
acccccgatc agtctacagg gatcactgcg tcgtccaccc accttggtca aatcaatgcc     180
gcgcgacatg ggacggtgcc ctcccccgt ccacaggcct ccatgagcgg ggccgcccag      240
gggggctga atcaggatat tttggcgaaa atgaaggcat tctcccttc ccgacagggg       300
gctccgccga ccttacccca tactgtttcc accggcgccg tcccaaaaac gcccccgact     360
ggtcccagtc caggtgcccg ctcgcccccc gtcgtcaatg gccccctcgc tggtgccttg     420
gcaggccgtc tcccccccgg tgctcgcccg cagacgaaga actgggtgtc ttcgccttct     480
atcccaggca aggcccccag cccgacccg acgaaaccag gagggcttgc ggcgaaacgg      540
atgaagcccg gtcttaagct ctcggatgcg gcggggccga atggtgcgtc tgggaaccag     600
tcgccggcaa atgatgcgga tggtcagaca gagaccgcgt tctcgaagta ttcggaattt     660
atcgatacca agacggggac attgaacttc aaaaacaagg cgatcctcca cggggcggg     720
atcgagtttt cctcgggcca cagcttcaat atctcgctgg acgaagtcga tcgcttggat     780
gagttaggca agggcaacta tggaactgtc tacaaagtcc gccacagtcg tccgcatatg     840
cgaaaaccgg gcatggggct gagcggcatc gtgagtcggc cggccgggtc ggactcgaca     900
tcggactcgc cccaggacag cctctccggg gtgattatgg cgatgaagga gattcgcctc     960
gagttggatg aaaacaagtt cgcgcagatc atcatggagc tggaaatcct ccaccgctgc    1020
gtttcaccct tcatcatcga cttctacggc gccttcttcc aggaaggggc ggtatatatc    1080
tgcgtggaat atatgacgg cgggtcgatc gacaagctgt acaaggaagg cgtgccagag    1140
aatatccttc gcaaggtcgc gctgtcgacg gtgatgggcc tccgcacgct gaaagaggac    1200
cataacatca tccatcgcga cgtgaaaccg acaaatatcc tggtcaacac ccggggacag    1260
atcaagatct gcgattttgg cgtcagtgga aacttggtgg ccagtatcgc gaaaacgaac    1320
atcggttgcc agagctacat ggccccgag cggattgccg tggtggcgt acagcaatcg     1380
ggagccggcg gcgcggcac ctacagtgtg cagagcgaca tctggagttt aggattgagc    1440
attatcgaat gtgctatcgg tcgatacccc tacccgccgg agaccttcaa caatatcttc    1500
agccagctgc atgctatcgt ccacggcgat ccgccgactc tccccgaatc cgggtactcg    1560
gatgaggcac atgcctttgt ccgcgcgtgt ctggacaaga atcccgccaa ccggccctcc    1620
tattccatgc tcctccgcca tccctggctt gcaccgttga tgcaacccc ggctgccgat    1680
ggggatgata caggcacgga tgcttcgtca gcgacagagg atcaggaagt ggccgactgg    1740
gtcaaggaaa tgttgagccg ccaggcgcgt ggcctcctcc acgacggcga caagcccgcg    1800
cttcatgccg tagccttgga tgctgttcct ggaagccctc ttttggacga ccctgcgtcg    1860
atctcgctgc catcttag                                                 1878
```

<210> SEQ ID NO 68
<211> LENGTH: 624
<212> TYPE: PRT
<213> ORGANISM: Aspergillus terreus

```
<400> SEQUENCE: 68

Met Ser Ala Asp Arg Asp Pro Leu Thr Asp Leu Asp Arg Asp Ser Lys
1               5                   10                  15

Ser Asp His Thr Asp Asp Leu Ser Pro Ser Val Thr Thr Pro Pro
            20                  25                  30

Thr Ala Ile Pro Ser Leu Arg Pro Thr Pro Asp Gln Ser Thr Gly Ile
            35                  40                  45

Thr Ala Ser Ser Thr His Leu Gly Gln Ile Asn Ala Ala Arg His Gly
        50                  55                  60

Thr Val Pro Ser Pro Arg Pro Gln Ala Ser Met Ser Gly Ala Ala Gln
65                  70                  75                  80

Gly Gly Leu Asn Gln Asp Ile Leu Ala Lys Met Lys Ala Phe Ser Leu
                85                  90                  95

Ser Arg Gln Gly Ala Pro Pro Thr Leu Pro His Thr Val Ser Thr Gly
            100                 105                 110

Ala Val Pro Lys Thr Pro Pro Thr Gly Pro Ser Pro Gly Ala Arg Ser
            115                 120                 125

Pro Ser Val Val Asn Gly Pro Leu Ala Gly Ala Leu Ala Gly Arg Leu
130                 135                 140

Pro Pro Gly Ala Arg Pro Gln Thr Lys Asn Trp Val Ser Ser Pro Ser
145                 150                 155                 160

Ile Pro Gly Lys Ala Pro Ser Pro Thr Pro Thr Lys Pro Gly Gly Leu
                165                 170                 175

Ala Ala Lys Arg Met Lys Pro Gly Leu Lys Leu Ser Asp Ala Ala Gly
            180                 185                 190

Pro Asn Gly Ala Ser Gly Asn Gln Ser Pro Ala Asn Asp Ala Asp Gly
        195                 200                 205

Gln Thr Glu Thr Ala Phe Ser Lys Tyr Ser Glu Phe Ile Asp Thr Lys
210                 215                 220

Thr Gly Thr Leu Asn Phe Lys Asn Lys Ala Ile Leu His Gly Gly Gly
225                 230                 235                 240

Ile Glu Phe Ser Ser Gly His Ser Phe Asn Ile Ser Leu Asp Glu Val
                245                 250                 255

Asp Arg Leu Asp Glu Leu Gly Lys Gly Asn Tyr Gly Thr Val Tyr Lys
            260                 265                 270

Val Arg His Ser Arg Pro His Met Arg Lys Pro Gly Met Gly Leu Ser
            275                 280                 285

Gly Ile Val Ser Arg Pro Ala Gly Ser Asp Ser Thr Ser Asp Ser Pro
        290                 295                 300

Gln Asp Ser Leu Ser Gly Val Ile Met Ala Met Lys Glu Ile Arg Leu
305                 310                 315                 320

Glu Leu Asp Glu Asn Lys Phe Ala Gln Ile Ile Met Glu Leu Glu Ile
                325                 330                 335

Leu His Arg Cys Val Ser Pro Phe Ile Ile Asp Phe Tyr Gly Ala Phe
            340                 345                 350

Phe Gln Glu Gly Ala Val Tyr Ile Cys Val Glu Tyr Met Asp Gly Gly
        355                 360                 365

Ser Ile Asp Lys Leu Tyr Lys Glu Gly Val Pro Glu Asn Ile Leu Arg
370                 375                 380

Lys Val Ala Leu Ser Thr Val Met Gly Leu Arg Thr Leu Lys Glu Asp
385                 390                 395                 400

His Asn Ile Ile His Arg Asp Val Lys Pro Thr Asn Ile Leu Val Asn
                405                 410                 415
```

```
Thr Arg Gly Gln Ile Lys Ile Cys Asp Phe Gly Val Ser Gly Asn Leu
            420                 425                 430

Val Ala Ser Ile Ala Lys Thr Asn Ile Gly Cys Gln Ser Tyr Met Ala
        435                 440                 445

Pro Glu Arg Ile Ala Gly Gly Val Gln Gln Ser Gly Ala Gly Gly
    450                 455                 460

Gly Gly Thr Tyr Ser Val Gln Ser Asp Ile Trp Ser Leu Gly Leu Ser
465                 470                 475                 480

Ile Ile Glu Cys Ala Ile Gly Arg Tyr Pro Tyr Pro Glu Thr Phe
                485                 490                 495

Asn Asn Ile Phe Ser Gln Leu His Ala Ile Val His Gly Asp Pro Pro
            500                 505                 510

Thr Leu Pro Glu Ser Gly Tyr Ser Asp Glu Ala His Ala Phe Val Arg
        515                 520                 525

Ala Cys Leu Asp Lys Asn Pro Ala Asn Arg Pro Ser Tyr Ser Met Leu
    530                 535                 540

Leu Arg His Pro Trp Leu Ala Pro Leu Met Gln Pro Pro Ala Ala Asp
545                 550                 555                 560

Gly Asp Asp Thr Gly Thr Asp Ala Ser Ser Ala Thr Glu Asp Gln Glu
                565                 570                 575

Val Ala Asp Trp Val Lys Glu Met Leu Ser Arg Gln Ala Arg Gly Leu
            580                 585                 590

Leu His Asp Gly Asp Lys Pro Ala Leu His Val Ala Leu Asp Ala
        595                 600                 605

Val Pro Gly Ser Pro Leu Leu Asp Asp Pro Ala Ser Ile Ser Leu Pro
    610                 615                 620

<210> SEQ ID NO 69
<211> LENGTH: 1971
<212> TYPE: DNA
<213> ORGANISM: Aspergillus fumigatus

<400> SEQUENCE: 69
atgagcacgg ctacagtggg cccagggcaa gaatcggtcg cagaagttcc ctccgctcaa    60
atcgatattg acgaccgatc cgacaacaca acggacgatg accttccccc ctctgttact   120
gctcctccgt ctcttacttc ggtgccatcc ctgcggccgg atcgggatat gacatcgggg   180
ataagtgctt cgtctactca tttgggccaa atcaatgcgg ctcggcgtgg tgcagggaca   240
ccgacacggc cgcacgcctc catgagtggc gcacagccgg gcggtttgaa tcaggacatc   300
ctggccaaga tgaaggcctt ctccctctcc agacagggtg ccccccccca tttacctcat   360
gctgtctcta ccggaacaat cccttcgtcc aggccaagca tttccgcttc gccaagtccg   420
gtaggagggc cgtcgcctcc catgggaggt gcacttgccg gcgtcttcc cccgacagca   480 cgccctcatg gtaaaaattg gcgtcttca ccctcagtac cgggagctac tgcaggttct   540
cattcgcctt cgccaaaaac cggcagcctg ccgcaaaaa gaatgaaacc agggttgaaa   600
ctgtcagatg ccactggccc tgcgactggc tctggaacca gctcgcctgg cgatggatct   660
tcggacgcat ctggagggtc agcattcagc aaatattcag agtacattga cacgaaggca   720
gggactctta atttcaagaa caaggcgatt ctgcacggtg cggcgtcga attctcgtcc   780 ggacatagtt tcagcatctc gttagatgag gttgagcgac tggatgagct aggtaagggc   840
aactacggaa ccgtctacaa agttcgacat agccggcccc atatgcgcaa acctggtatg   900
gggcttcgcg gcatcattag tcgcccagct gagaactcga ccccggatag cacttctgcg   960
gctaagcccc aggacaatct ttctggttac attatggcga tgaaggagat tcgcttggag  1020
```

-continued

```
ctggatgaaa acaaatttgc ccagatcatc atggagctgg atatcttgca ccgttgcgtt    1080
tcgccattca ttatcgactt ctacggcgct ttctttcagg agggtgcggt ctatatgtgt    1140
gtggagtata tggacggagg ctctatcgat aaactctaca aggacggcgt acccgaaaac    1200
attcttcgaa aggtcgcatt atccaccgtt atgggattga agaccctcaa agatgatcat    1260
aacatcattc atcgggacgt gaagcctact aatattctcg tcaattcccg aggtcaaatc    1320
aagatttgcg atttcggcgt gagcggcaat ttggtcgcca gtattgcgaa gactaatatt    1380
ggctgccaga gttatatggc acctgaacgt attgcaggag gcggcgtcca gcagtccggc    1440
gcgactggtg gtggaactta tagtgtgcag agcgacatct ggagtttggg cctgaccatc    1500
atcgaatgcg ctatcggtcg ctatccatat cctccggaaa cctttaacaa catttttcagc    1560 cagttgcatg ctatcgtgca tggggatccg ccaaccttac cggaggaagg atattcggaa    1620
gaggcgcatg catttgtcca tgcttgcttg gacaaaaatc ccagcaagcg tccttcgtat    1680
agtaccttac tcagacatcc ctggcttgct cccttgatgc aacccccgac agagtcgaat    1740
ggtaccgagg caacgtccgc cgctccatct gctggccaac ctggcgggcc cgatacgagt    1800
actgcgactg aggatgagga ggtggcggaa tgggtcaagg agcgaattga acgtcgccaa    1860
cgggggcacc tacaagaggc agagaaacct gcattgcatg cagtggcctt agatgcagtg    1920
cccggtagcc ctctgcttga tgatccctcc tcgctcccat cactttctta g              1971
```

<210> SEQ ID NO 70
<211> LENGTH: 656
<212> TYPE: PRT
<213> ORGANISM: Aspergillus fumigatus

<400> SEQUENCE: 70

```
Met Ser Thr Ala Thr Val Gly Pro Gly Gln Glu Ser Val Ala Glu Val
1               5                   10                  15

Pro Ser Ala Gln Ile Asp Ile Asp Asp Arg Ser Asp Asn Thr Thr Asp
            20                  25                  30

Asp Asp Leu Ser Pro Ser Val Thr Ala Pro Pro Ser Leu Thr Ser Val
        35                  40                  45

Pro Ser Leu Arg Pro Asp Arg Asp Met Thr Ser Gly Ile Ser Ala Ser
    50                  55                  60

Ser Thr His Leu Gly Gln Ile Asn Ala Ala Arg Arg Gly Ala Gly Thr
65                  70                  75                  80

Pro Thr Arg Pro His Ala Ser Met Ser Gly Ala Gln Pro Gly Gly Leu
                85                  90                  95

Asn Gln Asp Ile Leu Ala Lys Met Lys Ala Phe Ser Leu Ser Arg Gln
            100                 105                 110

Gly Ala Pro Pro His Leu Pro His Ala Val Ser Thr Gly Thr Ile Pro
        115                 120                 125

Ser Ser Arg Pro Ser Ile Ser Ala Ser Pro Ser Val Gly Gly Pro
    130                 135                 140

Ser Pro Pro Met Gly Gly Ala Leu Ala Gly Arg Leu Pro Pro Thr Ala
145                 150                 155                 160

Arg Pro His Gly Lys Asn Trp Ala Ser Pro Ser Val Pro Gly Ala
                165                 170                 175

Thr Ala Gly Ser His Ser Pro Ser Pro Lys Thr Gly Ser Leu Ala Ala
            180                 185                 190

Lys Arg Met Lys Pro Gly Leu Lys Leu Ser Asp Ala Thr Gly Pro Ala
        195                 200                 205
```

-continued

Thr Gly Ser Gly Thr Ser Ser Pro Gly Asp Gly Ser Ser Asp Ala Ser
210                 215                 220

Gly Gly Ser Ala Phe Ser Lys Tyr Ser Glu Tyr Ile Asp Thr Lys Ala
225                 230                 235                 240

Gly Thr Leu Asn Phe Lys Asn Lys Ala Ile Leu His Gly Gly Gly Val
            245                 250                 255

Glu Phe Ser Ser Gly His Ser Phe Ser Ile Ser Leu Asp Glu Val Glu
        260                 265                 270

Arg Leu Asp Glu Leu Gly Lys Gly Asn Tyr Gly Thr Val Tyr Lys Val
    275                 280                 285

Arg His Ser Arg Pro His Met Arg Lys Pro Gly Met Gly Leu Arg Gly
290                 295                 300

Ile Ile Ser Arg Pro Ala Glu Asn Ser Thr Pro Asp Ser Thr Ser Ala
305                 310                 315                 320

Ala Lys Pro Gln Asp Asn Leu Ser Gly Tyr Ile Met Ala Met Lys Glu
                325                 330                 335

Ile Arg Leu Glu Leu Asp Glu Asn Lys Phe Ala Gln Ile Ile Met Glu
            340                 345                 350

Leu Asp Ile Leu His Arg Cys Val Ser Pro Phe Ile Ile Asp Phe Tyr
        355                 360                 365

Gly Ala Phe Phe Gln Glu Gly Ala Val Tyr Met Cys Val Glu Tyr Met
370                 375                 380

Asp Gly Gly Ser Ile Asp Lys Leu Tyr Lys Asp Gly Val Pro Glu Asn
385                 390                 395                 400

Ile Leu Arg Lys Val Ala Leu Ser Thr Val Met Gly Leu Lys Thr Leu
                405                 410                 415

Lys Asp Asp His Asn Ile Ile His Arg Asp Val Lys Pro Thr Asn Ile
            420                 425                 430

Leu Val Asn Ser Arg Gly Gln Ile Lys Ile Cys Asp Phe Gly Val Ser
        435                 440                 445

Gly Asn Leu Val Ala Ser Ile Ala Lys Thr Asn Ile Gly Cys Gln Ser
450                 455                 460

Tyr Met Ala Pro Glu Arg Ile Ala Gly Gly Val Gln Gln Ser Gly
465                 470                 475                 480

Ala Thr Gly Gly Gly Thr Tyr Ser Val Gln Ser Asp Ile Trp Ser Leu
                485                 490                 495

Gly Leu Thr Ile Ile Glu Cys Ala Ile Gly Arg Tyr Pro Tyr Pro Pro
            500                 505                 510

Glu Thr Phe Asn Asn Ile Phe Ser Gln Leu His Ala Ile Val His Gly
        515                 520                 525

Asp Pro Pro Thr Leu Pro Glu Glu Gly Tyr Ser Glu Glu Ala His Ala
530                 535                 540

Phe Val His Ala Cys Leu Asp Lys Asn Pro Ser Lys Arg Pro Ser Tyr
545                 550                 555                 560

Ser Thr Leu Leu Arg His Pro Trp Leu Ala Pro Leu Met Gln Pro Pro
                565                 570                 575

Thr Glu Ser Asn Gly Thr Glu Ala Thr Ser Ala Ala Pro Ser Ala Gly
            580                 585                 590

Gln Pro Gly Gly Pro Asp Thr Ser Thr Ala Thr Glu Asp Glu Glu Val
        595                 600                 605

Ala Glu Trp Val Lys Glu Arg Ile Glu Arg Arg Gln Arg Gly His Leu
610                 615                 620

Gln Glu Ala Glu Lys Pro Ala Leu His Ala Val Ala Leu Asp Ala Val
625                 630                 635                 640

Pro Gly Ser Pro Leu Leu Asp Asp Pro Ser Ser Leu Pro Ser Leu Ser
                645                 650                 655

<210> SEQ ID NO 71
<211> LENGTH: 1914
<212> TYPE: DNA
<213> ORGANISM: Neurospora crassa

<400> SEQUENCE: 71

| | |
|---|---:|
| atgtcggacc acgatcccga tcacggccca gctagcccaa atgaatatga cgatgagagc | 60 |
| aacccggctt cgccaggctc agtcgacgag tcgtctgagg caagcacgcc catggacccg | 120 |
| ccaagctcag gttcagatgc gatgcctggt ttcacaccag aaggcgacct gcctcgcaga | 180 |
| gtgccatcat acggaccat ctccgacccg caacacacga attcaatgag ccctagttcg | 240 |
| agtgttcctg ggacattgaa tgccgcacga agacctgcgg catccgcagc aaatcttcca | 300 |
| acggacctca tggcaaaggc acgagctctg catcaacagc ggatgggcat ggctccccga | 360 |
| cccagcatgt cgccgcagaa cagtggactg gtatgggcc ctatgggatc gggcatgggc | 420 |
| gggatgggaa gtatgggggg catgggacac agcatgaatt tgaacatgaa tcacggcggt | 480 |
| ccggcacccg gcggcctgcc cggcggcctt cggttacctc caggtatagc acgaccaccg | 540 |
| ccccaaggct tccccaaatc cgcacctgcc atagccggtc tgggagctaa aaaggccccc | 600 |
| agtctgagcg aacgacgagc gatgaagctc ggagggctac caggagggcc tgggtcgccg | 660 |
| gtgactgcca cgccgaaact gtcagacatg ggcgccgaag acgccaaagc gccagccatt | 720 |
| aatggagaag ggcgcggatc caagctgagc gatttcaaga actatatcga cgcagaaaag | 780 |
| gggtggataa ctttcgcaga cgcagcaacc atcacacgga caggcgtcaa cttcgccaac | 840 |
| ggacagacct tcagaatctc gctagacgag gtcgaagtga tggacgagct aggcaagggc | 900 |
| aactatggta ccgtctacaa agttcgacat agcaaggtca tggcgatgaa agagatcaga | 960 |
| ctcgagctgg atgaatccaa gttttccact attctcaagg aactcgtaat tctccacgag | 1020 |
| tgcgcttcgc cctacatcat tgatttctac ggcgcctttt accaagaagg cgcggtatat | 1080 |
| atgtgcatcg agtacatgga tggcggcagt atagacaagc tatatgccgg aggtatcccc | 1140 |
| gaaaatgtct tgcgcaagat tacatatgca acgatcatgg gcctcaagtg tctaaaagaa | 1200 |
| gatcacaaca tcatccatcg cgatgtcaag cccaccaata ttctggtcaa cacgaatgga | 1260 |
| caagtcaaga tctgcgattt tggcgttttcg ggaaatctcg ttgccagtat agcaaagacc | 1320 |
| aacattggct gccagagtta catggcacca gaacgcatca gcgtggtgg catgtcagct | 1380 |
| gcgggcggcg cggctgccgg gacctacagc gtacaaagcg atatttggag tttgggtctc | 1440 |
| accattatcg agtgtgccat gggtcgatac ccatacccgc tgaggtttc tagcacaatc | 1500 |
| ttcagtcaac tcagtgccat cgttgagggc gaccctcccg gcctcccaag tgagggctac | 1560 |
| tccggcacag cacaggactt tgtcaagtcc tgtctcaaca agatccctgc caagcgccac | 1620 |
| acctacccga tgttgctgat gcacccatgg atcaagtccc tcggcaggcc cgagactatc | 1680 |
| acggaagaag tggaagccga agagaaggcc gcggacgacc agctcgccga cgccaccggc | 1740 |
| tcgctcgaca tcaacagtaa cggaccgatc aacgaccagg gcgatcgtga ggtcgctgag | 1800 |
| tgggtcacca acgttctgga ccgcaagctc aagggcttgc tcagtgataa ggccgagaag | 1860 |
| cccgctctgc acgctgcacc gctggatcaa gtgagcccgg gcattgccgc ttag | 1914 |

<210> SEQ ID NO 72
<211> LENGTH: 637
<212> TYPE: PRT

<213> ORGANISM: Neurospora crassa

<400> SEQUENCE: 72

```
Met Ser Asp His Asp Pro Asp His Gly Pro Ala Ser Pro Asn Glu Tyr
1               5                   10                  15

Asp Asp Glu Ser Asn Pro Ala Ser Pro Gly Ser Val Asp Glu Ser Ser
            20                  25                  30

Glu Ala Ser Thr Pro Met Asp Pro Ser Ser Gly Ser Asp Ala Met
        35                  40                  45

Pro Gly Phe Thr Pro Glu Gly Asp Leu Pro Arg Arg Val Pro Ser Leu
    50                  55                  60

Arg Thr Ile Ser Asp Pro Gln His Thr Asn Ser Met Ser Pro Ser Ser
65                  70                  75                  80

Ser Val Pro Gly Thr Leu Asn Ala Ala Arg Arg Pro Ala Ala Ser Ala
                85                  90                  95

Ala Asn Leu Pro Thr Asp Leu Met Ala Lys Ala Arg Ala Leu His Gln
            100                 105                 110

Gln Arg Met Gly Met Ala Pro Arg Pro Ser Met Ser Pro Gln Asn Ser
        115                 120                 125

Gly Leu Gly Met Gly Pro Met Gly Ser Gly Met Gly Met Gly Ser
130                 135                 140

Met Gly Gly Met Gly His Ser Met Asn Leu Asn Met Asn His Gly Gly
145                 150                 155                 160

Pro Ala Pro Gly Gly Leu Pro Gly Gly Leu Arg Leu Pro Pro Gly Ile
                165                 170                 175

Ala Arg Pro Pro Pro Gln Gly Phe Pro Lys Ser Ala Pro Ala Ile Ala
            180                 185                 190

Gly Leu Gly Ala Lys Lys Ala Pro Ser Leu Ser Glu Arg Arg Ala Met
        195                 200                 205

Lys Leu Gly Gly Leu Pro Gly Gly Pro Gly Ser Pro Val Thr Ala Thr
210                 215                 220

Pro Lys Leu Ser Asp Met Gly Ala Glu Asp Ala Lys Ala Pro Ala Ile
225                 230                 235                 240

Asn Gly Glu Gly Arg Gly Ser Lys Leu Ser Asp Phe Lys Asn Tyr Ile
                245                 250                 255

Asp Ala Glu Lys Gly Trp Ile Thr Phe Ala Asp Ala Ala Thr Ile Thr
            260                 265                 270

Arg Thr Gly Val Asn Phe Ala Asn Gly Gln Thr Phe Arg Ile Ser Leu
        275                 280                 285

Asp Glu Val Glu Val Met Asp Glu Leu Gly Lys Gly Asn Tyr Gly Thr
290                 295                 300

Val Tyr Lys Val Arg His Ser Lys Val Met Ala Met Lys Glu Ile Arg
305                 310                 315                 320

Leu Glu Leu Asp Glu Ser Lys Phe Ser Thr Ile Leu Lys Glu Leu Val
                325                 330                 335

Ile Leu His Glu Cys Ala Ser Pro Tyr Ile Ile Asp Phe Tyr Gly Ala
            340                 345                 350

Phe Tyr Gln Glu Gly Ala Val Tyr Met Cys Ile Glu Tyr Met Asp Gly
        355                 360                 365

Gly Ser Ile Asp Lys Leu Tyr Ala Gly Gly Ile Pro Glu Asn Val Leu
370                 375                 380

Arg Lys Ile Thr Tyr Ala Thr Ile Met Gly Leu Lys Cys Leu Lys Glu
385                 390                 395                 400

Asp His Asn Ile Ile His Arg Asp Val Lys Pro Thr Asn Ile Leu Val
```

```
                    405                 410                 415
Asn Thr Asn Gly Gln Val Lys Ile Cys Asp Phe Gly Val Ser Gly Asn
            420                 425                 430

Leu Val Ala Ser Ile Ala Lys Thr Asn Ile Gly Cys Gln Ser Tyr Met
            435                 440                 445

Ala Pro Glu Arg Ile Ser Gly Gly Met Ser Ala Ala Gly Gly Ala
            450                 455                 460

Ala Ala Gly Thr Tyr Ser Val Gln Ser Asp Ile Trp Ser Leu Gly Leu
465                 470                 475                 480

Thr Ile Ile Glu Cys Ala Met Gly Arg Tyr Pro Tyr Pro Pro Glu Val
                485                 490                 495

Ser Ser Thr Ile Phe Ser Gln Leu Ser Ala Ile Val Glu Gly Asp Pro
            500                 505                 510

Pro Gly Leu Pro Ser Glu Gly Tyr Ser Gly Thr Ala Gln Asp Phe Val
            515                 520                 525

Lys Ser Cys Leu Asn Lys Ile Pro Ala Lys Arg His Thr Tyr Pro Met
            530                 535                 540

Leu Leu Met His Pro Trp Ile Lys Ser Leu Gly Arg Pro Glu Thr Ile
545                 550                 555                 560

Thr Glu Glu Val Glu Ala Glu Lys Ala Ala Asp Asp Gln Leu Ala
                565                 570                 575

Asp Ala Thr Gly Ser Leu Asp Ile Asn Ser Asn Gly Pro Ile Asn Asp
            580                 585                 590

Gln Gly Asp Arg Glu Val Ala Glu Trp Val Thr Asn Val Leu Asp Arg
            595                 600                 605

Lys Leu Lys Gly Leu Leu Ser Asp Lys Ala Glu Lys Pro Ala Leu His
            610                 615                 620

Ala Ala Pro Leu Asp Gln Val Ser Pro Gly Ile Ala Ala
625                 630                 635

<210> SEQ ID NO 73
<211> LENGTH: 1956
<212> TYPE: DNA
<213> ORGANISM: Aspergillus nidulans

<400> SEQUENCE: 73
atgagcgctg aacacgattt tgctgcggag aatccgccgg tttctcctca ttccgatggc      60
gactctgctc ctgttacctt ggaggacgaa gtttcttcgc ctaacaccaa gaccataccg     120
gtcctacgct caacctctga taaggtttct gggatcactc cctcttccac acatatcggc     180
caggtcaatg cggcacgata tggcggcggt ggtggtggga tcaataccog tccgcaggcc     240 tccataggca gtgcgagcca ggatattcta gcgaagatga aggcttttca actttcaaga     300 caagggggttc ctcccaacct aaaccagtcc gtctcgacag gagcgatttc gcaaggcggt     360
caacaaagca cacccagcgt atctggtcca ttatcaggta ataactctcc ttcggccatg     420
aacggcccat tggcgccaac cgcttcaggg cggcttcctc caactcaccg tccaggacct     480
ccgaagaatt gggcttccgc tcctactgtc ggtggcggct ctcccgtgag cggctctcct     540
aaaggtggcc tggcggcgaa acgcatgaag cccggactca actatcaga tgctactgga     600 ccaagcaatc cggcagctgg aggtcagtcc ccgccggtg gaccgattgg aggtggagag     660
tcagctttca gcaagtattc ggagtacatt gacacgaaat cgggaaccct gaagttcaag     720
aacaaagccg tcctccacgg aggcgggatc gagttctcgt ccggccaaag tttcagcatc     780
tctctagatg aagtggatcg tatggatgaa ttgggcaagg gaaattacgg aactgtatac     840
```

```
aaggttcggc atagccgccc gcacatgcgc aaacctggac aaggcttgag tgggattgtc      900
agcagacctc aagggtctga cggttcagat accgaattga agccgcaaga ttccctgact      960
ggcgccgtca tggctatgaa ggagattcgg ctggagttgg acgagagcaa gtttgcgcaa     1020
atcatcatgg agttggacat cctccaccga tgtgtttcac cgttcattat cgacttctac     1080
ggtgccttct tccaggaagg tgctgtgtac atttgcgttg aattcatgga tggcggctcc     1140
gttgacaagc tttacggcga tggtataccc gagaacattc ttcgcaaagt ggcgctttct     1200
actgttatgg ggttaaagtc tctcaaggat gatcataaca tcatccacag agatgtgaaa     1260
cccacgaaca ttcttgttaa cacacgaggt caggttaaaa tttgtgactt tggagttagc     1320
ggaaatttgg ttgccagtat cgccaagacg aacataggct gccagagcta catggcacct     1380
gagcgcattg caggaggtgg agtgcagcag tcagggggcct ctggcggcac ctacagtgtc     1440
caaagtgaca tatggagctt gggattgtcc attattgaat gcgccatcgg ccggtaccct     1500
tacccccccag aaactttcaa taacatcttc agtcagctac atgccattgt gcatggtgaa     1560
gctccgaatc taccggaatc cgagtactct gaggacgcac attccttcgt cagggcgtgt     1620
cttgacaaaa accctcaaaa acgtcccaca taacatgc ttatccgaca tccttggtta     1680
tcttcattaa tgcaacctcc tgactcggat aaccctgacg taccatccgt ttctcttgca     1740
gatggcgcat ctggcgacgt cacaccacca gttacagatg atcaggaagt tgcggactgg     1800
gtcaaagata ggctggagaa acggttgaat gggcttctga agacgaaac taagccagca     1860
ctgcacgccg ttccattgga tgccgtgcct gggagcccgc ttcttgatga ccctcccatc     1920
gctaacctct cgcttgcgtc ctccatgcca gaatag                              1956
```

<210> SEQ ID NO 74
<211> LENGTH: 651
<212> TYPE: PRT
<213> ORGANISM: Aspergillus nidulans

<400> SEQUENCE: 74

```
Met Ser Ala Glu His Asp Phe Ala Ala Glu Asn Pro Pro Val Ser Pro
1               5                   10                  15

His Ser Asp Gly Asp Ser Ala Pro Val Thr Leu Glu Asp Glu Val Ser
                20                  25                  30

Ser Pro Asn Thr Lys Thr Ile Pro Val Leu Arg Ser Thr Ser Asp Lys
            35                  40                  45

Val Ser Gly Ile Thr Pro Ser Ser Thr His Ile Gly Gln Val Asn Ala
        50                  55                  60

Ala Arg Tyr Gly Gly Gly Gly Gly Ile Asn Thr Arg Pro Gln Ala
65                  70                  75                  80

Ser Ile Gly Ser Ala Ser Gln Asp Ile Leu Ala Lys Met Lys Ala Phe
                85                  90                  95

Gln Leu Ser Arg Gln Gly Val Pro Pro Asn Leu Asn Gln Ser Val Ser
                100                 105                 110

Thr Gly Ala Ile Ser Gln Gly Gly Gln Gln Ser Thr Pro Ser Val Ser
            115                 120                 125

Gly Pro Leu Ser Gly Asn Asn Ser Pro Ser Ala Met Asn Gly Pro Leu
        130                 135                 140

Ala Pro Thr Ala Ser Gly Arg Leu Pro Pro Thr His Arg Pro Gly Pro
145                 150                 155                 160

Pro Lys Asn Trp Ala Ser Ala Pro Thr Val Gly Gly Gly Ser Pro Val
                165                 170                 175

Ser Gly Ser Pro Lys Gly Gly Leu Ala Ala Lys Arg Met Lys Pro Gly
```

-continued

```
                180                 185                 190
Leu Lys Leu Ser Asp Ala Thr Gly Pro Ser Asn Pro Ala Gly Gly
            195                 200                 205
Gln Ser Pro Ala Gly Gly Pro Ile Gly Gly Glu Ser Ala Phe Ser
            210                 215                 220
Lys Tyr Ser Glu Tyr Ile Asp Thr Lys Ser Gly Thr Leu Lys Phe Lys
225                 230                 235                 240
Asn Lys Ala Val Leu His Gly Gly Ile Glu Phe Ser Ser Gly Gln
            245                 250                 255
Ser Phe Ser Ile Ser Leu Asp Glu Val Asp Arg Met Asp Glu Leu Gly
            260                 265                 270
Lys Gly Asn Tyr Gly Thr Val Tyr Lys Val Arg His Ser Arg Pro His
            275                 280                 285
Met Arg Lys Pro Gly Gln Gly Leu Ser Gly Ile Val Ser Arg Pro Gln
            290                 295                 300
Gly Ser Asp Gly Ser Asp Thr Glu Leu Lys Pro Gln Asp Ser Leu Thr
305                 310                 315                 320
Gly Ala Val Met Ala Met Lys Glu Ile Arg Leu Glu Leu Asp Glu Ser
            325                 330                 335
Lys Phe Ala Gln Ile Ile Met Glu Leu Asp Ile Leu His Arg Cys Val
            340                 345                 350
Ser Pro Phe Ile Ile Asp Phe Tyr Gly Ala Phe Phe Gln Glu Gly Ala
            355                 360                 365
Val Tyr Ile Cys Val Glu Phe Met Asp Gly Gly Ser Val Asp Lys Leu
            370                 375                 380
Tyr Gly Asp Gly Ile Pro Glu Asn Ile Leu Arg Lys Val Ala Leu Ser
385                 390                 395                 400
Thr Val Met Gly Leu Lys Ser Leu Lys Asp Asp His Asn Ile Ile His
            405                 410                 415
Arg Asp Val Lys Pro Thr Asn Ile Leu Val Asn Thr Arg Gly Gln Val
            420                 425                 430
Lys Ile Cys Asp Phe Gly Val Ser Gly Asn Leu Val Ala Ser Ile Ala
            435                 440                 445
Lys Thr Asn Ile Gly Cys Gln Ser Tyr Met Ala Pro Glu Arg Ile Ala
            450                 455                 460
Gly Gly Gly Val Gln Gln Ser Gly Ala Ser Gly Thr Tyr Ser Val
465                 470                 475                 480
Gln Ser Asp Ile Trp Ser Leu Gly Leu Ser Ile Ile Glu Cys Ala Ile
            485                 490                 495
Gly Arg Tyr Pro Tyr Pro Pro Glu Thr Phe Asn Asn Ile Phe Ser Gln
            500                 505                 510
Leu His Ala Ile Val His Gly Glu Ala Pro Asn Leu Pro Glu Ser Glu
            515                 520                 525
Tyr Ser Glu Asp Ala His Ser Phe Val Arg Ala Cys Leu Asp Lys Asn
            530                 535                 540
Pro Gln Lys Arg Pro Thr Tyr Asn Met Leu Ile Arg His Pro Trp Leu
545                 550                 555                 560
Ser Ser Leu Met Gln Pro Pro Asp Ser Asp Asn Pro Asp Val Pro Ser
            565                 570                 575
Val Ser Leu Ala Asp Gly Ala Ser Gly Asp Val Thr Pro Pro Val Thr
            580                 585                 590
Asp Asp Gln Glu Val Ala Asp Trp Val Lys Asp Arg Leu Glu Lys Arg
            595                 600                 605
```

```
Leu Asn Gly Leu Leu Lys Asp Glu Thr Lys Pro Ala Leu His Ala Val
    610                 615                 620

Pro Leu Asp Ala Val Pro Gly Ser Pro Leu Leu Asp Asp Pro Pro Ile
625                 630                 635                 640

Ala Asn Leu Ser Leu Ala Ser Ser Met Pro Glu
                645                 650

<210> SEQ ID NO 75
<211> LENGTH: 2058
<212> TYPE: DNA
<213> ORGANISM: Magnaportha grisea

<400> SEQUENCE: 75
atgtcacaat cgcaacaacc accggcaacg ggccgggata attcggtccc tgctactccg     60
gacgaacagt ttgacagcat gcccacctcg ccatgctcca ttgtggacga cgactcggag    120
gcgagcactc cactagaccc gccatcaccg agtgccctcc cgaaacgagt cccgtccctc    180
cggactgtct ccgatccatc tacgacggca atgacatcta cgtctacagt gacggggacc    240
ctcaccaatg cgcgtaggcc ccctccgtct gctggagttc tgcctgccga cctgatggca    300
aaggcacgcg cactacaaag tacacgcatg gggcggccgc agatgcaggc gtttggcagc    360
ggcagtagca cgtcttctgc ctcggggatt ggctccccgt tacccatggg ctccggtctc    420
gggccacaat cgccgcctgt gggcctaccc acgggaggta tgtctggaaa catgcgcttt    480
ccgcccaaca tcgccgccaa catgcagctg aacttgggcg ggcgtccact cccgcagggc    540
ttccccaagt cggctccggc cgtaccgagc gcacgcaaag ctccccccag cctgagcgag    600
aggagagcca tgaagctagg cggccttccg ggtggacctg gcgctacgcc tagcatggga    660
acccccaagc tgtctgacct gcaaggtgga gcatcggggc caacagatgg caacagtaac    720
gcagacaaga cgtcaggagc tggtgggcaa gcggttccgg acaacaagct gcacgacttt    780
aagcagtaca tcgatgcgga gaatggctgg atcacgtttg acggcgcggc aacgatcacg    840
cgcacaggcg tcaactttgc aagtggacac aaattcagca tctcgctcga cgagatacaa    900
gttctcgatg aactcggcaa gggaaactac ggtacagtgt acaaggtccg acatgccaag    960
cccaaggttc cccggtttgg acagggtctt ggcagcctga cgaaacagtc agtatcacga   1020
cagaactcga tgaaggacga aggagaggat gcgaacggcg ttgttgatgg ccagacgacc   1080
tccggtgttg tgatggccat gaaggagatc aggctagaac tggacgaggc caagtttacg   1140
accatcctca aggagctagt tatcctgcac gaatgcgtgt cgccgtacat catcgacttc   1200
tatggcgcct ttttccaaga aggagctgtg tatatgtgca tagagtacat ggacggtggc   1260
tccatcgaca agttgtacgc tggcgggatc ccagagggcg ttattcgcaa gattacgtat   1320
gcgacggtca tgggcctcaa gtcgctcaag gacgatcaca acatcattca tcgcgacgtc   1380
aaaccaacca acatcctcgc aaatacccgc ggacaggtca agatttgcga ctttggtgta   1440
agcggtaatc tggtggcgtc tatcgccaag accaacatcg gatgccagag ctacatggca   1500
cccgagagga tatcgggagg aggtttcgca caaggaggtg cggacggcac atacaacgtg   1560
caaagcgata tctggagctt aggcttgacc atcatcgagt gcgccatggg caggtatcca   1620
tacccacctg aggtgtcgtc gacaatcttc agccaactga gcgccattgt tgagggtgac   1680
ccgcctgacc taccaaccga gggctattct gatacggcgc gcaattttgt gcggtcatgt   1740
ctagataaga acccggcgaa gaggagtacg tacccaatgc tcctagccca cccatggctc   1800
aggtccctgg cacagccggc gacaatcagc gaggaggcgg aagataccga agacctcgag   1860
gcggcggcgc aaaagctgtc attaggcgct ggacccattg ggccgacga cgaggtggct     1920
```

```
cagtgggtca agtcagccct agacaggaaa cgcagagggg acgcacaaag tcccgacaag   1980
ccagcacttc atgctgcccc ctttgatagc gccagtccaa tggcagcacc gaaggctggc   2040
ccgatgacgg gtgcttaa                                                  2058
```

<210> SEQ ID NO 76
<211> LENGTH: 685
<212> TYPE: PRT
<213> ORGANISM: Magnaportha grisea

<400> SEQUENCE: 76

```
Met Ser Gln Ser Gln Gln Pro Pro Ala Thr Gly Arg Asp Asn Ser Val
1               5                   10                  15

Pro Ala Thr Pro Asp Glu Gln Phe Asp Ser Met Pro Thr Ser Pro Cys
            20                  25                  30

Ser Ile Val Asp Asp Asp Ser Glu Ala Ser Thr Pro Leu Asp Pro Pro
        35                  40                  45

Ser Pro Ser Ala Leu Pro Lys Arg Val Pro Ser Leu Arg Thr Val Ser
    50                  55                  60

Asp Pro Ser Thr Thr Ala Met Thr Ser Thr Ser Thr Val Thr Gly Thr
65                  70                  75                  80

Leu Thr Asn Ala Arg Arg Pro Pro Ser Ala Gly Val Leu Pro Ala
                85                  90                  95

Asp Leu Met Ala Lys Ala Arg Ala Leu Gln Ser Thr Arg Met Gly Arg
            100                 105                 110

Pro Gln Met Gln Ala Phe Gly Ser Gly Ser Ser Thr Ser Ser Ala Ser
        115                 120                 125

Gly Ile Gly Ser Pro Leu Pro Met Gly Ser Gly Leu Gly Pro Gln Ser
    130                 135                 140

Pro Pro Val Gly Leu Pro Thr Gly Gly Met Ser Gly Asn Met Arg Phe
145                 150                 155                 160

Pro Pro Asn Ile Ala Ala Asn Met Gln Leu Asn Leu Gly Gly Arg Pro
                165                 170                 175

Leu Pro Gln Gly Phe Pro Lys Ser Ala Pro Ala Val Pro Ser Ala Arg
            180                 185                 190

Lys Ala Pro Pro Ser Leu Ser Glu Arg Arg Ala Met Lys Leu Gly Gly
        195                 200                 205

Leu Pro Gly Gly Pro Gly Ala Thr Pro Ser Met Gly Thr Pro Lys Leu
    210                 215                 220

Ser Asp Leu Gln Gly Gly Ala Ser Gly Pro Thr Asp Gly Asn Ser Asn
225                 230                 235                 240

Ala Asp Lys Thr Ser Gly Ala Gly Gln Ala Val Pro Asp Asn Lys
                245                 250                 255

Leu His Asp Phe Lys Gln Tyr Ile Asp Ala Glu Asn Gly Trp Ile Thr
            260                 265                 270

Phe Asp Gly Ala Ala Thr Ile Thr Arg Thr Gly Val Asn Phe Ala Ser
        275                 280                 285

Gly His Lys Phe Ser Ile Ser Leu Asp Glu Ile Gln Val Leu Asp Glu
    290                 295                 300

Leu Gly Lys Gly Asn Tyr Gly Thr Val Tyr Lys Val Arg His Ala Lys
305                 310                 315                 320

Pro Lys Val Pro Arg Phe Gly Gln Gly Leu Gly Ser Leu Thr Lys Gln
                325                 330                 335

Ser Val Ser Arg Gln Asn Ser Met Lys Asp Glu Gly Glu Asp Ala Asn
            340                 345                 350
```

Gly Val Val Asp Gly Gln Thr Thr Ser Gly Val Val Met Ala Met Lys
            355                 360                 365

Glu Ile Arg Leu Glu Leu Asp Glu Ala Lys Phe Thr Thr Ile Leu Lys
        370                 375                 380

Glu Leu Val Ile Leu His Glu Cys Val Ser Pro Tyr Ile Ile Asp Phe
385                 390                 395                 400

Tyr Gly Ala Phe Phe Gln Glu Gly Ala Val Tyr Met Cys Ile Glu Tyr
                405                 410                 415

Met Asp Gly Gly Ser Ile Asp Lys Leu Tyr Ala Gly Gly Ile Pro Glu
            420                 425                 430

Gly Val Ile Arg Lys Ile Thr Tyr Ala Thr Val Met Gly Leu Lys Ser
        435                 440                 445

Leu Lys Asp Asp His Asn Ile Ile His Arg Asp Val Lys Pro Thr Asn
450                 455                 460

Ile Leu Ala Asn Thr Arg Gly Gln Val Lys Ile Cys Asp Phe Gly Val
465                 470                 475                 480

Ser Gly Asn Leu Val Ala Ser Ile Ala Lys Thr Asn Ile Gly Cys Gln
                485                 490                 495

Ser Tyr Met Ala Pro Glu Arg Ile Ser Gly Gly Phe Ala Gln Gly
            500                 505                 510

Gly Ala Asp Gly Thr Tyr Asn Val Gln Ser Asp Ile Trp Ser Leu Gly
        515                 520                 525

Leu Thr Ile Ile Glu Cys Ala Met Gly Arg Tyr Pro Tyr Pro Pro Glu
530                 535                 540

Val Ser Ser Thr Ile Phe Ser Gln Leu Ser Ala Ile Val Glu Gly Asp
545                 550                 555                 560

Pro Pro Asp Leu Pro Thr Glu Gly Tyr Ser Asp Thr Ala Arg Asn Phe
                565                 570                 575

Val Arg Ser Cys Leu Asp Lys Asn Pro Ala Lys Arg Ser Thr Tyr Pro
            580                 585                 590

Met Leu Leu Ala His Pro Trp Leu Arg Ser Leu Ala Gln Pro Ala Thr
        595                 600                 605

Ile Ser Glu Glu Ala Glu Asp Thr Glu Asp Leu Glu Ala Ala Ala Gln
610                 615                 620

Lys Leu Ser Leu Gly Ala Gly Pro Ile Gly Ala Asp Asp Glu Val Ala
625                 630                 635                 640

Gln Trp Val Lys Ser Ala Leu Asp Arg Lys Arg Gly Asp Ala Gln
                645                 650                 655

Ser Pro Asp Lys Pro Ala Leu His Ala Ala Pro Phe Asp Ser Ala Ser
            660                 665                 670

Pro Met Ala Ala Pro Lys Ala Gly Pro Met Thr Gly Ala
        675                 680                 685

<210> SEQ ID NO 77
<211> LENGTH: 1830
<212> TYPE: DNA
<213> ORGANISM: Cryptococcus neoformans

<400> SEQUENCE: 77
atgacagacc ctacgcctcc cgcgctcgac agtctctccc tggcagacaa ggcccctgct      60
gccgaagaaa atccccgaga cgccgccgaa cagcccaagc ccgccgcctc accgccgca     120 ggcacgcccg ttgatgacgc ccaaaagctca tccgcctcgc cctcccagcg cccgccgtcc    180
atacaggcaa atgacaaggc cccgggtaca tcgtctccgg ctgccaggcc gcaagcacag    240

```
catgtccctg catcggcacc caccgtccct tccgccaacc ccgtccgtcc gcagcctggc    300
gcccggcctg gagtggcgag gggtatgcct gcgccaatgg ggatgcgggc gcaggcagtt    360
cgaggcgctg gcgggcccca gatgcagacc aagatgctgc ccagtttaca ggctaaaatg    420
gacaagatcg ccgcgtcccg tcaaggcccg cctccctcct ccggcatgca tgatccgaat    480
gccacgtcca tgggcgccct cttgcgctcc caagccctcc gggcgcccgg cacatcgcaa    540
gctcctcctg gccccgggcc ggcttcaggt cctttcggtc tcgccgctcg gcgcgcagct    600
gctggaggtc ctcccagacc gaatttgggt atgatgggta tggggggcaag tgcgccgagt    660 gcggtcggac gaggaccagg tctggcgggc agacggggac ccccgggagg attgacactg    720
agtgggatga agggtgcgat caaggacgat gggaacaagt tttcagactt tcagggtgtc    780
atggaccctt ccggatcgct gagattctca agaaggccg tcctgcatgc aaagggcgtg    840
gactttgacg atgggcagag tttcaagatc aacatggatg agatcgaggt gctcggagaa    900
ctaggaaagg gcaattacgg ttctgtccac aaggtcttcc accgtccgac aggcgtcacc    960
atggccatga aggaaatccg gttagaactt gatgattcca agctcaacgg catcattatg    1020
gaactcgaca ttctacaccg gccgtcgct cccgaaatag tcgaattcta cggtgcattc    1080
accattgaat cctgcgtcta ctactgtatg gagtacatgg atgccggctc actcgattcc    1140
ctcactggtg gcggtgtggc agccaaagat cagacaaagg aggaagaaga cgatgcgaca    1200
gagcgagtgc cagaggatgt attgaggagg attacagcga gaatcgtaaa agggttgaga    1260
ttcttgaagg atgagttgca gatcatccat cgagacgtca acccacaaa tgtgttgatc    1320 aatggcaagg gagaggtcaa gatgtgtgac tttggtgtct caggtcagct cgaaaagagt    1380
ttggccaaga ctaatatcgg ttgccaatcc tacatggctc ccgaacgtat caagtcggaa    1440
acagccaacc aaaatcctac ttacactgtc tcctcagacg tctggtcggt cggtctgtcc    1500
attgtcgagc ttgccaaagg atgttacccc tacccaccgg aaacgtatgc gaatgtgttt    1560
gcgcagttgc aggcgattgt acatggcact ccgccaacgt tgcccctgg gtacagcgat    1620 gacgcgaacg atttcgttgc caagtgtctt gagaaggatc ccaaccgacg accgacttat    1680
gctcagctct tagaacatcc tttcttggta gcggacaagg gcgcagaagt cgacatggtt    1740
ggatgggtgg aagggcgtt gaagcgtaag gcggagagag gaattgcgag cctgaatcct    1800
atccaaacac ctgccctct ggaaccataa                                       1830
```

<210> SEQ ID NO 78
<211> LENGTH: 609
<212> TYPE: PRT
<213> ORGANISM: Cryptococcus neoformans

<400> SEQUENCE: 78

```
Met Thr Asp Pro Thr Pro Pro Ala Leu Asp Ser Leu Ser Leu Ala Asp
1               5                   10                  15

Lys Ala Pro Ala Ala Glu Glu Asn Pro Arg Asp Ala Ala Glu Gln Pro
            20                  25                  30

Lys Pro Ala Ala Ser Pro Pro Ala Gly Thr Pro Val Asp Asp Ala Gln
        35                  40                  45

Ser Ser Ala Ser Pro Ser Gln Arg Pro Pro Ser Ile Gln Ala Asn
    50                  55                  60

Asp Lys Ala Pro Gly Thr Ser Ser Pro Ala Ala Arg Pro Gln Ala Gln
65                  70                  75                  80

His Val Pro Ala Ser Ala Pro Thr Val Pro Ser Ala Asn Pro Val Arg
                85                  90                  95
```

```
Pro Gln Pro Gly Ala Arg Pro Gly Val Ala Arg Gly Met Pro Ala Pro
            100                 105                 110

Met Gly Met Arg Ala Gln Ala Val Arg Gly Ala Gly Pro Gln Met
        115                 120                 125

Gln Thr Lys Met Leu Pro Ser Leu Gln Ala Lys Met Asp Lys Ile Ala
130                 135                 140

Ala Ser Arg Gln Gly Pro Pro Ser Ser Gly Met His Asp Pro Asn
145                 150                 155                 160

Ala Thr Ser Met Gly Ala Leu Leu Arg Ser Gln Ala Leu Arg Ala Pro
                165                 170                 175

Gly Thr Ser Gln Ala Pro Pro Gly Pro Gly Pro Ala Ser Gly Pro Phe
            180                 185                 190

Gly Leu Ala Ala Arg Arg Ala Ala Ala Gly Gly Pro Pro Arg Pro Asn
        195                 200                 205

Leu Gly Met Met Gly Met Gly Ala Ser Ala Pro Ser Ala Val Gly Arg
    210                 215                 220

Gly Pro Gly Leu Ala Gly Arg Arg Gly Pro Pro Gly Gly Leu Thr Leu
225                 230                 235                 240

Ser Gly Met Lys Gly Ala Ile Lys Asp Asp Gly Asn Lys Phe Ser Asp
                245                 250                 255

Phe Gln Gly Val Met Asp Pro Ser Gly Ser Leu Arg Phe Ser Lys Lys
            260                 265                 270

Ala Val Leu His Ala Lys Gly Val Asp Phe Asp Gly Gln Ser Phe
        275                 280                 285

Lys Ile Asn Met Asp Glu Ile Glu Val Leu Gly Glu Leu Gly Lys Gly
    290                 295                 300

Asn Tyr Gly Ser Val His Lys Val Phe His Arg Pro Thr Gly Val Thr
305                 310                 315                 320

Met Ala Met Lys Glu Ile Arg Leu Glu Leu Asp Asp Ser Lys Leu Asn
                325                 330                 335

Gly Ile Ile Met Glu Leu Asp Ile Leu His Arg Ala Val Ala Pro Glu
            340                 345                 350

Ile Val Glu Phe Tyr Gly Ala Phe Thr Ile Glu Ser Cys Val Tyr Tyr
        355                 360                 365

Cys Met Glu Tyr Met Asp Ala Gly Ser Leu Asp Ser Leu Thr Gly Gly
    370                 375                 380

Gly Val Ala Ala Lys Asp Gln Thr Lys Glu Glu Asp Asp Ala Thr
385                 390                 395                 400

Glu Arg Val Pro Glu Asp Val Leu Arg Arg Ile Thr Ala Arg Ile Val
                405                 410                 415

Lys Gly Leu Arg Phe Leu Lys Asp Glu Leu Gln Ile Ile His Arg Asp
            420                 425                 430

Val Lys Pro Thr Asn Val Leu Ile Asn Gly Lys Gly Glu Val Lys Met
        435                 440                 445

Cys Asp Phe Gly Val Ser Gly Gln Leu Glu Lys Ser Leu Ala Lys Thr
    450                 455                 460

Asn Ile Gly Cys Gln Ser Tyr Met Ala Pro Glu Arg Ile Lys Ser Glu
465                 470                 475                 480

Thr Ala Asn Gln Asn Pro Thr Tyr Thr Val Ser Ser Asp Val Trp Ser
                485                 490                 495

Val Gly Leu Ser Ile Val Glu Leu Ala Lys Gly Cys Tyr Pro Tyr Pro
            500                 505                 510

Pro Glu Thr Tyr Ala Asn Val Phe Ala Gln Leu Gln Ala Ile Val His
        515                 520                 525
```

Gly Thr Pro Pro Thr Leu Pro Pro Gly Tyr Ser Asp Asp Ala Asn Asp
        530                 535                 540

Phe Val Ala Lys Cys Leu Glu Lys Asp Pro Asn Arg Arg Pro Thr Tyr
545                 550                 555                 560

Ala Gln Leu Leu Glu His Pro Phe Leu Val Ala Asp Lys Gly Ala Glu
                565                 570                 575

Val Asp Met Val Gly Trp Val Glu Gly Ala Leu Lys Arg Lys Ala Glu
            580                 585                 590

Arg Gly Ile Ala Ser Leu Asn Pro Ile Gln Thr Pro Ala Pro Leu Glu
        595                 600                 605

Pro

<210> SEQ ID NO 79
<211> LENGTH: 933
<212> TYPE: DNA
<213> ORGANISM: Ustilago maydis

<400> SEQUENCE: 79
atggccgagc ttgagctcat ggacgagctc ggcaagggca actacggtac cgttcgcaag      60
gtgcgtcaca cgcagacgca tgtcgagatg gcgatgaagg agattcgtct cgagttggac     120
gagtcgaagc tcaatgccat catcatggag ctcgacattc tgcatcgagc cactgcaccg     180
cagattgtcg agttttacgg cgccttcttt atcgagtcgt gcgtctacta ttgcatggag     240
tacatgaacg cgggcagtct cgacaagctg tacggcgacc ggggcagcgt gcctgaagat     300
gtgcttgcaa ggatcactgg cagcatggtg cgtggtctca gcttcctcaa agatgagctg     360
cagatcatgc accgcgacgt caagcccacc aatgtgctca tcaatcgcaa gggtcaggtc     420
aagctgtgcg actttggcgt ttcgggtcaa ttggaaaagt cgttggccaa gaccaacatt     480
ggctgtcagt cgtacatggc gcccgaacgc atcaagggcg aatcgcaaaa catgctgggc     540
acctacaccg tggcctcgga cgtgtggtcg ctcggattgt ccatggtcga gacgacgctc     600
ggcacctatc cgtatccgcc cgaaacctac tcgaacgttt ttgcacagct ccaggccatc     660
gtgcatggcg atcctcccga attgcctccc gagctgtact ccgagacggc gcgcgacttt     720
gtagcaaagt gcctggaaaa gattccagct cgaaggccaa cgtatgcaca gttgctcgag     780
cacgagtttc ttacggagga tgcggccaaa ggcgaggaag cgtcgacat ggtcgggtgg      840 gtggaaaggg ccattgatgc gagaacacgg aaaaaggagc aggtcaatgg tacttcagct     900
cctggttcat cttcaacacc atcagaggca tga                                   933

<210> SEQ ID NO 80
<211> LENGTH: 310
<212> TYPE: PRT
<213> ORGANISM: Ustilago maydis

<400> SEQUENCE: 80

Met Ala Glu Leu Glu Leu Met Asp Glu Leu Gly Lys Gly Asn Tyr Gly
1               5                   10                  15

Thr Val Arg Lys Val Arg His Thr Gln Thr His Val Glu Met Ala Met
            20                  25                  30

Lys Glu Ile Arg Leu Glu Leu Asp Glu Ser Lys Leu Asn Ala Ile Ile
        35                  40                  45

Met Glu Leu Asp Ile Leu His Arg Ala Thr Ala Pro Gln Ile Val Glu
    50                  55                  60

Phe Tyr Gly Ala Phe Phe Ile Glu Ser Cys Val Tyr Tyr Cys Met Glu
65                  70                  75                  80

```
Tyr Met Asn Ala Gly Ser Leu Asp Lys Leu Tyr Gly Asp Arg Gly Ser
            85                  90                  95

Val Pro Glu Asp Val Leu Ala Arg Ile Thr Gly Ser Met Val Arg Gly
        100                 105                 110

Leu Ser Phe Leu Lys Asp Glu Leu Gln Ile Met His Arg Asp Val Lys
    115                 120                 125

Pro Thr Asn Val Leu Ile Asn Arg Lys Gly Gln Val Lys Leu Cys Asp
130                 135                 140

Phe Gly Val Ser Gly Gln Leu Glu Lys Ser Leu Ala Lys Thr Asn Ile
145                 150                 155                 160

Gly Cys Gln Ser Tyr Met Ala Pro Glu Arg Ile Lys Gly Glu Ser Gln
                165                 170                 175

Asn Met Leu Gly Thr Tyr Thr Val Ala Ser Asp Val Trp Ser Leu Gly
            180                 185                 190

Leu Ser Met Val Glu Thr Thr Leu Gly Thr Tyr Pro Tyr Pro Pro Glu
        195                 200                 205

Thr Tyr Ser Asn Val Phe Ala Gln Leu Gln Ala Ile Val His Gly Asp
    210                 215                 220

Pro Pro Glu Leu Pro Pro Glu Leu Tyr Ser Glu Thr Ala Arg Asp Phe
225                 230                 235                 240

Val Ala Lys Cys Leu Glu Lys Ile Pro Ala Arg Arg Pro Thr Tyr Ala
                245                 250                 255

Gln Leu Leu Glu His Glu Phe Leu Thr Glu Asp Ala Ala Lys Gly Glu
            260                 265                 270

Glu Gly Val Asp Met Val Gly Trp Val Glu Arg Ala Ile Asp Ala Arg
        275                 280                 285

Thr Arg Lys Lys Glu Gln Val Asn Gly Thr Ser Ala Pro Gly Ser Ser
    290                 295                 300

Ser Thr Pro Ser Glu Ala
305                 310

<210> SEQ ID NO 81
<211> LENGTH: 23
<212> TYPE: DNA
<213> ORGANISM: artificial sequence
<220> FEATURE:
<223> OTHER INFORMATION: primer

<400> SEQUENCE: 81
ctatgcgcac ccgttctcgg agc                                             23

<210> SEQ ID NO 82
<211> LENGTH: 22
<212> TYPE: DNA
<213> ORGANISM: artificial sequence
<220> FEATURE:
<223> OTHER INFORMATION: primer

<400> SEQUENCE: 82
cgctcatgag cccgaagtgg cg                                              22

<210> SEQ ID NO 83
<211> LENGTH: 43
<212> TYPE: DNA
<213> ORGANISM: artificial sequence
<220> FEATURE:
<223> OTHER INFORMATION: primer

<400> SEQUENCE: 83
```

-continued

```
ccgctgctag gcgcgccgtg tctgaaaacg gaagaggagt agg          43
```

<210> SEQ ID NO 84
<211> LENGTH: 44
<212> TYPE: DNA
<213> ORGANISM: artificial sequence
<220> FEATURE:
<223> OTHER INFORMATION: primer

<400> SEQUENCE: 84

```
gcagggatgc ggccgctgac ataacagaca tactccaagc tgcc          44
```

<210> SEQ ID NO 85
<211> LENGTH: 45
<212> TYPE: DNA
<213> ORGANISM: artificial sequence
<220> FEATURE:
<223> OTHER INFORMATION: primer

<400> SEQUENCE: 85

```
ccgctgctag gcgcgccgtg catttggctt tttgattgat tgtac          45
```

<210> SEQ ID NO 86
<211> LENGTH: 47
<212> TYPE: DNA
<213> ORGANISM: artificial sequence
<220> FEATURE:
<223> OTHER INFORMATION: primer

<400> SEQUENCE: 86

```
gcagggatgc ggccgctgac acttttattt tctcttttg cactcct          47
```

<210> SEQ ID NO 87
<211> LENGTH: 20
<212> TYPE: DNA
<213> ORGANISM: artificial sequence
<220> FEATURE:
<223> OTHER INFORMATION: primer

<400> SEQUENCE: 87

```
ccgctgctag gcgcgccgtg                                      20
```

<210> SEQ ID NO 88
<211> LENGTH: 25
<212> TYPE: DNA
<213> ORGANISM: artificial sequence
<220> FEATURE:
<223> OTHER INFORMATION: primer

<400> SEQUENCE: 88

```
gagcaatgaa cccaataacg aaatc                                25
```

<210> SEQ ID NO 89
<211> LENGTH: 20
<212> TYPE: DNA
<213> ORGANISM: artificial sequence
<220> FEATURE:
<223> OTHER INFORMATION: primer

<400> SEQUENCE: 89

```
gcagggatgc ggccgctgac                                      20
```

<210> SEQ ID NO 90
<211> LENGTH: 25
<212> TYPE: DNA

<213> ORGANISM: artificial sequence
<220> FEATURE:
<223> OTHER INFORMATION: primer

<400> SEQUENCE: 90
cttgacgttc gttcgactga tgagc    25

<210> SEQ ID NO 91
<211> LENGTH: 448
<212> TYPE: DNA
<213> ORGANISM: Saccharomyces cerevisiae

<400> SEQUENCE: 91
cccattaccg acatttgggc gctatacgtg catatgttca tgtatgtatc tgtatttaaa    60
acacttttgt attattttc ctcatatatg tgtataggtt tatacggatg atttaattat    120
tacttcacca cccttatt caggctgata tcttagcctt gttactagtt agaaaaagac    180
atttttgctg tcagtcactg tcaagagatt cttttgctgg catttcttct agaagcaaaa    240
agagcgatgc gtcttttccg ctgaaccgtt ccagcaaaaa agactaccaa cgcaatatgg    300
attgtcagaa tcatataaaa gagaagcaaa taactccttg tcttgtatca attgcattat    360
aatatcttct tgttagtgca atatcatata gaagtcatcg aaatagatat taagaaaaac    420
aaactgtaca atcaatcaat caatcatc    448

<210> SEQ ID NO 92
<211> LENGTH: 270
<212> TYPE: DNA
<213> ORGANISM: Saccharomyces cerevisiae

<400> SEQUENCE: 92
gacctcgagt catgtaatta gttatgtcac gcttacattc acgccctccc cccacatccg    60
ctctaaccga aaaggaagga gttagacaac ctgaagtcta ggtccctatt tattttttta    120
tagttatgtt agtattaaga acgttattta tatttcaaat ttttcttttt tttctgtaca    180
gacgcgtgta cgcatgtaac attatactga aaaccttgct tgagaaggtt ttgggacgct    240
cgaaggcttt aatttgcggc cggtacccaa    270

<210> SEQ ID NO 93
<211> LENGTH: 643
<212> TYPE: DNA
<213> ORGANISM: Saccharomyces cerevisiae

<400> SEQUENCE: 93
gaaatgaata acaatactga cagtactaaa taattgccta cttggcttca catacgttgc    60
atacgtcgat atagataata atgataatga cagcaggatt atcgtaatac gtaatagttg    120
aaaatctcaa aaatgtgtgg gtcattacgt aaataatgat aggaatggga ttcttctatt    180 ttccttttt ccattctagc agccgtcggg aaaacgtggc atcctctctt tcgggctcaa    240
ttggagtcac gctgccgtga gcatcctctc tttccatatc taacaactga gcacgtaacc    300
aatggaaaag catgagctta gcgttgctcc aaaaaagtat tggatggtta ataccatttg    360
tctgttctct tctgactttg actcctcaaa aaaaaaaat ctacaatcaa cagatcgctt    420
caattacgcc ctcacaaaaa cttttttcct tcttcttcgc ccacgttaaa ttttatccct    480
catgttgtct aacggatttc tgcacttgat ttattataaa aagacaaaga cataatactt    540
ctctatcaat ttcagttatt gttcttcctt gcgttattct tctgttcttc tttttctttt    600

```
gtcatatata accataacca agtaatacat attcaaatct aga                       643
```

<210> SEQ ID NO 94
<211> LENGTH: 316
<212> TYPE: DNA
<213> ORGANISM: Saccharomyces cerevisiae

<400> SEQUENCE: 94

```
gagtaagcga atttcttatg atttatgatt tttattatta aataagttat aaaaaaaata     60
agtgtataca aattttaaag tgactcttag gttttaaaac gaaaattctt attcttgagt    120
aactctttcc tgtaggtcag gttgctttct caggtatagc atgaggtcgc tcttattgac   180
cacacctcta ccggcatgcc gagcaaatgc ctgcaaatcg ctccccattt cacccaattg   240
tagatatgct aactccagca atgagttgat gaatctcggt gtgtattta tgtcctcaga    300
ggacaacacc tgtggt                                                   316
```

<210> SEQ ID NO 95
<211> LENGTH: 753
<212> TYPE: DNA
<213> ORGANISM: Saccharomyces cerevisiae

<400> SEQUENCE: 95

```
gcatgcttgc atttagtcgt gcaatgtatg actttaagat ttgtgagcag gaagaaaagg    60
gagaatcttc taacgataaa cccttgaaaa actgggtaga ctacgctatg ttgagttgct   120
acgcaggctg cacaattaca cgagaatgct cccgcctagg atttaaggct aagggacgtg   180
caatgcagac gacagatcta aatgaccgtg tcggtgaagt gttcgccaaa cttttcggtt   240
aacacatgca gtgatgcacg cgcgatggtg ctaagttaca tatatatata tatagccata   300
gtgatgtcta agtaacctt atggtatatt tcttaatgtg gaaagatact agcgcgcgca    360
cccacacaca agcttcgtct tttcttgaag aaaagaggaa gctcgctaaa tgggattcca   420
cttttccgttc cctgccagct gatggaaaaa ggttagtgga acgatgaaga ataaaaagag   480
agatccactg aggtgaaatt tcagctgaca gcgagtttca tgatcgtgat gaacaatggt   540
aacgagttgt ggctgttgcc agggagggtg gttctcaact tttaatgtat ggccaaatcg   600
ctacttgggt ttgttatata acaaagaaga aataatgaac tgattctctt cctccttctt   660
gtcctttctt aattctgttg taattacctt cctttgtaat ttttttgta attattcttc   720
ttaataatcc aaacaaacac acatattaca ata                                753
```

<210> SEQ ID NO 96
<211> LENGTH: 33
<212> TYPE: DNA
<213> ORGANISM: artificial sequence
<220> FEATURE:
<223> OTHER INFORMATION: primer

<400> SEQUENCE: 96

```
ccatggtgga tccgtttgtc ttttactgcg gga                                 33
```

<210> SEQ ID NO 97
<211> LENGTH: 32
<212> TYPE: DNA
<213> ORGANISM: artificial sequence
<220> FEATURE:
<223> OTHER INFORMATION: primer

<400> SEQUENCE: 97

```
ccatggggat ccatatagca ggattgaagt ta                                  32
```

YEAST WITH INCREASED BUTANOL TOLERANCE INVOLVING HIGH OSMOLARITY/GLYCEROL RESPONSE PATHWAY

CROSS REFERENCE TO RELATED APPLICATIONS

This application is related to and claims the benefit of priority of U.S. Provisional Patent Application No. 61/141,012, filed Dec. 29, 2008, the entirety of which is herein incorporated by reference.

FIELD OF THE INVENTION

The invention relates to the field of microbiology and genetic engineering. More specifically, yeast genes that are involved in the cell response to butanol were identified. These genes may be engineered to improve growth yield in the presence of butanol.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Butanol may be made through chemical synthesis or by fermentation. Isobutanol is produced biologically as a by-product of yeast fermentation. It is a component of "fusel oil" that forms as a result of incomplete metabolism of amino acids by this group of fungi. Isobutanol is specifically produced from catabolism of L-valine and the yield is typically very low. Additionally, recombinant microbial production hosts, expressing a 1-butanol biosynthetic pathway (Donaldson et al., U.S. Patent Application Publication No. US20080182308A1), a 2-butanol biosynthetic pathway (Donaldson et al., U.S. Patent Publication Nos. US 20070259410A1 and US 20070292927), and an isobutanol biosynthetic pathway (Maggio-Hall et al., U.S. Patent Publication No. US 20070092957) have been described.

Biological production of butanols is believed to be limited by butanol toxicity to the host microorganism used in fermentation for butanol production. Yeast are typically sensitive to butanol in the medium. Using a screen for 1-butanol insensitive *Saccharomyces cerevisiae* mutants, Lorenz et al. (Molec. Biol. of the Cell (2000) 11:183-199) identified proteins that regulate polarized growth (BUD8, BEM1, BEM4, and FIG1), mitochondrial function (MSM1, MRP21, and HM11), and a transcriptional regulator (CHD1). They also found that 1-butanol stimulates filamentous growth in haploid cells and induces cell elongation and changes in budding pattern, leading to a pseudohyphal morphology. Ashe et al. (The EMBO Journal (2001) 20:6464-6474) found that butanol brings about a rapid inhibition of translation at the initiation step in *Saccharomyces cerevisiae*. The GCD1-P180 allele has a single amino acid change in Gcd1p, which is part of the eIF2B guanine nucleotide complex that is responsible for recycling eIF2-GDP to eIF2-GTP, that allows translational regulation upon butanol addition. Smirnova et al. (Molecular and Cellular Bioloty (2005) 25:9340-9340) found by using microarray analysis that with addition of fusel alcohol, there is widespread translational reprogramming in yeast. These studies all indicate the complexity of butanol sensitivity in yeast.

A complete set of *S. cerevisiae* homozygous deletions was screened for tolerance to the aliphatic alcohols ethanol, propanol and pentanol (Fuijta et al. (2006) FEMS Yeast Res 6:744-750). The set was also screened for ethanol tolerance by van Voorst et al. ((2006) *Yeast* 23(5): 351-359). Mutant PBS2 deletion strains were not found to be hypersensitive to ethanol, propanol or pentanol. These screens also did not find other components of the high osmolarity/glycerol (HOG) cascade. In contrast PBS2 deletion strains are hypersensitive to many other chemicals including 2-mercaptoethanol, dithiothreitol, $CaCl_2$, NaCl, sorbitol, sodium metaarsenite, tunicamycin and nocodazole.

There remains a need for yeast cells with increased tolerance to butanol, as well as methods of producing butanols using yeast host strains that are more tolerant to these chemicals. To this end applicants have Identified genes in yeast that are involved in butanol tolerance, that can be engineered to increase the level of butanol tolerance in yeast cells used for butanol production.

SUMMARY OF THE INVENTION

Provided herein are recombinant yeast cells comprising: a) a butanol biosynthetic pathway; and b) at least one genetic modification which increases activity of the high osmolarity/glycerol response pathway: wherein the butanol biosynthetic pathway comprises at least one gene that is heterologous to the yeast cell and wherein the yeast cell has an increase in tolerance to butanol as compared with a yeast cell that lacks the at least one genetic modification of (b).

In some embodiments, the cell has at least about a 40% improvement in growth yield in 1% (w/v) isobutanol as compared to a parental cell having no increase in activity of the high osmolarity/glycerol response pathway.

In some embodiments, the yeast is selected from the group consisting of *Saccharomyces*, *Schizosaccharomyces*, *Hansenula*, *Candida*, *Kluyveromyces*, *Yarrowia* and *Pichia*. In some embodiments, the genetic modification increases activity of the mitogen-activated protein kinase module of the high osmolarity/glycerol response pathway. In some embodiments, the genetic modification increases PBS2 mitogen activated protein kinase kinase activity. In some embodiments, the modification increasing PBS2 mitogen activated protein kinase kinase activity is overexpression of a pBS2 protein encoding gene. In some embodiments, PBS2 protein encoding gene encodes a protein having an amino acid sequence with at least about 90% sequence identity to a sequence selected from the group consisting of SEQ ID NOs:50, 52, 54, 56, 58, 60, 62, 64, 66, 68, 70, 72, 74, 76, 78, and 80 based on Clustal W method of alignment using the default parameters of GAP PENALTY=10, GAP LENGTH PENALTY=0.1, and Gonnet 250 series of protein weight matrix. In some embodiments, increasing PBS2 mitogen activated protein kinase kinase activity is overexpression of a gene selected from the group consisting of SIN1, SHO1, MS81, OPY2, TOS2, MYO1, ABC1, YPT7, YPD1, SSK1, PKC1, CDC42, KIN1, SEC15, STE20, CDC37, CKB2, MAL31, RHO1, CAT5, STB3, RPD3, RSC4, SPT16 and HOR2.

Also provided are recombinant yeast cells comprising a butanol biosynthetic pathway and at least one heterologous PBS2 protein encoding gene. In some embodiments, the butanol biosynthetic pathway comprises at least one gene that is heterologous to the yeast cell. In some embodiments, the yeast cell has an increased tolerance to butanol as compared to a yeast cell that does not comprise at least one heterologous PBS2 protein encoding gene.

In some embodiments, the butanol biosynthetic pathway is selected from the group consisting of: a) a 1-butanol biosynthetic pathway; b) a 2-butanol biosynthetic pathway; and c) an isobutanol biosynthetic pathway. In some embodiments, the 1-butanol biosynthetic pathway comprises at least one gene encoding a polypeptide that performs at least one of the following substrate to product conversions: a) acetyl-CoA to acetoacetyl-CoA, as catalyzed by acetyl-CoA acetyltransferase; b) acetoacetyl-CoA to 3-hydroxybutyryl-CoA, as catalyzed by 3-hydroxybutyryl-CoA dehydrogenase; c) 3-hydroxybutyryl-CoA to crotonyl-CoA, as catalyzed by crotonase; d) crotonyl-CoA to butyryl-CoA, as catalyzed by butyryl-CoA dehydrogenase; e) butyryl-CoA to butyraldehyde, as catalyzed by butyraldehyde dehydrogenase; and f) butyraldehyde to 1-butanol, as catalyzed by 1-butanol dehydrogenase. In some embodiments, the 2-butanol biosynthetic pathway comprises at least one gene encoding a polypeptide that performs at least one of the following substrate to product conversions: a) pyruvate to alpha-acetolactate, as catalyzed by acetolactate synthase; b) alpha-acetolactate to acetoin, as catalyzed by acetolactate decarboxylase; c) acetoin to 2,3-butanediol, as catalyzed by butanediol dehydrogenase; d) 2,3-butanediol to 2-butanone, as catalyzed by butanediol dehydratase; and e) 2-butanone to 2-butanol, as catalyzed by 2-butanol dehydrogenase. In some embodiments, the isobutanol biosynthetic pathway comprises at least one gene encoding a polypeptide that performs at least one of the following substrate to product conversions: a) pyruvate to acetolactate, as catalyzed by acetolactate synthase; b) acetolactate to 2,3-dihydroxyisovalerate, as catalyzed by acetohydroxy acid isomeroreductase; c) 2,3-dihydroxyisovalerate to α-ketoisovalerate, as catalyzed by acetohydroxy acid dehydratase or dihydroxyacid dehydratase; d) α-ketoisovalerate to isobutyraldehyde, as catalyzed by a branched-chain keto acid decarboxylase; and e) isobutyraldehyde to isobutanol, as catalyzed by a branched-chain alcohol dehydrogenase.

Also provided herein are methods for the production of 1-butanol comprising growing recombinant yeast cells under conditions where 1-butanol is produced and optionally recovering the 1-butanol. Also provided herein are methods for the production of 2-butanol comprising growing recombinant yeast cells under conditions where 2-butanol is produced and optionally recovering the 2-butanol. Also provided are methods for the production of isobutanol comprising growing recombinant yeast cells under conditions where isobutanol is produced and optionally recovering the isobutanol.

Also provided herein are methods for producing a recombinant yeast cell having increased tolerance to butanol comprising: a) providing a recombinant yeast cell comprising a butanol biosynthetic pathway selected from the group consisting of: i) a 1-butanol biosynthetic pathway; ii) a 2-butanol biosynthetic pathway; and iii) an isobutanol biosynthetic pathway; and b) engineering the yeast cell of (a) to comprise at least one genetic modification which increases activity of the high osmolarity/glycerol response pathway wherein the genetic modification increases increases PBS2 mitogen activated protein kinase kinase activity.

Also provided herein is a method for improving fermentative production of butanol comprising:

a) providing a recombinant yeast cell comprising a butanol biosynthetic pathway selected from the group consisting of:
  i) a 1-butanol biosynthetic pathway
  ii) a 2-butanol biosynthetic pathway; and
  iii) an isobutanol biosynthetic pathway;
wherein said yeast cell also comprises at least one genetic modification that increases activity of the high osmolarity/glycerol response pathway and wherein the genetic modification increases PBS2 mitogen activated protein kinase activity; and b) contacting said yeast cell with fermentable sugar whereby said yeast cell produces butanol and wherein said yeast cell has improved tolerance to said butanol as compared to a yeast cell without at least one genetic modification that increases activity of the high osmolarity/glycerol response pathway and wherein the genetic modification increases PBS2 mitogen activated protein kinase activity. Said method also provides for improved production of butanol as compared to a yeast cell without at least one genetic modification that increases activity of the high osmolarity/glycerol response pathway and increases PBS2 mitogen activated protein kinase activity.

BRIEF DESCRIPTION OF THE DRAWINGS AND SEQUENCE DESCRIPTIONS

The various embodiments of the invention can be more fully understood from the following detailed description and the accompanying sequence descriptions, which form a part of this application.

Figure 1:
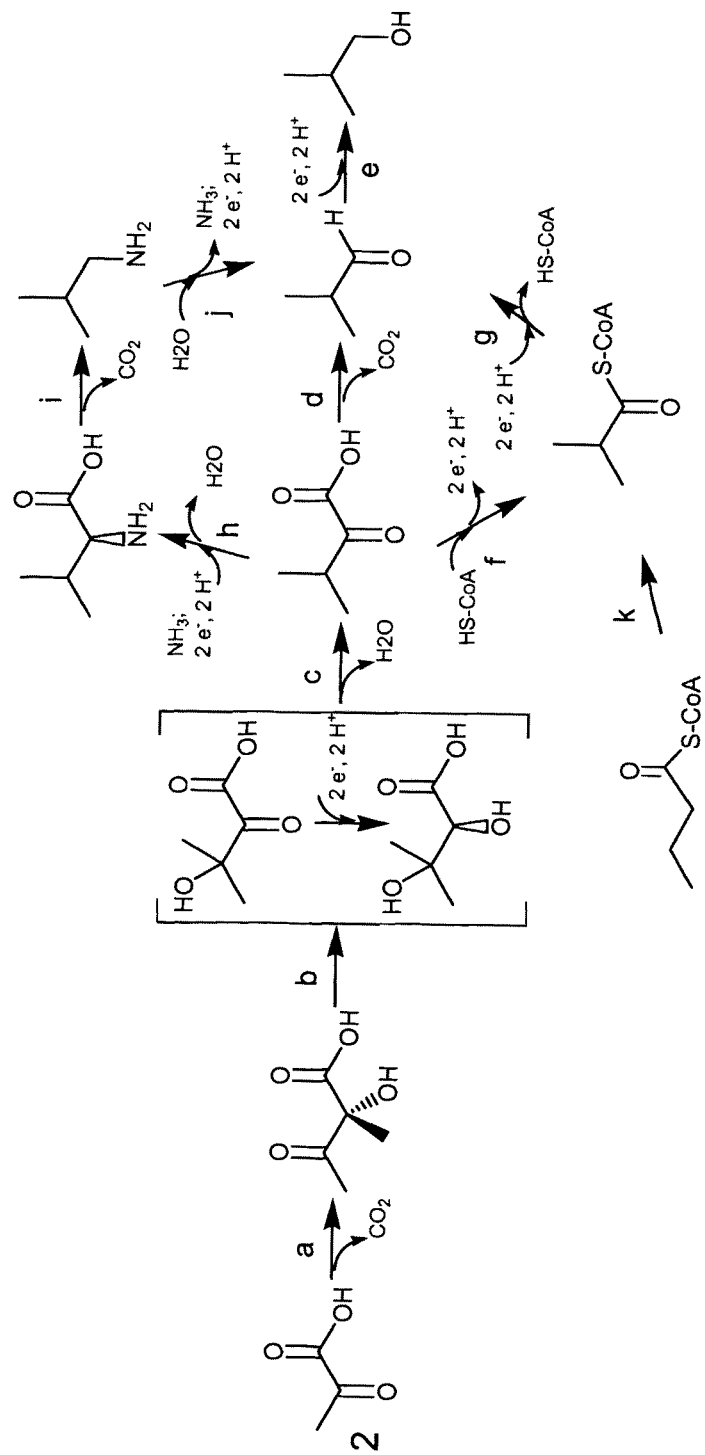
FIG. 1 depicts isobutanol biosynthetic pathways.
Figure 2:
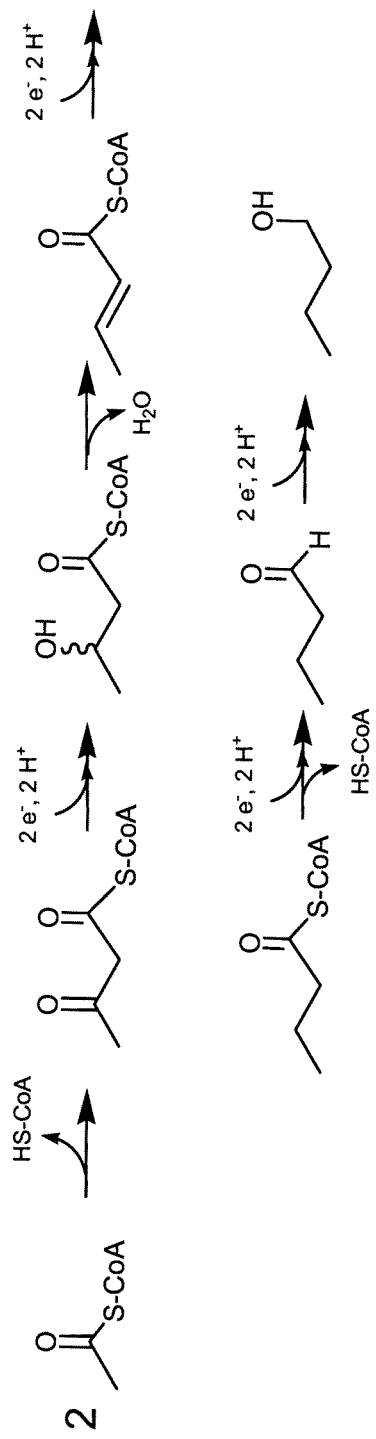
FIG. 2 depicts 1-butanol biosynthetic pathways.
Figure 3:
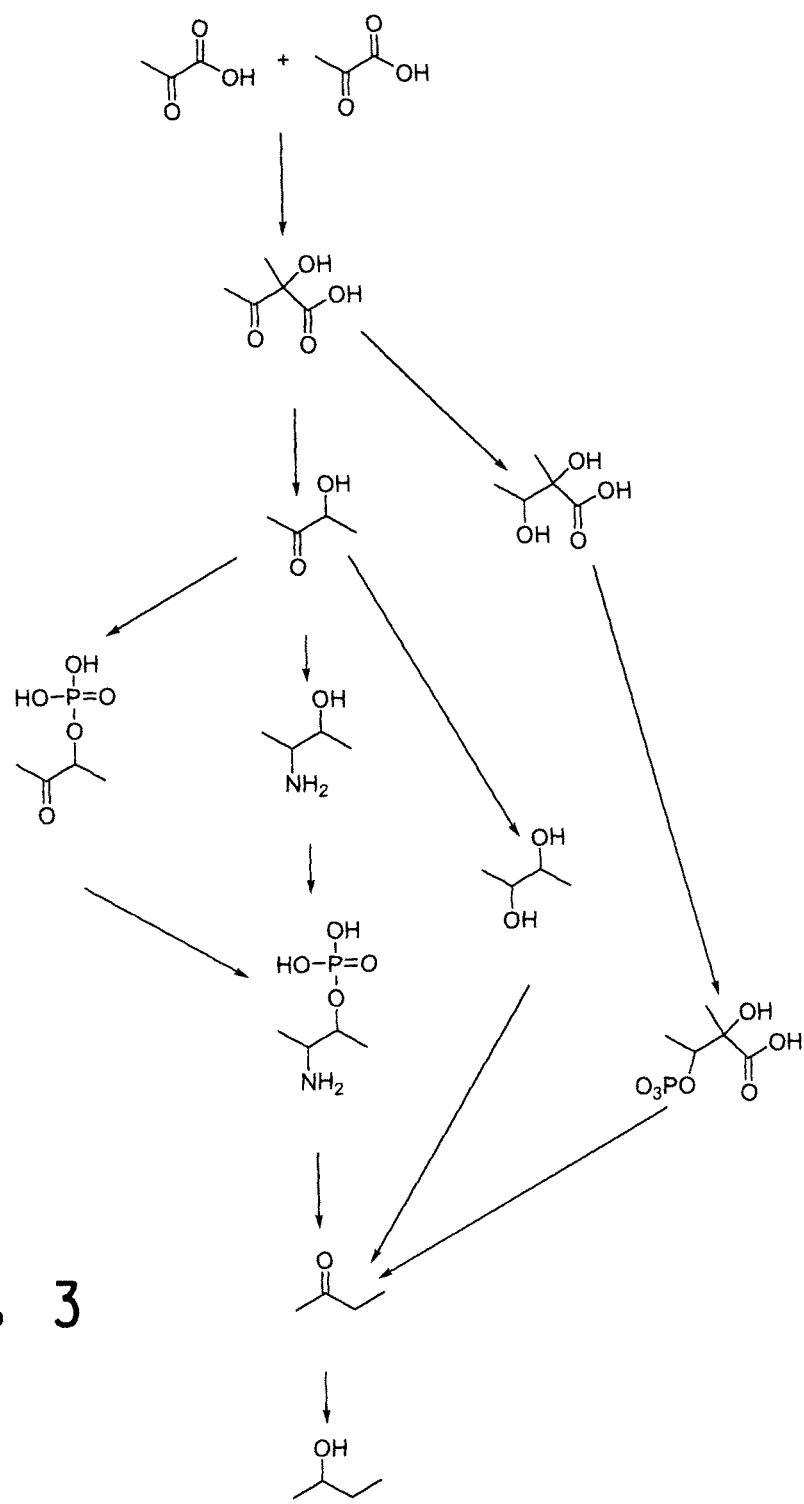
FIG. 3 depicts 2-butanol biosynthetic pathways.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Coding Region and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| Acetyl-CoA acetyltransferase from *Saccharomyces cerevisiae* | 39 | 40 |
| 3-Hydroxybutyryl-CoA dehydrogenase from *Clostridium acetobutylicum* ATCC 824 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum* ATCC 824 | 15 | 16 |

TABLE 2

Summary of Coding Region and Protein SEQ ID Numbers for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus ruber* 219 | 29 | 30 |

TABLE 3

Summary of Coding Region and Protein SEQ ID Numbers for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *Bacillus subtilis* alsS (acetolactate synthase) | 41 | 42 |
| *E. coli* ilvC (acetohydroxy acid reductoisomerase) | 31 | 32 |
| *S. cerevisiae* ILV5 (acetohydroxy acid reductoisomerase) | 43 | 44 |
| *B. subtilis* ilvC (acetohydroxy acid reductoisomerase) | 45 | 46 |
| *E. coli* ilvD (acetohydroxy acid dehydratase) | 33 | 34 |
| *S. cerevisiae* ILV3 (Dihydroxyacid dehydratase) | 47 | 48 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

TABLE 4

Summary of PBS2 Coding Region and Protein SEQ ID Numbers

| Organism | SEQ ID NO: Nucleic acid | SEQ ID NO: Peptide |
|---|---|---|
| Saccharomyces cerevisiae | 49 | 50 |
| Candida glabrata | 51 | 52 |
| Kluyveromyces lactis | 53 | 54 |
| Ashbya gossypii | 55 | 56 |
| Pichia stipitis | 57 | 58 |
| Candida albicans | 59 | 60 |
| Debaryomyces hansenii | 61 | 62 |
| Yarrowia lipolytica | 63 | 64 |
| Schizosaccharomyces pombe | 65 | 66 |
| Aspergillus terreus | 67 | 68 |
| Aspergillus fumigatus | 69 | 70 |
| Neurospora crassa | 71 | 72 |
| Aspergillus nidulans | 73 | 74 |
| Magnaporthe grisea | 75 | 76 |
| Cryptococcus neoformans | 77 | 78 |
| Ustilago maydis | 79 | 80 |

SEQ ID NOs:81 and 82 are primers used for sequencing the ends of the *S. cerevisiae* genomic DNA insert of the plasmids in yBUT2 and yBUT15 strains.

SEQ ID NOs:83 and 84 are primers for PCR of iYDR006C.

SEQ ID NOs:85 and 86 are primers for PCR of iYDR008C.

SEQ ID NOs:87 and 88 are primers for PCR of upTRP1 DR UR.

SEQ ID NOs:89 and 90 are primers for PCR of RA3* DR downTRP1.

SEQ ID NO:91 is the nucleotide sequence of the CUP1 promoter.

SEQ ID NO:92 is the nucleotide sequence of the CYC1 terminator.

SEQ ID NO:93 is the nucleotide sequence of the FBA promoter.

SEQ ID NO:94 is the nucleotide sequence of the ADH1 terminator.

SEQ ID NO:95 is the nucleotide sequence of the GPM promoter.

SEQ ID NOs:96 and 97 are primers for PCR of the PBS2 gene and flanking DNA.

DETAILED DESCRIPTION

The present invention relates to recombinant yeast cells that are engineered for production of butanol and that additionally are engineered to have increased activity of the high osmolarity/glycerol response pathway. The present yeast cells may have increased expression or activity of at least one protein involved in promoting activity of the high osmolarity/glycerol response pathway including proteins that are pathway receptors of external stimuli, proteins that are in the mitogen-activated protein kinase (MAPK) module of this pathway, and proteins that are downstream targets of the MAPK module of this pathway. These yeast cells have increased tolerance to butanol and may be used for production of butanol which is valuable as a fuel or fuel additive to reduce demand for fossil fuels.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value The term "butanol" as used herein, refers to 1-butanol, 2-butanol, isobutanol, or mixtures thereof.

The terms "butanol tolerant yeast cell" and "tolerant" when used to describe a modified yeast cell of the invention, refers to a modified yeast that shows better growth in the presence of butanol than the parent strain from which it is derived.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "mitogen activated protein (MAP) kinase" refers to proteins with EC number EC 2.7.11.24, which are serine/threonine-specific protein kinases that respond to extracellular stimuli (mitogens) and regulate various cellular activities, such as gene expression, mitosis, differentiation, and cell survival/apoptosis.

The term "PBS2" refers to a gene encoding a type of MAP kinase kinase that is a part of the mitogen-activated protein kinase module of the high osmolarity/glycerol response pathway. PBS2p is the protein encoded by PBS2, which is an example of proteins classified as EC 2.7.12.2. Proteins with the same function as PBS2p encoded by PBS2 may be referred to in the art as being encoded by genes with other names including SPC2, WIS1, SMF2, dSOR1, HOG4, SFS4, and SSK4. The term PBS2p refers herein to any of these encoded proteins that function similarly to PBS2p in the mitogen-activated protein kinase module of the high osmolarity/glycerol response pathway and that have sequence identity to a PBS2p amino acid sequence that is at least about 55%-60%, 60%-65%, 65%-70%, 70%-75%, 75%-80%, 80%-85%, 85%-90%, 90%-95%, or 95%-100%.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [*Enzyme Nomenclature* 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148 (SEQ ID NO:39)).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZAADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (Gen Bank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence (SEQ ID NO:42), L04470 NCBI nucleotide sequence (SEQ ID NO:41)), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459 (SEQ ID NO:44), NC_001144 (SEQ ID NO:43)), *Methanococcus maripaludis* (GenBank Nos: CAF30210, BX957220), and *Bacillus subtilis* (GenBank Nos: CAB14789 (SEQ ID NO:46), Z99118 (SEQ ID NO:45)).

The term "acetohydroxy acid dehydratase" or "dihydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550 (SEQ ID NO:48), NC_001142 (SEQ ID NO:47)), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), and *C. acetobutylicum* (GenBank Nos: NP_349892, NC_003030).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "heterologous" or "foreign" gene refers to a gene not normally found in the host organism, but that is introduced into the host organism by gene transfer. Foreign or heterologous genes can comprise native genes inserted into a non-native organism, or chimeric genes. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

As used herein, "substantially similar" enzymes will refer to enzymes belonging to a family of proteins in the art known to share similar structures and function. It is well within the skill of one in the art to identify substantially similar proteins given a known structure. Typical methods to identify substantially similar structures will rely upon known sequence information (nucleotide sequence and/or amino acid sequences) and may include PCR amplification, nucleic acid hybridization, and/or sequence identity/similarity analysis (e.g., sequence alignments between partial and/or complete sequences and/or known functional motifs associated with the desired activity).

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Given the nucleic acid sequences described herein, one of skill in the art can identify substantially similar nucleic acid fragments that may encode proteins having similar activity. Hybridization and washing conditions are well known and exemplified in Sambrook, J., Fritsch, E. F. and Maniatis, T. *Molecular Cloning: A Laboratory Manual*, 3rd ed., Cold Spring Harbor Laboratory: Cold Spring Harbor, N.Y. (2001), particularly Chapter 11 and Table 11.1 therein.

The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS at 65° C. followed by 0.1×SSC, 0.1% SDS at 65° C., for example.

In one aspect, suitable nucleic acid fragments encode polypeptides that are at least about 70% identical to the amino acid sequences reported herein. In another aspect, the nucleic acid fragments encode amino acid sequences that are about 85-90% identical to the amino acid sequences reported herein. In a further aspect, the nucleic acid fragments encode amino acid sequences that are at least about 90-100% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: N.J. (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: N.Y. (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*. 5:151-153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "homology" refers to the relationship among sequences whereby there is some extent of likeness, typically due to descent from a common ancestral sequence. Homologous sequences can share homology based on genic, structural, functional and/or behavioral properties. The term "ortholog" or "orthologous sequences" refers herein to a relationship where sequence divergence follows speciation (i.e., homologous sequences in different species arose from a common ancestral gene during speciation). In contrast, the term "paralogous" refers to homologous sequences within a single species that arose by gene duplication. One skilled in the art will be familiar with techniques required to identify homologous, orthologous and paralogous sequences.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein, "default values" will mean any set of values or parameters (as set by the software manufacturer) which originally load with the software when first initialized Standard recombinant DNA and molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

"Fermentable sugars" refers to a sugar content primarily comprising monosaccharides and some disaccharides that can be used as the carbon source by microorganisms in a fermentation process to produce a target product. Sugars may from from any source, including cellulosic, hemicellulosic or ligcellulosic biomass.

Screening for Butanol Tolerance: Involvement of High Osmolarity/Glycerol Response Pathway The invention relates to the discovery that increasing activity of the high osmolarity/glycerol response pathway has the effect of increasing tolerance of yeast cells to butanol. The discovery came from screening studies to identify yeast cells containing random fragments of yeast genomic DNA that had increased tolerance to butanol. In these studies, yeast containing a library of random genomic DNA fragments were grown in the presence of isobutanol to identify clones with improved growth relative to controls. In one clone with increased tolerance to butanol the random genomic DNA fragment was found to include the PBS2 gene. In further experiments herein, overexpression of the PBS2 coding region was found to increase tolerance of yeast to butanol. A yeast strain which overexpressed the PBS2p product of the PBS2 coding region had at least about a 40%, specifically a 41%, improvement in growth yield over the parental strain in 1% (w/v) isobutanol (Example 2 herein). In accordance with the present invention, yeast strains comprising a heterologous PBS2 protein encoding gene may have at least about a 20% increase in growth yield, at least about a 30% increase in growth yield, or at least a 40% increase in growth yield over the parental strain.

The PBS2p product of the PBS2 gene plays an important role in the high osmolarity/glycerol (HOG) response pathway. PBS2p is a mitogen activated protein kinase (MAPK) kinase which is part of a MAPK module in yeast that responds to high external osmolarity. Thus increase in PBS2p expression increases activity of the HOG response pathway.

Increase in High Osmolarity/Glycerol Response Pathway Activity by Directly Engineering PBS2p Expression In the present engineered yeast cell any PBS2p may be expressed in increased amount above the amount found in the cell without PBS2p engineering to provide increased butanol tolerance. In the present yeast cell the endogenous PBS2p of the target yeast cell may be overexpressed, or a heterologous PBS2p may be expressed in the cell to provide increased activity. Examples of PBS2p that may be expressed include those from *Saccharomyces cerevisiae* (coding region SEQ ID NO:49; protein SEQ ID NO:50), *Candida glabrata* (coding region SEQ ID NO:51; protein SEQ ID NO:52), *Kluyveromyces lactis* (coding region SEQ ID NO:53; protein SEQ ID NO:54), *Ashbya gossypii* (coding region SEQ ID NO:55; protein SEQ ID NO:56), *Pichia stipitis* (coding region SEQ ID NO:57; protein SEQ ID NO:58), *Candida albicans* (coding region SEQ ID NO:59; protein SEQ ID NO:60), *Debaryomyces hansenii* (coding region SEQ ID NO:61; protein SEQ ID NO:62), *Yarrowia lipolytica* (coding region SEQ ID NO:63; protein SEQ ID NO:64), *Schizosaccharomyces pombe* (coding region SEQ ID NO:65; protein SEQ ID NO:66), *Aspergillus terreus* (coding region SEQ ID NO:67; protein SEQ ID NO:68), *Aspergillus fumigatus* (coding region SEQ ID NO:69; protein SEQ ID NO:70), *Neurospora crassa* (coding region SEQ ID NO:71; protein SEQ ID NO:72), *Aspergillus nidulans* (coding region SEQ ID NO:73; protein SEQ ID NO:74), *Magnaportha grisea* (coding region SEQ ID NO:75; protein SEQ ID NO:76), *Cryptococcus neopormans* (coding region SEQ ID NO:77; protein SEQ ID NO:78), and *Ustilago maydis* (coding region SEQ ID NO:79; protein SEQ ID NO:80).

Some proteins that can be recognized as performing the same function as PBS2p, that have high sequence identity to PBS2p, may have a different name in the art. Other names for the PB2 gene include SPC2, WIS1, SMF2, dSOR1, HOG4, SFS4, and SSK4. Though there is this variation in naming, a protein may be readily recognized as a PBS2p homolog by its sequence and by its activity as a MAP kinase kinase in the MAP kinase module of the HOG response pathway.

Because the sequences of PBS2 coding regions and the encoded proteins are known, as exemplified in the SEQ ID NOs listed above and given in Table 4, suitable PBS2ps may be readily identified by one skilled in the art on the basis of sequence similarity using bioinformatics approaches. Typically BLAST (described above) searching of publicly available databases with known PBS2p amino acid sequences, such as those provided herein, is used to identify PBS2ps, and their encoding sequences, that may be used in the present strains. These proteins may have at least about 55%-60%, 60%-65%, 65%-70%, 70%-75%, 75%-80%, 80-85%, 85%-90%, 90%-95% or 95%-99% sequence identity to any of the PBS2ps of SEQ ID NOS:50, 52, 54, 56, 58, 60, 62, 64, 66, 68, 70, 72, 74, 76, 78, or 80 while having PBS2p activity. Identities are based on the Clustal W method of alignment using the default parameters of GAP PENALTY=10, GAP LENGTH PENALTY=0.1, and Gonnet 250 series of protein weight matrix.

In addition to using protein or coding region sequence and bioinformatics methods to identify additional PBS2ps, the sequences described herein or those recited in the art may be used to experimentally identify other homologs in nature. For example each of the PBS2 encoding nucleic acid fragments described herein may be used to isolate genes encoding homologous proteins. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the PBS2p encoding genes described herein could be isolated directly by using all or a portion of the instant nucleic acid fragments as DNA hybridization probes to screen libraries from any desired organism using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments by hybridization under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, V A; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described PBS2p encoding sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Expression of PBS2p is achieved by transforming with a gene comprising a sequence encoding a PBS2p. When using a heterologous coding region, the sequence may be codon-optimized for maximal expression in the target yeast host cell, as well known to one skilled in the art. Methods for gene expression in yeasts are known in the art (see for example *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Expression of genes in yeast typically requires a promoter, operably linked to a coding region of interest, and a transcriptional terminator. A number of yeast promoters can be used in constructing expression cassettes for genes encoding a PBS2p, including, but not limited to constitutive promoters FBA, GPD, ADH1, TEF, and GPM, and the inducible promoters GAL1, GAL10, and CUP1. Suitable transcriptional terminators include, but are not limited to FBAt, GPDt, GPMt, ERG10t, GAL1t, CYC1, and ADH1.

Suitable promoters, transcriptional terminators, and PBS2 coding regions may be cloned into *E. coli*-yeast shuttle vectors, and transformed into yeast cells. These vectors allow propagation in both *E. coli* and yeast strains. Typically the vector contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2µ origin of replication, and a marker for nutritional selection. The selection markers for these four vectors are His3 (vector pRS423), Trp1 (vector pRS424), Leu2 (vector pRS425) and Ura3 (vector pRS426). Construction of expression vectors with a chimeric gene encoding an PBS2p may be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a $\geq$21 bp sequence at both the 5' and the 3' ends that sequentially overlap with each other, and with the 5' and 3' terminus of the vector DNA. For example, to construct a yeast expression vector for "Gene X", a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g. TOP10, followed by mini preps and restriction mapping to further verify the plasmid construct. Finally the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding regionX-terminator construct is PCR amplified from a plasmid DNA construct and joined to an autotrophic marker (such as URA3) by either SOE PCR or by common restriction digests and cloning. The full cassette, containing the promoter-coding regionX-terminator-URA3 region, is PCR amplified with primer sequences that contain 40-70 bp of homology to the regions 5' and 3' of location "Y" on the yeast chromosome. The PCR product is transformed into yeast and selected on growth media lacking uracil. Transformants can be verified either by colony PCR or by direct sequencing of chromosomal DNA. In addition the endogenous promoter of a gene may be replaced with a stronger promoter to increase expression by homologous recombination.

Additional Engineering to Increase High Osmolarity/Glycerol Response Pathway Activity Increased expression of other genes of the HOG response pathway may be engineered to provide yeast cells of the present invention that have increased tolerance to butanol. Target genes and their encoded proteins for increased expression in the present yeast cells include any gene whose increased expression causes increased activity of the HOG response pathway. Target genes may include those that increase activity of PBS2p as well as any gene whose activity is increased by increased PBS2p activity. Genes of the HOG response pathway are known in the art and are disclosed in Hohmann et al. ((2007) Methods in Enzymology, Academic Press. 428:29-45) and Chen and Thorner (2007) Biochimica et Biophysica Acta 1773:1311-1340). For example, genes that may be targets are in the MAPK module of the HOG response pathway, including the MAP kinase HOG1, PBS2, and the MAPKK kinases (MAPKKK) STE11, SSK2, and SSK22. Additional genes that may be targets are genes that affect the MAPK module of the HOG response pathway including SIN1, SHO1, MSB1, OPY2, TOS2, MYO1, ABC1, YPT7, YPD1, SSK1, PKC1, CDC42, KIN1, SEC15, STE20, CDC37, CKB2, MAL31 and RHO1. Target genes for increased HOG response pathway activity that are downstream of the MAPK module include transcription factors and metabolism genes such as CAT5, STB3, RPD3, RSC4, SPT16 and HOR2

The activity of any of the proteins encoded by these target genes may be increased by overexpressing the endogenous encoding sequence in a yeast cell or by expressing a heterologous sequence encoding the protein. Expression of any of these proteins may be accomplished as described above for PBS2p. The coding sequences and encoded proteins that may be used in the present cells may be readily identified in publicly available databases by one skilled in the art using the gene names and functions listed above. Any coding region to be expressed may be codon optimized for the host cell to be engineered, as well known to one skilled in the art.

Host Yeast Cells

The target genes and proteins that are engineered to provide an increase in HOG response pathway activity to confer butanol tolerance may be engineered in any yeast cell that is additionally engineered for production of butanol. Suitable yeasts include, but are not limited to, *Saccharomyces, Schizosaccharomyces, Hansenula, Candida, Kluyveromyces, Yarrowia, Issatchenkia,* and *Pichia.* Suitable strains include, but are not limited to, *Saccharomyces cerevisiae Schizosaccharomyces pombe, Kluyveromyces lactis, Kluyveromyces thermotolerans, Candida glabrata, Candida albicans, Pichia stipitis* and *Yarrowia lipolytica.*

Butanol Biosynthetic Pathway

In the present invention, a genetic modification conferring increased butanol tolerance, as described above, is engineered in a yeast cell that is engineered to express a butanol biosynthetic pathway. Either genetic modification may take place prior to the other. The butanol biosynthetic pathway may be a 1-butanol, 2-butanol, or isobutanol biosynthetic pathway.

Suitable biosynthetic pathways are known in the art, and certain suitable pathways are described herein. In some embodiments, the butanol biosynthetic pathway comprises at least one gene that is heterologous to the yeast cell. In some embodiments, genes encoding proteins which catalyze each substrate to product conversion of the butanol biosynthetic pathway are heterologous to the yeast cell. In some embodiments, the butanol biosynthetic pathway comprises more than one gene that is heterologous to the yeast cell. In some embodiments, genes encoding proteins which catalyze each substrate to product conversion of the butanol biosynthetic pathway are heterologous to the yeast cell. In some embodiments, the yeast cell comprises heterologous genes encoding the proteins for each substrate to product conversion of a butanol biosynthetic pathway.

Likewise, certain suitable proteins having the ability to catalyze the indicated substrate to product conversions are described herein and other suitable proteins are described in the art. For example, US Published Patent Application Nos. US20080261230 and US20090163376, incorporated herein by reference, describe acetohydroxy acid isomeroreductases; U.S. patent application Ser. No. 12/569,636, incorporated by reference, describes suitable dihydroxyacid dehydratases; a suitable alcohol dehydrogenase is described in US Published Patent Application US20090269823, incorporated herein by reference.

1-Butanol Biosynthetic Pathway

A suitable biosynthetic pathway for the production of 1-butanol that may be used is described by Donaldson et al. in U.S. Patent Application Publication No. US20080182308A1, incorporated herein by reference. This biosynthetic pathway comprises the following substrate to product conversions:
a) acetyl-CoA to acetoacetyl-CoA, as catalyzed for example by acetyl-CoA acetyltransferase with protein sequence such as SEQ ID NO:2, 4 or 40 (which may be encoded, for example, by the genes given as SEQ ID NO:1, 3 or 39);
b) acetoacetyl-CoA to 3-hydroxybutyryl-CoA, as catalyzed for example by 3-hydroxybutyryl-CoA dehydrogenase with protein sequence such as SEQ ID NO:6 (which may be encoded, for example, by the gene given as SEQ ID NO:5);
c) 3-hydroxybutyryl-CoA to crotonyl-CoA, as catalyzed for example by crotonase with protein sequence such as SEQ ID NO:8 (which may be encoded, for example, by the gene given as SEQ ID NO:7);
d) crotonyl-CoA to butyryl-CoA, as catalyzed for example by butyryl-CoA dehydrogenase with protein sequence such as SEQ ID NO:10 (which may be encoded, for example, by the gene given as SEQ ID NO:9);
e) butyryl-CoA to butyraldehyde, as catalyzed for example by butyraldehyde dehydrogenase with protein sequence such as SEQ ID NO:12 (which may be encoded, for example, by the gene given as SEQ ID NO:11); and
f) butyraldehyde to 1-butanol, as catalyzed for example by 1-butanol dehydrogenase with protein sequence such as SEQ ID NO:14 or 16 (which may be encoded, for example, by the genes given as SEQ ID NO:13 or 15).

The pathway requires no ATP and generates $NAD^+$ and/or $NADP^+$, thus, it balances with the central, metabolic routes that generate acetyl-CoA.

Other suitable biosynthetic pathways for the production of 1-butanol will be apparent to those of skill in the art. It will be appreciated that yeast cells may be engineered to express proteins that retain the ability to catalyze the indicated substrate to product conversion but have less than 100% sequence identity to the protein sequences provided herein. In one embodiment, yeast cells may be engineered to express a 1-butanol biosynthetic pathway comprising a sequence that has at least about 70%-75%, 75%-80%, 80-85%, 85%-90%, 90%-95% or 95%-99% sequence identity to a 1-butanol pathway protein provided herein.

2-Butanol Biosynthetic Pathway

Suitable biosynthetic pathways for the production of 2-butanol that may be used are described by Donaldson et al. in U.S. Patent Application Publication Nos. US20070259410A1 and US 20070292927A1, each incorporated herein by reference. One 2-butanol biosynthetic pathway comprises the following substrate to product conversions:
a) pyruvate to alpha-acetolactate, as catalyzed for example by acetolactate synthase with protein sequence such as SEQ ID NO:20 (which may be encoded, for example, by the gene given as SEQ ID NO:19);
b) alpha-acetolactate to acetoin, as catalyzed for example by acetolactate decarboxylase with protein sequence such as SEQ ID NO:18 (which may be encoded, for example, by the gene given as SEQ ID NO:17);
c) acetoin to 2,3-butanediol, as catalyzed for example by butanediol dehydrogenase with protein sequence such as SEQ ID NO:22 (which may be encoded, for example, by the gene given as SEQ ID NO:21);
d) 2,3-butanediol to 2-butanone, catalyzed for example by butanediol dehydratase with protein sequence such as SEQ ID NO:24, 26, or 28 (which may be encoded, for example, by genes given as SEQ ID NO:23, 25, or 27); and
e) 2-butanone to 2-butanol, as catalyzed for example by 2-butanol dehydrogenase with protein sequence such as SEQ ID NO:30 (which may be encoded, for example, by the gene given as SEQ ID NO:29).

Other suitable biosynthetic pathways for the production of 2-butanol will be apparent to those of skill in the art. It will be appreciated that yeast cells may be engineered to express proteins that retain the ability to catalyze the indicated substrate to product conversion but have less than 100% sequence identity to the protein sequences provided herein. In one embodiment, yeast cells may be engineered to express a 2-butanol biosynthetic pathway comprising a sequence that has at least about 70%-75%, 75%-80%, 80-85%, 85%-90%, 90%-95% or 95%-99% sequence identity to a 2-butanol pathway protein provided herein.

Isobutanol Biosynthetic Pathway

Suitable biosynthetic pathways for the production of isobutanol that may be used are described by Maggio-Hall et al. in U.S. Patent Application Publication No. US20070092957 A1, incorporated herein by reference. One isobutanol biosynthetic pathway comprises the following substrate to product conversions:
a) pyruvate to acetolactate, as catalyzed for example by acetolactate synthase with protein sequence such as SEQ ID NO:20 or 42 (which may be encoded, for example, by genes given as SEQ ID NO:19 or 41);
b) acetolactate to 2,3-dihydroxyisovalerate, as catalyzed for example by acetohydroxy acid isomeroreductase with protein sequence such as SEQ ID NO:32, 44 or 46 (which may be encoded, for example, by genes given as SEQ ID NO:31, 43 or 45);
c) 2,3-dihydroxyisovalerate to α-ketoisovalerate, as catalyzed for example by acetohydroxy acid dehydratase with protein sequence such as SEQ ID NO:34 (which may be encoded, for example, by the gene given as SEQ ID NO:33); or dihydroxyacid dehydratase with protein sequence such as SEQ ID NO:48 (which may be encoded, for example, by the gene given as SEQ ID NO:47);
d) α-ketoisovalerate to isobutyraldehyde, as catalyzed for example by a branched-chain keto acid decarboxylase with protein sequence such as SEQ ID NO:36 (which may be encoded, for example, by the gene given as SEQ ID NO:35); and
e) isobutyraldehyde to isobutanol, as catalyzed for example by a branched-chain alcohol dehydrogenase with protein sequence such as SEQ ID NO:38 (which may be encoded, for example, by the gene given as SEQ ID NO:37).

Other suitable biosynthetic pathways for the production of isobutanol will be apparent to those of skill in the art. It will be appreciated that yeast cells may be engineered to express proteins that retain the ability to catalyze the indicated substrate to product conversion but have less than 100% sequence identity to the protein sequences provided herein. In one embodiment, yeast cells may be engineered to express an isobutanol biosynthetic pathway comprising a sequence that has at least about 70%-75%, 75%-80%, 80-85%, 85%-90%, 90%-95% or 95%-99% sequence identity to an isobutanol pathway protein provided herein.

Construction of Yeast Strains for Butanol Production

Any yeast strain that is genetically modified for butanol tolerance as described herein is additionally genetically modified (before or after modification to tolerance) to incorporate a butanol biosynthetic pathway by methods well known to one skilled in the art. Genes encoding the enzyme activities described above, or homologs that may be identified and obtained by commonly used methods, such as those described above, that are well known to one skilled in the art, are introduced into a yeast host. Representative coding and amino acid sequences for pathway enzymes that may be used are given in Tables 1, 2, and 3, with SEQ ID NOs:1-48. Methods for gene expression in yeasts that may be used for butanol pathway genes are described above for expression of PBS2.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production.

Culture Conditions

Typically cells are grown at a temperature in the range of about 20° C. to about 37° C. in an appropriate medium. Suitable growth media in the present invention are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5.0 to pH 6.5 is preferred as the initial condition.

Fermentations may be performed under aerobic or anaerobic conditions, where anaerobic or microaerobic conditions are preferred.

The amount of butanol produced in the fermentation medium can be determined using a number of methods known in the art, for example, high performance liquid chromatography (HPLC) or gas chromatography (GC).

Industrial Batch and Continuous Fermentations

The present process may employ a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as CO2. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1-butanol production.

Methods for Butanol Isolation from the Fermentation Medium

The bioproduced butanol may be isolated from the fermentation medium using methods known in the art. For example, solids may be removed from the fermentation medium by centrifugation, filtration, decantation, or the like. Then, the butanol may be isolated from the fermentation medium, which has been treated to remove solids as described above, using methods such as distillation, liquid-liquid extraction, or membrane-based separation. Because butanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see for example Doherty and Malone, *Conceptual Design of Distillation Systems*, McGraw Hill, New York, 2001).

The butanol-water mixture forms a heterogeneous azeotrope so that distillation may be used in combination with decantation to isolate and purify the butanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

The butanol may also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent. Distillation in combination with adsorption may also be used to isolate butanol from the fermentation medium. In this method, the fermentation broth containing the butanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial and yeast cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989) or in *Yeast Protocols, Second Edition* (Wei Xiao, ed; Humana Press, Totowa, N.J. (2006))). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

Methods for Determining Isobutanol Concentration in Culture Media

The concentration of isobutanol in the culture media can be determined by a number of methods known in the art. For example, a specific high performance liquid chromatography (HPLC) method utilizes a Shodex SH-1011 column with a Shodex SH-G guard column, both purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions described. Alternatively, gas chromatography (GC) methods are available. For example, a specific GC method utilizes an HP-INNOWax column (30 m×0.53 mm id, 1 μm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature ias 45° C. for 1 min, 45 to 220° C. at 10° C./min, and 22° C. for 5 min; and FID detection is employed at 240° C. with 26 mL/min helium makeup gas. The retention time of isobutanol is 4.5 min.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "μM" means micromolar, "M" means molar, "mmol" means millimole(s), "μmol" means micromole(s)", "g" means gram(s), "μg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "HPLC" means high performance liquid chromatography, and "GC" means gas chromatography.

CM refers to synthetic complete medium which is described in Amberg, Burke and Strathern, 2005, Methods in Yeast Genetics, Cold Spring Harbor Laboratory Press, Cold Spring Harbor, N.Y.

Example 1

Identification of PBS2 from an Isobutanol Tolerance Screen

A yeast genomic library in the *E. coli*/yeast shuttle vector YEp13 was obtained from the American Type Culture Collection (ATCC 37323; Reed et al. (1989) J. Cell Sci. Suppl. 12:29-37). The library was provided in an *E. coli* host and supplies complete coverage of the *Saccharomyces cerevisiae* genome with 10,000 clones containing random and/or overlapping fragments of genomic DNA. The YEp13 vector includes a selectable yeast LEU marker and an *E. coli* marker, bla, specifying ampicillin resistance. The library was amplified by growth of the *E. coli* mixed culture in LB with ampicillin (50 µg/ml) for 16 hours at 37° C. with shaking, isolated from *E. coli* using a Qiaprep Spin Miniprep Kit (Cat. No. 27104) and transformed into *S. cerevisiae* BY4741 cells (ATCC 201388) using a lithium acetate transformation procedure (Gietz et al. (1995) *Yeast* 11:355-360). Transformants were washed from selection plates (SD Agar minus leucine, called CSM-Leu; Cat #YPL-1540 of KD Medical; Columbia, Md.) and combined to form a pool of at least 10,000 *S. cerevisiae* BY4741 transformants. The pool was mixed with 25% glycerol and stored at −70° C.

Isolation of Isobutanol Tolerance Clones by Screening

The pool was plated on selective media (CM-Leu) and colonies grown at 30° C. were picked to liquid selective medium in microtiter wells and then grown for 2 days at 30° C. with shaking. Glycerol was added to a final concentration of 12% (v/v) and mixed by repeated pipetting prior to freezing at −80° C. Microtiter contents were thawed prior to printing to control and isobutanol containing agar plates (CM-Leu). Leu+ transformants of BY4741 (haploid) were obtained and picked to microtiter wells. Growth of more than 10,000 clones was compared on control plates (complete synthetic medium lacking leucine) and on the same plates containing 1.8% (w/v) isobutanol after 2 days at 30° C. This primary screen identified 638 putative isobutanol tolerant colonies. Positive-scoring colonies were consolidated by inoculating new microtiter plates containing CM-Leu liquid media that were incubated at 30° C. overnight. A secondary screen for isobutanol tolerant clones was accomplished by printing from the consolidated microtiter plates on 1.6%, 1.8% and 2% (w/v) isobutanol containing agar plates and observing growth. This secondary screen identified 14 tolerant clones with improved growth relative to controls, termed BUT (isoBUtanol Tolerant) clones.

Molecular Identity of the BUT Clones

The fragments of genomic DNA present in two of the 14 isobutanol tolerant strains named yBUT2 and yBUT15 were characterized as follows. DNA was prepared from 2 µl of well mixed frozen cell glycerol stock (20% final) that was mixed with 9 µl of Genomiphi Sample Buffer prior to the addition of 1 µl zymolase [5units] (ZymoResearch, Cat#E1004). Samples were incubated for 15 minutes at 37° C. The reaction was terminated by heating for 3 minutes at 95° C. (no longer). The heated sample was cooled at 4° C. for 5 minutes.

To amplify DNA we used the GE/Amersham Biosciences Illustra™ GenomiPhi V2 DNA Amplification Kit (Product number: 25-6600-31) which was stored at −70° C. The kit was not allowed to warm above 4° C. prior to initiation of DNA amplification. Next amplification reactions were set up. A reaction mix was prepared by combining 19.5 µl Reaction Buffer+0.5 µl Enzyme Mix (Genomiphi Version 2). 10 µl of the Reaction Mix was added to the heated and cooled template sample described in the prior paragraph. Amplification reactions were incubated at 30° C. overnight. Amplification reactions were terminated by heating at 65° C. for 10 minutes prior to cooling on ice. This amplified, derivative genomic DNA sample, including the YEp13 clone, was suitable for sequencing without any further manipulation.

DNA sequencing was performed as follows. For each 20 µl Genomiphi amplified sample, 8 µl was removed and added to 8 µl of Big Dye v3.1 Sequencing reagent (PN #4337457 Applied Biosystems, Foster City, Calif., 94404 USA), 4 µl of 10 µM primer (ype13-fwd: 5'-CTATGCGCACCCGT-TCTCGGAGC SEQ ID NO:81, or ype13-rev: 5'-CGCTCAT-GAGCCCGAAGTGGCG SEQ ID NO:82; Sigma Genosys, Woodlands, Tex.), 4 µl 5× Sequencing buffer (PN #4336699 Applied Biosystems, Foster City, Calif.) and 16 µl Molecular Biology Grade water (Mediatech, Inc., Herndon, Va.). The sequencing reactions were then thermal cycled as follows; 3 minutes at 96° C. followed by 200 cycles of (95° C. 30 sec+55° C. 20 sec+60° C. 2 min) then stored at 4° C. The unincorporated ddNTPs were removed prior to sequencing using Edge Biosystems (Gaithersburg, Md.) clean-up plates. For each sequencing reaction the total 40 µl was pipetted into one well of a pre-spun 96 well clean up plate. The plate was then spun for 5 min at 5,000×g in a Sorvall RT-7 refrigerated centrifuge. The cleaned up reactions were then placed directly onto an Applied Biosystems 3730 DNA sequencer and sequenced with automatic base-calling.

The sequences of the two DNA vector-insert junction fragments from each clone were aligned to the yeast genome (*Saccharomyces* Genome Database) via the BLAST method (Altschul et al. (1997) Nucleic Acids Research 25:3389-3402). Both insert ends of yBUT2 were homologous to segments of chromosome X. One sequence read matched 92 of 92 nucleotides between nucleotide positions 176066 and 176320 on chromosome X while the other junction matched 445 of 469 nucleotides between nucleotide positions 181768 and 182236. These data demonstrated that a 6170 bp fragment resides on the plasmid of yBUT2 that contains nucleotides 176066 to 182236 of chromosome X. This region contains the following ORFS and genetic elements:

TRK1' PBS2 YJL127W-A YJL127C-B where TRK1' indicates a 3' truncation.

YJL127W-A is annotated as a dubious open reading frame unlikely to encode a protein and YJL127C-B is annotated as encoding a putative protein of unknown function. The other complete ORF was PBS2 which encodes a cell wall integrity specific MAP Kinase Kinase. This MAP Kinase Kinase is part of a regulatory cascade that controls the cellular osmolarity response (Chen and Thorner (2007) Biochimica. et Biophysica. Acta 1773:1311-1340).

Both insert ends of yBUT15 were homologous to segments of chromosome X. One sequence read matched 622 of 661 nucleotides between nucleotide positions 176260 and 176918 on chromosome X while the other junction matched 609 of 615 nucleotides between nucleotide positions 181422 and 182036. These data demonstrated that a 5776 bp fragment resides on the plasmid of yBUT2 that contains nucleotides 176260 to 182036 of chromosome X. This region contains the same ORFs and genetic elements as yBUT2 though the fragment ends differ:

TRK1' PBS2 YJL127W-A YJL127C-B where TRK1' indicates a 3' truncation

Example 2

Overexpression of PBS2 Coding Region

The effect of overexpression of the PBS2 coding region was assessed as follows. A Yeast ORF collection (Gelperin, White et al. (2005) Genes Dev. 19(23):2816-2826)_is available from Open Biosystems (Huntsville, Ala.). In this collection yeast ORFs are expressed from the GAL1 promoter in the vector BG1805. This vector can be introduced into ura3 yeast mutants and transformants selected for uracil prototrophy. In the presence of galactose and the absence of glucose, expression from the GAL1 promoter is elevated about 1000 fold relative to the barely detectable level observed with glucose grown cells (Johnston and Davis (1984) Mol. Cell. Biol. 4(8):1440-1448). Note that each ORF encodes a fusion protein of the form:

N Terminal Yeast ORF-C Terminal Epitope Tag

A plasmid containing the PBS2 ORF was obtained from this collection (YSC3867-9523439) and transformed into yeast strain BY4741 selecting for uracil prototrophy. To measure the effects of isobutanol we compare the growth observed in an isobutanol-treated culture in galactose medium to an untreated culture grown in the same medium lacking isobutanol. Growth yield was measured by the following method. A fresh colony of a transformant was used to inoculate a tube in which CM galactose minus uracil medium had been placed. This medium provides selection for plasmid maintenance. The resultant culture was incubated at 30° C. on a roller drum to provide aeration. The parent BY4741 was cultured in this medium modified by the inclusion of uracil to satisfy its uracil requirement. The culture was diluted into fresh medium (10 ml) to OD600 of approximately 0.4. Absorbance was recorded.

Cultures were grown for 2-3 hours to allow one doubling. Absorbance was recorded at this time and was called T=0. The culture was divided into two equal parts; each was diluted with an equal volume of pre-warmed fresh media. In one sample the fresh media was supplemented with 1 wt % isobutanol; in the other (control) the fresh media was unadulterated. OD600 was measured after incubation on a roller drum for 2 days. Absorbencies presented were averages of triplicate control and triplicate treated cultures. Percent growth was calculated as 100×[average A600 of the triplicate isobutanol challenged cultures/average A600 of the triplicate control cultures.

Results for a 48 hr experiment indicated that the parental strain (BY4741) grown in galactose displayed a 24% growth yield in the presence of 1 wt % isobutanol relative to the uninhibited culture (measures are averages of triplicate cultures with standard deviations of less than 10% under each of the conditions tested for both strains). In contrast, the PBS2p over-producing strain grown in galactose displayed a growth yield of 65% yield in the presence of 1 wt % isobutanol, a 41% improvement.

Example 3

Prophetic

Production of Isobutanol in Recombinant S. cerevisiae with Engineered Isobutanol Pathway and PBS2 Overexpression The purpose of this prophetic example is to describe how to enhance isobutanol production in a yeast strain by combining an isobutanol biosynthetic pathway with PBS2 overexpression. To this end we need to disrupt TRP1, the gene encoding phosphoribosylanthranilate isomerase that catalyzes the third step in tryptophan biosynthesis, to provide a third selectable marker. BY4741 is the starting strain. A cassette containing DNA sequences that are located upstream and downstream just outside of TRP1 (up TRP1 and downTRP1) is created containing the following elements: upTRP1 DR URA3* DR downTRP1, where DR are direct repeat sequences and URA3* is a heterologous URA3 gene. The upTRP1 DR URA3* DR downTRP1 fragment is constructed by the method of Reid et al. ((2002) Yeast 19(4):319-328). Following this method the 5' and 3' flanking regions of the TRP1 gene, which contain the up TRP1 and downTRP1 sequences, are prepared. These are called intergenic DNAs iYHR029C and iYHR030C, respectively.

Intergenic DNA iYDR006C is amplified from S. cerevisiae genomic DNA using PCR with primers:

```
Forward:
                                         (SEQ ID NO: 83)
ccgctgctaggcgcgccgtgTCTGAAAACGGAAGAGGAGTAGG Reverse:
                                         (SEQ ID NO: 84)
gcagggatgcggccgctgacATAACAGACATACTCCAAGCTGCC
```

Intergenic DNA iYDR008C is amplified from S. cerevisiae genomic DNA using PCR with primers:

```
Forward:
                                         (SEQ ID NO: 85)
ccgctgctaggcgcgccgtgCATTTGGCTTTTGATTGATTGTAC Reverse
                                         (SEQ ID NO: 86)
gcagggatgcggccgctgacACTTTTATTTTCTCTTTTTGCACTCCT
```

The two intergenic DNA PCR fragments are each used together with the plasmid pWJ1077, containing DR URA3*DR (Reid et al. ibid.), as template for PCR to produce DNA fragments containing each intergenic DNA sequence and a portion of the URA3* sequence, with overlap of the URA3* sequence between the two resulting fragments: upTRP1 DR UR and RA3* DR downTRP1. Primers for iYDR006C and pWJ1077 templates are C and kli3' (SEQ ID NOS:87 and 88). Primers for iYDR008C templates are D and kli5' (SEQ ID NOs: 89 and 90).

Co-transformation of these two fragments into yeast allows recombination between the two fragments to create a cassette containing an intact URA3* gene flanked by upTRP1 and downTRP1 sequences.

Recombination of this cassette into the yeast chromosome results in the replacement of TRP1 by DR URA3* DR. Transformants with this recombination event are selected by demanding growth in the absence of pyrimidines but in the presence of tryptophan. The recombinant requires tryptophan to grow. Excision of URA3* is accomplished by homologous recombination between the DR's and its loss is selected for with 5-FOA to create BY4741 ΔTRP1.

Construction of vectors pRS423::CUP1p-alsS+FBAp-ILV3 and pHR81::FBAp-ILV5-GPMp-kivD is described in US Patent Publication # US20070092957 A1, Example 17, which is herein incorporated by reference. pRS423::CUP1p-alsS+FBAp-ILV3 has a chimeric gene containing the CUP1 promoter (SEQ ID NO:91), the alsS coding region from *Bacillus subtilis* (SEQ ID NO:41), and CYC1 terminator (SEQ ID NO:92) as well as a chimeric gene containing the FBA promoter (SEQ ID NO:93), the coding region of the ILV3 gene of *S. cerevisiae* (SEQ ID NO:47), and the ADH1 terminator (SEQ ID NO:94). pHR81::FBAp-ILV5+GPMp-kivD is the pHR81 vector (ATCC #87541) with a chimeric gene containing the FBA promoter, the coding region of the ILV5 gene of *S. cerevisiae* (SEQ ID NO:43), and the CYC1 terminator as well as a chimeric gene containing the GPM promoter (SEQ ID NO:95), the coding region from kivD gene of *Lactococcus lactis* (SEQ ID NO:35), and the ADH1 terminator. pHR81 has URA3 and leu2-d selection markers.

Plasmid vectors pRS423::CUP1p-alsS+FBAp-ILV3 and pHR81::FBAp-ILV5+GPMp-kivD are transformed into BY4741ΔTRP1 using standard genetic techniques to yield the doubly transformed strain BY4741ΔTRP1-iso (Methods in Yeast Genetics, 2005, Cold Spring Harbor Laboratory Press, Cold Spring Harbor, N.Y.). BY4741ΔTRP1-iso is maintained on synthetic complete media lacking histidine and uracil.

Next the YRp7 plasmid (Botstein et al. (1979) Gene 8(1): 17-240), which is available from ATCC (catalog number 37060), and has unique restriction sites within the Tet gene (BamHI, SalI, EagI, NruI), is digested with BamHI to yield a linear fragment which is then dephosphorylated. To it is ligated the PBS2 gene fragment that is amplified, including 1 kbp of flanking sequence on both ends, from yeast chromosomal DNA using the primers:

ccatggt*ggatcc*GTTTGTCTTTTACTGCGGGA (SEQ ID NO: 96)

and ccatgg*ggatcc*ATATAGCAGGATTGAAGTTA. (SEQ ID NO: 97)

Prior to ligation the PCR product is digested with BamHI (restriction sites underlined and italicized) to yield compatible sticky ends. The resultant plasmid (YRp7-PBS2) is selected based upon ampicillin resistance in *E. coli* and is confirmed molecularly (liberation of an approximately 4 kbp fragment upon BamHI digestion) and phenotypically by being tetracycline sensitive. The plasmid is then isolated from *E. coli* and transformed into yeast strains, selecting for the ability to grow in the absence of tryptophan (TRP1 function).

BY4741ΔTRP1-iso is next transformed with yRP7-PBS2, selecting for the ability to grow without tryptophan supplementation, yielding BY4741ΔTRP1-iso-pBS2. BY4741ΔTRP1-iso is also transformed with yRP7 selecting for the ability to grow without tryptophan supplementation yielding BY4741ΔTRP1-iso-c. Aerobic cultures are grown in 250 ml flasks containing 50 ml synthetic complete media lacking histidine, tryptophan and uracil, and supplemented with 2% glucose in an Innova4000 incubator (New Brunswick Scientific, Edison, N.J.) at 30° C. and 225 rpm. Low oxygen cultures are prepared by adding 45 mL of medium to 60 mL serum vials that are sealed with crimped caps after inoculation and kept at 30° C. Approximately 24 h and 48 h after induction with 0.03 mM $CuSO_4$ (final concentration), an aliquot of the broth is analyzed by HPLC (Shodex Sugar SH1011 column (Showa Denko America, Inc. NY) with refractive index (RI) detection and GC (HP-Innowax, 0.32 mm×0.25 μm×30 m (Agilent Technologies, Inc., Santa Clara, Calif.) with flame ionization detection (FID) for isobutanol content. Isobutanol is detected. In preferred embodiments, more isobutanol is produced by BY4741 ΔTRP1-iso-PBS than by BY4741 ΔTRP1-iso-c.

What is claimed is:

1. A recombinant yeast cell comprising:
   a) an isobutanol biosynthetic pathway, wherein the isobutanol biosynthetic pathway comprises at least one gene encoding a polypeptide that performs at least one of the following substrate to product conversions:
      i) pyruvate to acetolactate, as catalyzed by acetolactate synthase;
      ii) acetolactate to 2,3-dihvdroxvisovalerate, as catalyzed by acetohydroxy acid isomeroreductase;
      iii) 2,3-dihydroxyisovalerate to α-ketoisovalerate, as catalyzed by acetohydroxy acid dehydratase or dihydroxyacid dehydratase;
      iv) α-ketoisovalerate to isobutyraldehyde, as catalyzed by branched-chain keto acid decarboxylase; and
      v) isobutyraldehyde to isobutanol, as catalyzed by a branched-chain alcohol dehydrogenase; and
   b) at least one genetic modification which increases activity of the high osmolarity/glycerol response pathway, wherein the genetic modification increases activity of a mitogen-activated protein kinase module of the high osmolarity/glycerol response pathway:
wherein the isobutanol biosynthetic pathway comprises at least one gene that is heterologous to the yeast cell and wherein the yeast cell has an increase in tolerance to isobutanol and an improvement in growth yield as compared with a yeast cell that lacks the at least one genetic modification of (b).

2. The recombinant yeast cell of claim 1 wherein the cell has at least a 40% improvement in growth yield in 1% (weight/volume) isobutanol as compared to a parental cell having no increase in activity of the high osmolarity/glycerol response pathway.

3. The recombinant yeast cell of claim 1 selected from the group consisting of *Saccharomyces, Schizosaccharomyces, Hansenula, Candida, Kluyveromyces, Yarrowia* and *Pichia*.

4. The yeast cell of claim 1 wherein the genetic modification increases PBS2 mitogen activated protein kinase kinase activity.

5. The yeast cell of claim 4 wherein the modification increasing PBS2 mitogen activated protein kinase kinase activity is overexpression of a PBS2 protein encoding gene.

6. The yeast cell of claim 5 wherein the PBS2 protein encoding gene is heterologous to the yeast cell.

7. The yeast cell of claim 1 wherein the at least one gene encoding the acetolactate synthase, acetohydroxy acid isomeroreductase, acetohydroxy acid dehydratase, dihydroxyacid dehydratase, branched-chain keto acid decarboxylase, or branched-chain alcohol dehydrogenase is heterologous to the yeast cell.

8. A method for improving fermentative production of isobutanol comprising:
   a) providing the recombinant yeast cell of claim 1; and
   b) contacting said yeast cell with fermentable sugar whereby said yeast cell produces isobutanol and said yeast cell has improved tolerance to said isobutanol and improved growth yield as compared to a yeast cell without the at least one genetic modification that increases activity of the mitogen-activated protein kinase module of the high osmolarity/glycerol response pathway.

* * * * *